United States Patent [19]
Audia et al.

[11] Patent Number: 5,635,528
[45] Date of Patent: Jun. 3, 1997

[54] INTERMEDIATES TO TETRAHYDRO-BETA-CARBOLINES

[75] Inventors: James E. Audia; James J. Droste; Deborah A. Evrard; Pawel Fludzinski, all of Indianapolis; Gwyn L. Murdoch, Greenwood; David L. Nelson, Carmel, all of Ind.

[73] Assignee: Eli Lilly and Company, Indianapolis, Ind.

[21] Appl. No.: 481,716

[22] Filed: Jun. 7, 1995

Related U.S. Application Data

[63] Continuation-in-part of Ser. No. 206,839, Mar. 11, 1994, Pat. No. 5,500,431, which is a continuation-in-part of Ser. No. 48,544, Apr. 14, 1993, abandoned.

[51] Int. Cl.$^6$ .................. A61K 31/405; C07D 209/16
[52] U.S. Cl. ...................... 514/415; 514/419; 548/504; 548/507
[58] Field of Search .................. 514/415, 419; 548/494, 504, 507

[56] References Cited

U.S. PATENT DOCUMENTS

| 3,304,309 | 2/1967 | Shavel et al. | 260/296 |
| 3,492,304 | 1/1970 | Shavel et al. | 260/288 |
| 4,614,807 | 9/1986 | Flaugh | 548/507 |

OTHER PUBLICATIONS

Chem. Abstract, "109(11) :93404s", vol. 109, p. 751 (1988).
Chem. Abstract, "83(13) :114719K", vol. 83, p. 591 (1975).
Chem. Abstract, "72(19) :100674c", vol. 72, p. 374 (1970).
Chem. Abstract, "77(25) :164922t", vol. 77, (1972).
Chem. Abstract, "94(11) :84091g", vol. 94, p. 726 (1981).
Chem. Abstract, "111(23) :208701x", vol. 111, (1989).
Chem. Abstract, "90(25) :203905e", vol. 90, p. 609 (1979).
Chem. Abstract, "94(3) :15940w", vol. 94, p. 465 (1981).
Chem. Abstract, "66(21) :95019n", vol. 66, p. 890 (1967).
Chem. Abstract, "88(21) :145971u", vol. 88, p. 22 (1978).
Chem. Abstracts, "78(19) :124791p", vol. 78, p. 505 (1973).
Derwent Publications, "J56045–459", Otsuka Pharm KK, filed Sep. 20, 1979, published Apr. 25, 1981.
Derwent Publications, "J55133–360", Shonot, filed Apr. 3, 1979, published Oct. 17, 1980.
Derwent Publications, "J50077–396", Nippon Chemifar, filed Nov. 13, 1973, published Jun. 24, 1975.
Derwent Publications, "J50024–299", Nippon Chemifar, filed Jun. 28, 1973, published Mar. 15, 1975.
Derwent Publications, "26,841", Upjohn Co., filed Jun. 11, 1963, published Jun. 1, 1967.
A. R. Stoit, et al., *Heterocycles* 22(8), 1687–91 (1984).
Shono et al., *J. Org. Chem.*, 48:1621–1628 (1983).
Liu et al., *J. Org. Chem.*, 48(1) 44–47 (1983).
Hudlicky et al., *J. Org. Chem.*, 46:1738–1741 (1981).
*J. Org. Chem.*, 47:2229–2231 (1982).
Chem. Abstracts, "90(5) :34483b", vol. 113, p. 25 (1990).
Chem. Abstracts, (Organic Chemistry) 4666 citing *Chem. Listy* 51, 1915–22 (1957).
Chem. Abstrcts, vol. 52:11039 citing *Monatsh. Chem.* 88, 1087–94 (1958).
Chem. Abstracts, vol. 54:1584 citing *Czech.* 86, 787 (1957).
Chem. Abstracts, vol. 55:21156 citing *Bull. Soc. Chim. France*, 643–653 (1960).
A. J. Bojarski et al. *Pharmazie* 48: 289–294 (1993).
Derwent Publications, "88–251823/36" citing EP–281,242A (Feb. 2, 1987) (Eli Lilly).
Derwent Publications, "89–060798/08" citing US 4,803,218 (Sep. 29, 1982). (McNeil).
Derwent Publications, "24,852" Oct. 20, 1961 Sano (Sandoz).
Derwent Publications, "15824e/09" citing BE–889,931 (Aug. 12, 1980) (Glaxo Group Ltd).
Derwent Publication "89–294822/42" EP–287–468–A Apr. 15, 1987 (15.04.87).
Derwent Publications "02629 J/48" EP—65–295(19.05.81).
Derwent Publications "30,476"Feb. 5, 1965 (5.2.65).
Derwent Publications "94–350720/44" EP 624569–A1 Feb. 28 1991 (28.02.91).
H. Rischke, et al., *Chem. Ber.* 106: 3106–3118 (1973).
W. Benson and E. Winterfeldt, *Chem. Ber.* 112: 1913–1915 (1979).
J. D. Wilcock and E. Winterfeldt, *Chem. Ber.* 107: 975–978 (1974).

*Primary Examiner*—Phyllis G. Spivack
*Attorney, Agent, or Firm*—MaCharri Vorndran-Jones; David E. Boone

[57] ABSTRACT

3-Ethanamine and 3-ethanamine related compounds are provided that are useful intermediates and have beneficial central nervous system activity.

9 Claims, No Drawings

INTERMEDIATES TO TETRAHYDRO-BETA-CARBOLINES

This application is a continuation in part of Ser. No. 08/206,839, filed on Mar. 11, 1994, which issued as U.S. Pat. No. 5,500,431 on Mar. 19, 1996, which is a continuation in part of Ser. No. 08/048,544, filed on Apr. 14, 1993, now abandoned.

FIELD OF THE INVENTION

The present invention relates to the field of organic chemistry. The invention provides novel tetrahydro-beta-carboline compounds and intermediates with a high affinity for the 5-$HT_{1C}$ receptor. Additionally, the invention provides 7-substituted tryptamine compounds with $5HT_{2A}$, $5HT_{2B}$, and/or $5HT_{2C}$ receptor activity.

BACKGROUND OF THE INVENTION

A substantial body of evidence supports the relationship between 5-$HT_{1c}$ receptor modulation and a variety of diseases and conditions. The 5$HT_{1c}$ receptor has recently been designated as the $5HT_{2c}$ receptor by researchers in this field. Hoyer, *Pharmacological Reviews* (draft document sanctioned by IUPHAR Receptor Nomenclature and Drug Classification Committee; Jul. 7, 1993). As used herein, the 5-$HT_{1c}$ receptor shall refer to the receptor now designated as $5HT_{2c}$.

The 5-$HT_{1C}$ receptor subtype was first detected in choroid plexus epithelial cells and is the only 5HT receptor subtype expressed by these cells. Studies of the 5-$HT_{1c}$ receptor using radioligand binding have been complex due to the cross reactivity of the 5-$HT_{1C}$ receptor with the 5-$HT_2$ receptor. The discovery of selective, high affinity compounds which discriminate between 5-$HT_{1C}$ and 5-$HT_2$ has been an elusive and important target. Hartig et al., The 5-$HT_{1C}$ Receptor *Annals New York Academy of Science*, 149, 159. Compounds with selective affinity for the 5-$HT_{1C}$ receptor can provide treatment for 5-$HT_{1C}$-receptor-mediated conditions without the side effects associated with activity at the 5-$HT_2$ receptor. Such compounds can simplify characterization of the 5-$HT_{1C}$ receptor and provide useful new therapeutic agents. In vitro, m-chlorophenylpiperazine (m-CPP) has a slightly higher affinity for the 5-$HT_{1C}$ sites than for other 5-HT receptors; however, prior to the present invention, there have been no known 5-$HT_{1c}$ selective ligands.

The activation of the 5-$HT_{1C}$ receptor has been associated with numerous behavioral and physiological effects. *TiPS*, 11, 181 (May 1990). The $5HT_{1C}$ receptors in the limbic system can affect mood, behavior, and hallucinogenesis. Hartig et al., The 5-$HT_{1C}$ Receptor *Annals New York Academy of Science*, 149, 159. Modulation of the $5HT_{1C}$ receptors has been associated with schizophrenia and schizophreniform disorders. Ugedo, L. et. al. *Psychopharmacology*, 98, 45 (1989); Canton H. et. al. *Eur. J. Pharmacol.*, 191, 93 (1990). Hypothalamic 5-$HT_{1C}$ receptors can influence sleep, appetite, thermoregulation, sexual behavior, motor activity, and neuroendocrine function. Hartig et al., The 5-$HT_{1C}$ Receptor *Annals New York Academy of Science*, 149, 159. Additionally, studies indicate that 5-$HT_{1C}$ receptors mediate hypoactivity, caused decreased feeding in rats, and have anxiogenic effects. Id. Studies have shown that drug-induced penile erections are 5-$HT_{1C}$ mediated. *Psychopharmacology*, 101, 57 (1990). Likewise, 5-$HT_{1C}$ modulation can treat or prevent priapism.

Other studies have used m-CPP to characterize responses associated with 5-$HT_{1C}$ receptors. Although responses to 5-$HT_{1C}$ are difficult to characterize by this method, the studies evince that 5-$HT_{1C}$ receptors influence the onset of anxiety, obsessive-compulsive disorders, panic disorders, Gilles de la Touratto syndrome and migraine headaches. *TiPS* 11, 181 (May 1990). The studies indicate that the 5-$HT_{1C}$ receptor can be involved in Alzheimer's disease as well. Id. The 5-$HT_{1C}$ receptor is involved in the modulation of the balance of cerebrospinal fluid. Further, the 5-$HT_{1C}$ receptor is associated with the sensation of pain. Zemlan, F. P. et al. *Neurochem. Int.*, 16, 507 (1990).

Further, compounds having affinity and selectivity for the $5HT_{2A}$, $5HT_{2B}$, or $5HT_{2C}$ receptor can be useful for treating a variety of conditions related to $5HT_{2A}$, $5HT_{2B}$, and $5HT_{2C}$ modulation. For example, compounds useful for the modulation of the $5HT_{2B}$ receptor are useful for treating patients suffering from or susceptible to a variety of conditions such as ichlasia, hypertonic lower esophageal sphinctor, tachygastria, hypermotility associated with irritable bowel syndrome, constipation, dyspepsia and/or other conditions associated with 5-$HT_{2B}$ modulation. Finally, modulation of the $5HT_{2A}$ receptor has been associated with schizophrenia, anxiety, depression, and migraines. Koek, W. *Neuroscience and Biobehavioral Reviews*, 16, 95–105 (1992).

It would be advantageous to have compounds which would permit modulation of the 5-$HT_{1C}$, $5HT_{2A}$, and/or 5HT2B receptors. It would be particularly desirable to have compounds with high 5-$HT_{1C}$ receptor affinity and low 5-$HT_2$ receptor affinity. It would be further advantageous to have compounds that minimize the effects of eating disorders, sexual disorders, and other disorders or conditions associated with 5-$HT_{2A}$, 5-$HT_{2B}$, and/or 5-$HT_{1C}$ modulation.

SUMMARY OF THE INVENTION

This invention provides a group of novel compounds with 5-$HT_{1C}$ receptor activity. The invention also provides compounds with the longed for selective 5-$HT_{1C}$ receptor antagonist activity. Additionally, the present compounds are useful tools to characterize the effects of the 5-$HT_{1C}$ receptor and to develop therapeutic agents based on 5-$HT_{1C}$ receptor modulation. Further, the present invention provides novel intermediates of Formula (VI) infra. for preparing compounds of Formula (I) infra.

The present invention provides a group of novel tryptamine compounds of Formula (VII) infra. with $5HT_{1A}$, $5HT_{2B}$, and/or $5HT_{2C}$ activity.

Thus, this invention relates to a compound of the formula (I)

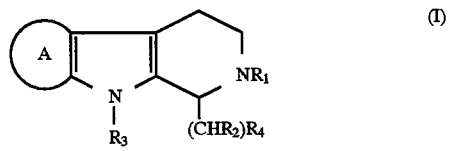

wherein:

$R_1$ is hydrogen or $C_1$–$C_3$ alkyl;

$R_2$ is hydrogen or $C_1$–$C_6$ alkyl;

$R_3$ is hydrogen or $C_1$–$C_3$ alkyl;

$R_4$ is $C_5$–$C_8$ cycloalkyl, substituted $C_5$–$C_8$ cycloalkyl, $C_5$–$C_8$ cycloalkenyl, substituted $C_5$–$C_8$ cycloalkenyl;

A is selected from the group consisting of

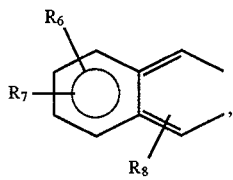
(II)

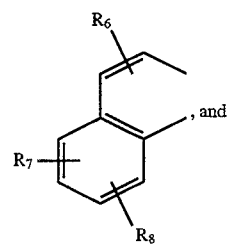
, and
(III)

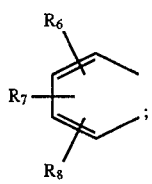
;
(IV)

wherein $R_6$ and $R_7$ are, independently, hydrogen, $C_1$–$C_6$ alkyl, $C_2$–$C_6$ alkenyl, halo, halo($C_1$–$C_6$)alkyl, halo($C_2$–$C_6$) alkenyl, $COR_5$, $C_1$–$C_{10}$ alkanoyl, $CO_2R_{5'}$, ($C_1$–$C_6$ alkyl)$_m$ amino, $NO_2$, —$SR_5$, or $OR_5$;

each $R_5$ is independently hydrogen or $C_1$–$C_4$ alkyl;

$R_{5'}$ is $C_1$–$C_4$ alkyl;

$R_8$ is selected from the group consisting of an $R_6$ group, substituted $C_3$–$C_8$ cycloalkyl, $C_3$–$C_8$ cycloalkyl, $C_3$–$C_8$ cycloalkyl-($C_1$–$C_3$)alkyl, $C_5$–$C_8$ cycloalkenyl, substituted $C_5$–$C_8$ cycloalkenyl, $C_5$–$C_8$ cycloalkenyl-($C_1$–$C_3$)alkyl, $C_7$–$C_{16}$ arylalkyl; or $R_6$ and $R_7$ together with the carbon atoms of group A form a 5- to 8-member carbon ring; and m is 1 or 2;

provided that, a) when A is a group of formula IV; $R_2$ is hydrogen or methyl; and $R_4$ is phenyl or substituted phenyl; then none of the group $R_6$, $R_7$, and $R_8$ can be $CO_2R_{5'}$ or $OR_5$; and at least one of the group $R_6$, $R_7$, and $R_8$ cannot be hydrogen; and b) when A is a group of the formula IV; one of $R_6$, $R_7$, or $R_8$ is halo; $R_4$ is phenyl; and the phenyl substitutents are $OR_5$, OH, or hydrogen; then the remaining two $R_6$, $R_7$, or $R_8$ cannot each be hydrogen; or a pharmaceutically acceptable salt or solvate thereof.

The present invention also provides methods of employing and pharmaceutical formulations containing, a compound of formula (V)

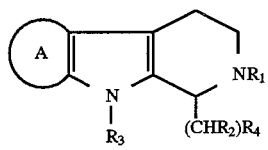
(V)

wherein:

$R_1$ is hydrogen or $C_1$–$C_3$ alkyl;
$R_2$ is hydrogen or $C_1$–$C_6$ alkyl;
$R_3$ is hydrogen or $C_1$–$C_3$ alkyl;
$R_4$ is $C_5$–$C_8$ cycloalkyl, substituted $C_5$–$C_8$ cycloalkyl, $C_5$–$C_8$ cycloalkenyl, substituted $C_5$–$C_8$ cycloalkenyl;

A is selected from the group consisting of

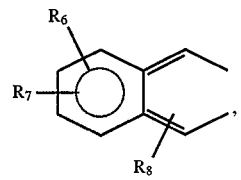
(II)

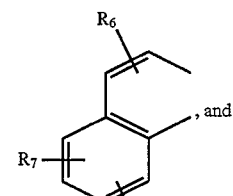
, and
(III)

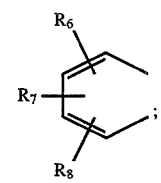
;
(IV)

wherein $R_6$ and $R_7$ are, independently, hydrogen, $C_1$–$C_6$ alkyl, $C_2$–$C_6$ alkenyl, halo, halo($C_1$–$C_6$)alkyl, halo($C_2$–$C_6$) alkenyl, $COR_5$, $C_1$–$C_{10}$ alkanoyl, $CO_2R_{5'}$, ($C_1$–$C_6$ alkyl)$_m$ amino, $NO_2$, —$SR_5$, or $OR_5$;

m is 1 or 2;

$R_5$ is independently hydrogen or $C_1$–$C_4$ alkyl;

$R_{5'}$ is $C_1$–$C_4$ alkyl;

$R_8$ is independently selected from the group consisting of an $R_6$ group, substituted $C_3$–$C_8$ cycloalkyl, $C_3$–$C_8$ cycloalkyl, $C_3$–$C_8$ cycloalkyl-($C_1$–$C_3$)alkyl, $C_5$–$C_8$ cycloalkenyl, substituted $C_5$–$C_8$ cycloalkenyl, $C_5$–$C_8$ cycloalkenyl-($C_1$–$C_3$)alkyl, $C_7$–$C_{16}$ arylalkyl; or $R_6$ and $R_7$ together with the carbon atoms of group A form a 5- to 8-member carbon ring; or a pharmaceutically acceptable salt or solvate thereof.

This invention provides useful compounds of Formula (VI)

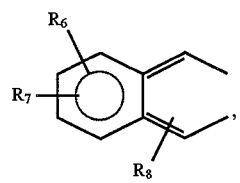
(VI)

wherein:

$R_3$ is hydrogen or $C_1$–$C_3$ alkyl;

A is selected from the group consisting of

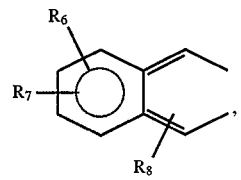
(II)

-continued

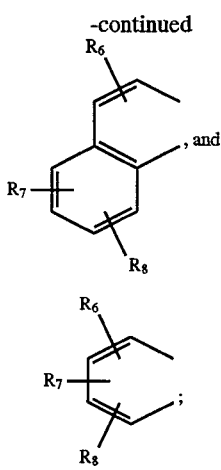

wherein $R_6$ and $R_7$ are, independently, hydrogen, $C_1-C_6$ alkyl, $C_2-C_6$ alkenyl, halo, halo($C_1-C_6$)alkyl, halo($C_2-C_6$) alkenyl, $COR_5$, $C_1-C_{10}$ alkanoyl, $CO_2R_5$, ($C_1-C_6$ alkyl)$_m$ amino, $NO_2$, $-SR_5$, or $OR_5$;

$R_5$ is independently hydrogen or $C_1-C_4$ alkyl;

$R_{5'}$ is $C_1-C_4$ alkyl;

$R_8$ is independently selected from the group consisting of an $R_6$ group, substituted $C_3-C_8$ cycloalkyl, $C_3-C_8$ cycloalkyl, $C_3-C_8$ cycloalkyl-($C_1-C_3$)alkyl, $C_5-C_8$ cycloalkenyl, substituted $C_5-C_8$ cycloalkenyl, $C_5-C_8$ cycloalkenyl-($C_1-C_3$)alkyl, $C_7-C_{16}$ arylalkyl; or $R_9$ and $R_{10}$ are independently selected from the group consisting of hydrogen, $C_1-C_6$ alkyl, substituted $C_3-C_8$ cycloalkyl, $C_3-C_8$ cycloalkyl, $C_3-C_8$ cycloalkyl-($C_1-C_3$) alkyl, $C_5-C_8$ cycloalkenyl-($C_1-C_3$)alkyl, $C_7-C_{16}$ arylalkyl;

$R_6$ and $R_7$ together with the carbon atoms of group A form a 5- to 8-member carbon ring;

$R_{12}$ is selected from the group consisting of hydrogen, and $C_1-C_3$ alkyl;

m is 1 or 2;

provided that, a) when A is

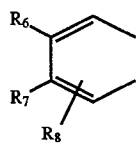

wherein $R_6$ and $R_7$ are selected from the group consisting of hydrogen, halo, and $OR_5$; then $R_8$ cannot be hydrogen;

or a pharmaceutically acceptable salt or solvate thereof.

DETAILED DESCRIPTION OF THE INVENTION

The term "treating" as used herein includes prophylaxis of the named physical and/or mental condition or amelioration or elimination of the developed physical and/or mental condition once it has been established.

The phrase "injury to the central nervous system" includes, but is not limited to, injury to the spinal cord, neural tube, or dura of the brain. Injury to the central nervous system also includes priapism, cerebrospinal fluid imbalances, and other 5-$HT_{1C}$ imbalances, and related conditions resulting from central nervous system injury.

The terms "$C_1-C_n$ alkyl" wherein n=2–10, as used herein, represent a branched or linear alkyl group having from one to the specified number of carbon atoms. Typical $C_1-C_6$ alkyl groups include methyl, ethyl, n-propyl, iso-propyl, butyl, iso-butyl, sec-butyl, tert-butyl, pentyl, hexyl and the like.

The terms "$C_2-C_n$ alkenyl" wherein n=3–10, as used herein, represents an olefinically unsaturated branched or linear group having from 2 to 10 carbon atoms and at least one double bond. The groups can be branched or straight chain. Examples of such groups include 1-propenyl, 2-propenyl ($-CH_2-CH=CH_2$), 1,3-butadienyl ($-CH=CHCH=CH_2$), 1-butenyl ($-CH=CHCH_2CH_3$), hexenyl, pentenyl, and the like.

The terms "halide", "halogen", and "halo" include fluorine, chlorine, bromine, and iodine. The preferred halogen is chlorine.

The terms "halo($C_1-C_6$)alkyl" and "halo($C_2-C_6$)alkenyl" refer to alkyl or alkenyl substituents having one or more independently selected halo atoms attached at one or more available carbon atoms. These terms include chloromethyl, bromoethyl, trifluoroethyl, trifluoromethyl, trifluoroethylenyl, 3-bromopropyl, 3-bromo-1-propenyl, 2-bromopropyl, 2-bromo-1-propenyl, 3-chlorobutyl, 3-chloro-2-butenyl, 2,3-dichlorobutyl, chloroethylenyl, 5-fluoro-3-pentenyl, 3-chloro-2-bromo-5-hexenyl, 3-chloro-2-bromobutyl, trichloromethyl, dichloroethyl, 1,4-dichlorobutyl, 3-bromopentyl, 1,3-dichlorobutyl, 1,1-dichloropropyl, and the like. More preferred halo-($C_1-C_6$) alkyl groups are trichloromethyl, trichloroethyl, and trifluoromethyl. The most preferred halo-($C_1-C_6$)alkyl is trifluoromethyl.

The term "$C_1-C_{10}$ alkanoyl" represents a group of the formula $C(O)(C_1-C_9)$ alkyl. Typical $C_1-C_{10}$ alkanoyl groups include acetyl, propanoyl, butanoyl, and the like.

The term "($C_1-C_6$ alkyl)$_m$ amino" wherein m=1–2; refers to either a mono- or a dialkylamino group in which the alkyl portion of the group may be straight or branched. Examples of such groups are methylamino, dimethylamino, ethylamino, diethylamino, 2-propylamino, 1-propylamino, di(n-propyl)amino, di(iso-propyl)amino, methyl-n-propylamino, t-butylamino, and the like.

The term "$C_3-C_n$ cycloalkyl" wherein n=4–8, represents cyclopropyl, cyclobutyl, cyclopentyl, cyclohexyl, cycloheptyl, and cyclooctyl.

The term "substituted($C_5-C_n$) cycloalkyl" refers to a cycloalkyl group as described supra wherein the cycloalkyl group may be substituted with from one to four substituents independently selected from the group consisting of hydrogen, $C_1-C_6$ alkyl, $NO_2$, halo, halo($C_1-C_6$)alkyl, halo ($C_2-C_6$)alkenyl, $C_2-C_6$ alkenyl, $CO_2R_5$, ($C_1-C_6$ alkyl)$_m$ amino, $-SR_5$, and $OR_5$.

The term "$C_3-C_8$ cycloalkyl-($C_1-C_3$)alkyl" represents a linear alkyl group substituted at a terminal carbon with a $C_3-C_8$ cycloalkyl group. Typical cycloalkylalkyl groups include cyclohexylethyl, cyclohexylmethyl, 3-cyclopentylpropyl, and the like.

The term "$C_5-C_8$ cycloalkenyl" represents an olefinically unsaturated ring having five to eight carbon atoms, eg., phenyl, cyclohexadienyl, cyclohexenyl, cyclopentenyl, cycloheptenyl, cyclooctenyl, cyclohexadienyl, cycloheptadienyl, cyclooctatrienyl and the like.

The term "substituted ($C_5$–$C_8$) cycloalkenyl" refers to a cycloalkenyl group as described supra wherein the cycloalkenyl group may be substituted with from one to four substituents independently selected from the group consisting of hydrogen, $C_1$–$C_6$ alkyl, $NO_2$, halo, halo($C_1$–$C_6$)alkyl, halo($C_2$–$C_6$)alkenyl, $C_2$–$C_6$ alkenyl, $COR_5$, $C_1$–$C_{10}$ alkanoyl, $C_7$–$C_{16}$ arylalkyl, $CO_2R_5$, ($C_1$–$C_6$ alkyl)$_m$ amino, —$SR_5$, and $OR_5$.

The term "$C_5$–$C_8$ cycloalkenyl-($C_1$–$C_3$)alkyl" represents a linear $C_1$–$C_3$ alkyl group substituted at a terminal carbon with a $C_5$–$C_8$ cycloalkenyl group.

The term "aryl" represents phenyl or naphthyl. The aryl group can be unsubstituted or can have one or two substituents independently selected from the group consisting of $C_1$–$C_6$ alkyl, $C_3$–$C_8$ cycloalkyl, substituted $C_3$–$C_8$ cycloalkyl, $C_2$–$C_6$ alkenyl, $C_3$–$C_8$ cycloalkyl-($C_1$–$C_3$)alkyl, phenyl, $C_5$–$C_8$ cycloalkenyl, substituted $C_5$–$C_8$ cycloalkenyl, $C_5$–$C_8$ cycloalkenyl-($C_1$–$C_3$)alkyl, $COR_5$, $C_1$–$C_{10}$ alkanoyl, $OR_5$, and $C_7$–$C_{16}$ arylalkyl. The substituents may be located at any available position on the aryl ring.

The term "$C_7$–$C_{16}$ arylalkyl" represents an aryl-($C_1$–$C_{10}$) alkyl substituent wherein the alkyl group is linear, such as benzyl, phenethyl, 3-phenylpropyl, or phenyl-t-butyl; or branched. The alkyl portion bonds at the point of attachment to the parent molecule.

The term "selective binding of a 5-$HT_{1C}$ receptor" refers to a method of binding the 5-$HT_{1C}$ receptor to a greater extent than it binds the 5-$HT_2$ receptor.

The term "protic acid" refers to an acid having an acidic hydrogen. Preferred protic acids include hydrochloric acid, formic acid, perchloric acid, sulfuric acid, and phosphoric acid in an aqueous medium. The most preferred protic acids are hydrochloric acid, sulfuric acid, and formic acid.

The term "organic solvent" includes solvents containing carbon, such as halogenated hydrocarbons, ether, toluene, xylene, benzene, and tetrahydrofuran.

The term "agitate" includes such techniques as stirring, centrifugation, mixing, and other similar methods.

The term "aprotic solvent" refers to polar solvents of moderately high dielectric constant which do not contain an acidic hydrogen. Examples of common aprotic solvents are dimethyl sulfoxide (DMSO), dimethylformamide, sulfolane, tetrahydrofuran, diethyl ether, methyl-t-butyl ether, or 1,2-dimethoxyethane.

The term "protic solvent" refers to a solvent containing hydrogen that is attached to oxygen, and hence is appreciably acidic. Common protic solvents include such solvents as water, methanol, ethanol, 2-propanol, and 1-butanol.

The term "inert atmosphere" refers to reaction conditions in which the mixture is covered with a layer of inert gas such as nitrogen or argon.

Abbreviations used herein have their accepted meaning, unless stated otherwise. For example, "Me" and "Et" refer to methyl, ethyl respectively, and "t-Bu" refers to tertiary-butyl. The abbreviation "RT" refers to room temperature or ambient conditions unless indicated otherwise.

The term "ligand" refers to compounds that are bound by the 5-$HT_{1C}$ and/or 5-$HT_2$ receptor. Compounds useful as 5-$HT_{1C}$ selective ligands may be used to selectively occupy a 5-$HT_{1C}$ receptor site or may act as a selective agonist at a 5-$HT_{1C}$ receptor site. Likewise, compounds which are 5-$HT_{2B}$ or 5-$HT_{2A}$ selective ligands may be used to selectively occupy a 5-$HT_{2A}$ or 5-$HT_{2B}$ receptor site, respectively.

The term "substantially pure" is intended to mean at least about 90 mole percent, more preferably at least about 95 mole percent, and most preferably at least about 98 mole percent of the desired enantiomer or stereoisomer is present compared to other possible configurations.

As used herein the term "functional bowel disorder" refers to a functional gastrointestinal disorder manifested by (1) abdominal pain and/or (2) symptoms of disturbed defecation (urgency, straining, feeling of incomplete evacuation, altered stool form [consistency] and altered bowel frequency/timing) and/or (3) bloating (distention). The term "functional bowel disorder" includes but is not limited to irritable bowel syndrome, hypermotility, ichlasia, hypertonic lower esophageal sphincter, tachygastria, constipation, hypermotility associated with irritable bowel syndrome.

The formula (I) and all compounds claimed herein can form acid addition salts with a wide variety of inorganic and organic acids. Typical acids which can be used include sulfuric, hydrochloric, hydrobromic, phosphoric, hypophosphoric, hydroiodic, sulfamic, citric, acetic, maleic, malic, succinic, tartaric, cinnamic, benzoic, ascorbic, mandelic, p-toluenesulfonic, benzenesulfonic, methanesulfonic, trifluoroacetic, hippuric and the like. The pharmaceutically acceptable acid addition salts of the formula (I) compounds are especially preferred.

The compounds of the present invention are useful for modulating or blocking the 5-$HT_{1C}$ receptor. Certain of the present compounds are preferred for that use. Preferred Formula (I) compounds are those having the following characteristics:

A) $R_1$ is hydrogen;

B) $R_2$ is hydrogen or methyl;

C) $R_3$ is hydrogen or methyl;

D) $R_4$ is $C_5$–$C_8$ cycloalkenyl or substituted $C_5$–$C_8$ cycloalkenyl, wherein the substituents are selected from the group consisting of hydrogen, $C_1$–$C_6$ alkyl, $NO_2$, halo, halo($C_1$–$C_6$)alkyl, $C_2$–$C_6$ alkenyl, $COR_5$, ($C_1$–$C_6$ alkyl)$_m$ amino, —$SR_5$, and $OR_5$.

E) A is a group of formula III;

F) A is a group of formula IV wherein $R_6$ and $R_7$ are $C_1$–$C_6$ alkyl or halo, and $R_8$ is hydrogen, $C_1$–$C_5$ alkyl, halo, $C_5$–$C_8$ cycloalkyl, phenyl or substituted-phenyl;

G) $R_2$ is hydrogen;

H) $R_3$ is hydrogen;

I) $R_4$ is substituted $C_5$–$C_8$ cycloalkenyl; wherein the substituents are selected from the group consisting of hydrogen, $NO_2$, halo, ($C_1$–$C_6$ alkyl)$_m$ amino, and $OR_5$;

J) A is a group of formula IV wherein $R_6$ is hydrogen, $R_7$ and $R_8$ are independently selected from the group consisting of halo and $C_1$–$C_4$ alkyl;

K) A is a group of formula IV wherein $R_2$ is hydrogen or $C_{1-3}$ alkyl; $R_4$ is non-aromatic $C_6$ alkenyl or $OR_5$ mono-substituted non-aromatic $C_6$ alkenyl; and at least one of the group consisting of $R_6$, $R_7$, and $R_8$ is not hydrogen;

L) A is a group of formula IV wherein $R_2$ is hydrogen or $C_{1-3}$ alkyl; $R_4$ is non-aromatic $C_6$ alkenyl or mono-substituted non-aromatic $C_6$ alkenyl wherein the substituent is selected from the group consisting of —$SR_5$, $OR_5$ and $COR_5$; and at least one of the group consisting of $R_6$, $R_7$, and $R_8$ is not hydrogen;

M) A is a group of formula IV wherein $R_2$ is hydrogen or $C_{1-3}$ alkyl; $R_4$ is non-aromatic $C_6$ alkenyl or $OR_5$ substituted non-aromatic $C_6$ alkenyl; and at least one of the group consisting of $R_6$, $R_7$, and $R_8$ is not hydrogen or methyl;

N) A is a group of formula II or III wherein $R_6$ is hydrogen, $R_7$ and $R_8$ are independently selected from the group consisting of halo and $C_1$–$C_4$ alkyl;

O) A is a group of formula II or III wherein $R_2$ is hydrogen or $C_{1-3}$ alkyl; $R_4$ is non-aromatic $C_6$ alkenyl or $OR_5$ mono-substituted non-aromatic $C_6$ alkenyl; and at least one of the group consisting of $R_6$, $R_7$, and $R_8$ is not hydrogen;

P) A is a group of formula II or III wherein $R_2$ is hydrogen or $C_{1-3}$ alkyl; $R_4$ is non-aromatic $C_6$ alkenyl or mono-substituted non-aromatic $C_6$ alkenyl wherein the substituent is selected from the group consisting of $-SR_5$, $OR_5$ and $COR_5$; and at least one of the group consisting of $R_6$, $R_7$, and $R_8$ is not hydrogen;

Q) A is a group of formula II or III wherein $R_2$ is hydrogen or $C_{1-3}$ alkyl; $R_4$ is non-aromatic $C_6$ alkenyl or substituted non-aromatic $C_6$ alkenyl; and at least one of the group consisting of $R_6$, $R_7$, and $R_8$ is not hydrogen or methyl.

The more preferred classes have the following features:

A–C, E or F and I.

The most preferred class of compounds has the following features:

A and G–J.

The preferred classes of compounds for use as selective 5-$HT_{1C}$ ligands have the following features:

A–D and E or J.

The most preferred class of compounds for use as selective 5-$HT_{1C}$ ligands has the following features:

A and G–J.

The Formula (I) compounds have useful central nervous system activity. Table I illustrates several of the Formula (I) compounds. The terms in the column headings of Table I refer to Formula (I). As used in the table, the headings "S1", "S2", and "S3" refer to the substituents on the $R_4$ group. It is intended that the formulas in the $R_4$ column merely refer to the $R_4$ structural nucleus. The three substituents listed in columns $R_4S_1$, $R_4S_2$ and $R_4S_3$ may replace any of the hydrogen atoms in the $R_4$ formula to provide the desired compounds.

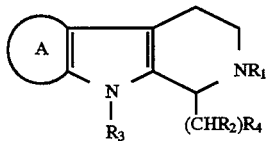

(I)

The abbreviations for $R_4$ refer to the following:

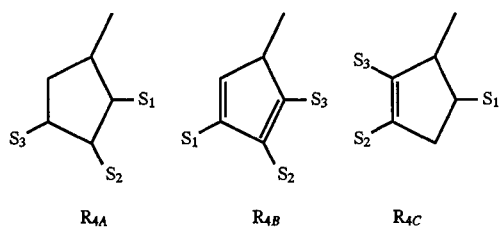

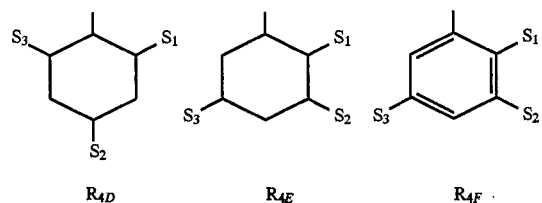

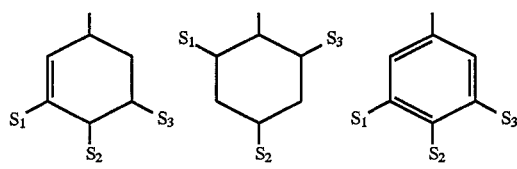

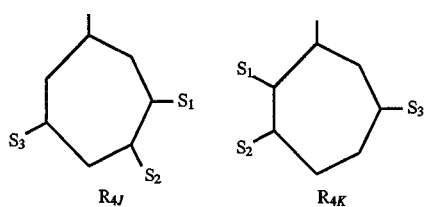

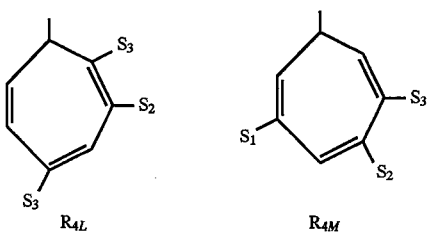

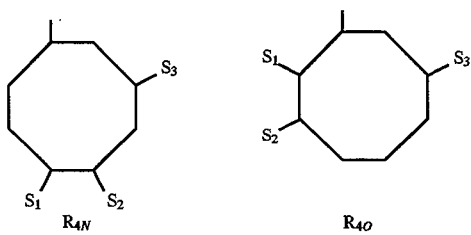

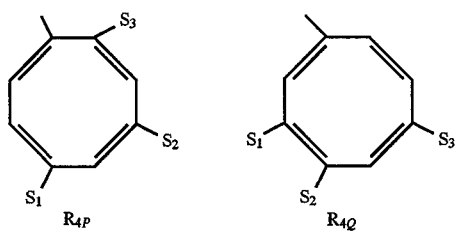

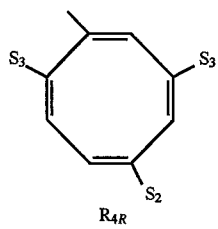

TABLE I

| A | R₁ | R₂ | R₃ | R₄ | R₆ | R₇ | R₈ | S₁ | S₂ | S₃ |
|---|---|---|---|---|---|---|---|---|---|---|
| II | H | H | H | $R_{4A}$ | H | Me | H | H | OMe | |
| III | Me | Me | Me | $R_{4B}$ | Me | Me | H | | OMe | H |
| IV | Et | Et | Et | $R_{4C}$ | H | Br | F | OMe | OMe | H |
| II | H | 1-hexyl | Pr | $R_{4D}$ | Et | H | H | NMe₂ | H | H |
| III | Me | 2-heptyl | H | $R_{4E}$ | —CH=CH₂ | Cl | H | NBu₂ | H | H |
| IV | Et | i-Pr | Me | $R_{4F}$ | H | C₃H₅ | F | NPr₂ | H | H |
| II | H | t-Bu | Et | $R_{4G}$ | H | H | C₄H₇ | NHMe | H | H |
| III | Me | i-Bu | Pr | $R_{4H}$ | OH | OMe | H | NHBu | H | H |
| IV | Et | Pr | H | $R_{4I}$ | H | H | Ph | NHPr | H | F |
| II | H | Bu | Me | $R_{4J}$ | NO₂ | t-Bu | H | CH₂Cl | H | H |
| III | Me | H | Et | $R_{4K}$ | Pr | Me | F | OH | OMe | F |
| IV | Et | Me | Pr | $R_{4L}$ | H | H | C₁₀H₇ | NO₂ | OMe | OMe |
| II | H | Et | H | $R_{4M}$ | Cl | CH₂Br | H | Cl | OH | Br |
| III | Me | H | Me | $R_{4N}$ | —C—Cl=CH₂ | F | H | Cl | OMe | OH |
| IV | Et | Me | H | $R_{4O}$ | OMe | OMe | OMe | Br | OMe | OMe |
| II | Pr | Bu | Me | $R_{4P}$ | OEt | OMe | OH | SH | H | F |
| II | H | H | H | $R_{4Q}$ | H | NMe₂ | NHMe | NO₂ | H | H |
| III | Me | Me | Me | $R_{4R}$ | CH₂F | H | Et | H | F | NHBu |
| IV | Et | Et | Et | $R_{4A}$ | —CH=CHBr | H | Me | COMe | NMe₂ | H |
| II | H | Pr | Pr | $R_{4B}$ | F | CO₂H | H | CO₂H | H | H |
| III | Me | Bu | H | $R_{4C}$ | H | NO₂ | CO₂CH₃ | OMe | NO₂ | OMe |
| IV | Et | 2-butyl | Me | $R_{4D}$ | Br | OH | OEt | OEt | NMe₂ | OMe |
| II | H | C₅H₁₁ | Et | $R_{4E}$ | H | OMe | OMe | NMe₂ | H | H |
| III | Me | C₆H₁₃ | Pr | $R_{4F}$ | H | OEt | Cl | Cl | OMe | OMe |
| IV | Et | H | H | $R_{4G}$ | F | OBu | C₆H₅ | F | OEt | OH |
| II | H | Me | Me | $R_{4H}$ | OMe | OPr | C₆H₅ | OMe | OH | NO₂ |
| III | Pr | Et | Et | $R_{4I}$ | H | H | H | H | H | H |
| IV | Pr | Pr | Pr | $R_{4J}$ | H | H | H | H | H | H |
| II | Pr | Bu | H | $R_{4K}$ | H | H | H | H | H | H |
| III | Me | H | Me | $R_{4L}$ | OMe | H | C₁₀H₇ | Br | Br | SH |
| IV | Me | Me | Et | $R_{4M}$ | Cl | NMe₂ | NO₂ | OMe | F | COC₂H₅ |
| II | H | H | Pr | $R_{4N}$ | Me | Et | COC₂H₅ | OMe | OMe | OMe |

Compounds of Formula VI having the structure of Formula VII (infra.) are especially preferred for modulating 5-HT$_{2A}$, 5-HT$_{2B}$, and/or 5-HT$_{2C}$ receptors:

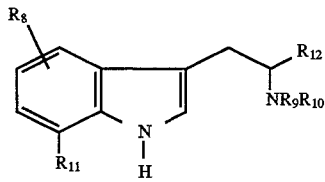

(VII)

wherein R₈ is selected from the group consisting of hydrogen, C₁–C₆ alkyl, C₂–C₆ alkenyl, halo, halo(C₁–C₆) alkyl, halo(C₂–C₆)alkenyl, COR₅, C₁–C₁₀ alkanoyl, CO₂R₅', (C₁–C₆ alkyl)$_m$ amino, NO₂, —SR₅, OR₅, substituted C₃–C₈ cycloalkyl, C₃–C₈ cycloalkyl, C₃–C₈ cycloalkyl-(C₁–C₃) alkyl, C₅–C₈ cycloalkenyl, substituted C₅–C₈ cycloalkenyl, C₅–C₈ cycloalkenyl-(C₁–C₃) alkyl, and C₇–C₁₆ arylalkyl;

R₅ is independently hydrogen or C₁–C₄ alkyl;

R₅' is C₁–C₄ alkyl;

R₉ and R₁₀ are independently selected from the group consisting of hydrogen, C₁–C₆ alkyl, substituted C₃–C₈ cycloalkyl, C₃–C₈ cycloalkyl, C₃–C₈ cycloalkyl-(C₁–C₃) alkyl, C₅–C₈ cycloalkenyl-(C₁–C₃)alkyl, C₇–C₁₆ arylalkyl;

R₁₁ is selected from the group consisting of C₁–C₄ alkyl, OR₅', fluoro, bromo, iodo, and chloro;

R₁₂ is selected from the group consisting of hydrogen, and C₁–C₃ alkyl;

or a pharmaceutically acceptable salt or solvate thereof.

Compounds of Formula VII are particularly useful for modulating 5HT$_{2A}$, 5HT$_{2B}$, and/or 5HT$_{2C}$ receptors. Certain compounds within the scope of this invention are preferred for that use. The following invention embodiments and compound characteristics listed in tabular form may be independently combined to produce a variety of preferred compounds and embodiments of the invention. The following list of embodiments of this invention is in no way intended to limit the scope of this invention in any way.

A) R₉ and R₁₀ are each hydrogen.
B) R₁₁ is C₁–C₃ alkyl.
C) R₁₁ is chloro, fluoro, or bromo.
D) R₁₁ is —OCH₃.
E) R₆ is C₁–C₄ alkyl.
F) R₆ is methyl.
G) A method for binding a 5HT$_{2A}$ receptor using one or more compounds of Formula VII.
H) A method for binding a 5HT$_{2B}$ receptor using one or more compounds of Formula VII.
I) A method for binding a 5HT$_{2C}$ receptor using one or more compounds of Formula VII.
J) A method of using one or more compounds of Formula VII for treating a functional bowel disorder.
K) A method of using one or more compounds of Formula VII which are useful for modulatation of the 5HT$_{2B}$ receptor for treating a function bowel disorder.
L) A method for using one or more compounds of Formula VII for treating Irritable Bowel Syndrome.
M) A pharmaceutical formulation comprising a compound of Formula VII and one or more pharmaceutically acceptable excipients;
N) A compound wherein A is formula IV'; R₆ and R₇ are selected from the group consisting of hydrogen, halo, and OR₅; and R₈ is not hydrogen;
O) A compound wherein A is formula IV'; wherein R₉, R₁₀, and R₁₂ are each hydrogen; R₆ is OR₅; and one of the group consisting of R₇ and R₈ cannot be hydrogen;
P) A compound wherein A is formula IV; wherein R₉, R₁₀, and R₁₂ are each hydrogen; two of the group consisting of R₆, R₇, and R₈ are each selected from the group consisting of halo, $C_1$–$C_6$ alkyl, $OR_5$, and —$SR_5$; the third substituent selected from the group consisting of $R_6$, $R_7$, and $R_8$ is not hydrogen; or if one of the two selected from the group consisting of $R_6$, $R_7$, and $R_8$ is selected from the group consisting of halo, $C_1$–$C_6$ alkyl, $OR_5$ and —$SR_5$ is halo, then the halo group is located at the 7 position of the tryptamine compound;

Q) A compound wherein A is formula IV; wherein $R_9$, $R_{10}$, and $R_{12}$ are each hydrogen; or $R_{12}$ is $C_1$–$C_3$ alkyl; two of the group consisting of $R_6$, $R_7$, and $R_8$ are hydrogen, and the third substituent is selected from the group consisting of $R_6$, $R_7$, and $R_8$ is not selected from the group consisting of $C_1$–$C_6$ alkyl, halo, halo($C_1$–$C_6$)alkyl, $NO_2$, —$SR_5$, and $OR_5$;

R) A compound wherein A is IV; $R_9$, $R_{10}$, and $R_{12}$ are each hydrogen; and $R_8$ is selected from the group consisting of halo($C_1$–$C_6$)alkyl, halo($C_2$–$C_6$)alkenyl, $C_1$–$C_{10}$ alkanoyl, $CO_2R_5$, ($C_1$–$C_6$ alkyl)$_m$amino, substituted $C_3$–$C_8$ cycloalkyl, $C_3$–$C_8$ cycloalkyl, $C_3$–$C_8$ cycloalkyl-($C_1$–$C_3$) alkyl, $C_5$–$C_8$ cycloalkenyl, substituted $C_5$–$C_8$ cycloalkenyl, $C_5$–$C_8$ cycloalkenyl-($C_1$–$C_3$)alkyl and arylalkyl.

S) A compound wherein A is formula II or IV; $R_6$ and $R_7$ are selected from the group consisting of hydrogen, halo, and $OR_5$; and $R_8$ is not hydrogen;

T) A compound wherein A is formula IV; wherein $R_9$, $R_{10}$, and $R_{12}$ are each hydrogen; $R_6$ is $OR_5$; and one of the group consisting of $R_7$ and $R_8$ cannot be hydrogen;

U) A compound wherein A is formula II or III; wherein $R_9$, $R_{10}$, and $R_{12}$ are each hydrogen; two of the group consisting of $R_6$, $R_7$, and $R_8$ are each selected from the group consisting of halo, $C_1$–$C_6$ alkyl, $OR_5$, and —$SR_5$; the third substituent selected from the group consisting of $R_6$, $R_7$, and $R_8$ is not hydrogen; or if one of the two selected from the group consisting of $R_6$, $R_7$, and $R_8$ is selected from the group consisting of halo, $C_1$–$C_6$ alkyl, $OR_5$ and —$SR_5$ is halo, then the halo group is located at the 7 position of the tryptamine compound;

V) A compound wherein A is formula II or III; wherein $R_9$, $R_{10}$, and $R_{12}$ are each hydrogen; or $R_{12}$ is $C_1$–$C_3$ alkyl; two of the group consisting of $R_6$, $R_7$, and $R_8$ are hydrogen, and the third substituent is selected from the group consisting of $R_6$, $R_7$, and $R_8$ is not selected from the group consisting of $C_1$–$C_6$ alkyl, halo, halo($C_1$–$C_6$)alkyl, $NO_2$, —$SR_5$, and $OR_5$;R) A compound wherein $R_9$, $R_{10}$, and $R_{12}$ are each hydrogen; and $R_8$ is selected from the group consisting of halo($C_1$–$C_6$)alkyl, halo($C_2$–$C_6$)alkenyl, $C_1$–$C_{10}$ alkanoyl, $CO_2R_5$, ($C_1$–$C_6$ alkyl)$_m$amino, substituted $C_3$–$C_8$ cycloalkyl, $C_3$–$C_8$ cycloalkyl, $C_3$–$C_8$ cycloalkyl-($C_1$–$C_3$)alkyl, $C_5$–$C_8$ cycloalkenyl, substituted $C_5$–$C_8$ cycloalkenyl, $C_5$–$C_8$ cycloalkenyl-($C_1$–$C_3$)alkyl and arylalkyl.

Examples of compounds of Formula VI include but are in no way limited to 6,7-dimethyl-1H-indole-3-ethanamine, 5-methyl-7-bromo-1H-indole-3-ethanamine, 6-methyl-7-chloro-1H-indole-3-ethanamine, 6-bromo-7-methyl-1H-indole-3-ethanamine, 1-H-Benz(G)indole-3-ethanamine, 5-methyl-7-chloro-1H-indole-3-ethanamine, 7-chloro-1H-indole-3-ethanamine, 7-methoxy-1H-indole-3-ethanamine, 7-fluoro-1H-indole-3-ethanamine, 7-bromo-1H-indole-3-ethanamine, 6-methyl-7-bromo-1H-indole-3-ethanamine, 5-fluoro-7-methoxy-1H-indole-3-ethanamine, 2-methyl-5-nitro-7-chloro-1H-indole-3-ethanamine, 2-ethyl-7-fluoro-1H-indole-3-ethanamine, 2-methyl-7-fluoro-N-dimethyltryptamine, 7-chloro-N-methyltryptamine, 5-chloro-7-methyl-N-ethyltryptamine, 6-(1-propenyl)-7-methoxy-N-methyltryptamine, 6-dimethylamino-7-ethoxy-N-methyltryptamine, 6-(2-butenyl)-7-ethoxy-1H-indole-3-ethanamine, 4,7-dichloro-1H-indole-3-ethanamine, 5-methylamino-7-propyl-1H-indole-3-ethanamine, 5-methoxy-7-ethoxy-1H-indole-3-ethanamine, 6-thiomethyl-7-fluoro-1H-indole-3-ethanamine, 5-chloromethyl-7-chloro-1H-indole-3-ethanamine, 5-cyclohexyl-7-methyl-1H-indole-3-ethanamine, 5-benzyl-7-bromo-1H-indole-3-ethanamine, 5-cyclopropylmethyl-7-fluoro-1H-indole-3-ethanamine, 6-bromoethyl-7-bromo-1H-indole-3-ethanamine, 6-(chloro-1-propenyl)-7-ethyl-1H-indole-3-ethanamine, 6-(2-cyclohexenyl)-7-fluoro-1H-indole-3-ethanamine, 2-methyl-5-methyl-7-chloro-N-methyltryptamine, and 2-methyl-7-chloro-N-methyltryptamine.

The present invention contemplates racemic mixtures as well as the substantially pure stereoisomers of the compounds of Formulas I, V, VI, and VII. The term "enantiomer" is used herein as commonly used in organic chemistry to denote a compound which rotates the plane of polarization. Thus, the "– enantiomer" rotates the plane of polarized light to the left, and contemplates the levorotary compound of Formulas I and V. The + and − enantiomers can be isolated using well-known classical resolution techniques. One particularly useful reference which describes such methods is JACQUES et. al. ENANTIOMERS, RACEMATES, AND RESOLUTIONS (John Wiley and Sons 1981). Appropriate resolution methods include direct crystallization, entrainment, and crystallization by optically active solvents. Chrisey, L. A. *Heterocycles*, 267:30 (1990). A preferred resolution method is crystallization with an optically active acid or by chiral synthesis as described in Example 46 using the method of A. I. Meyers. Loewe, M. F. et al., *Tetrahedron Letters*, 3291:26 (1985), Meyers, A. I. et al., *J. Am. Chem. Soc.*, 4778:110 (1988). Preferred optically active acids include camphorsulfonic and derivatives of tartaric acid.

The present invention encompasses both the R and the S configurations. The terms "R" and "S" are used herein as commonly used in organic chemistry to denote the specific configuration of a chiral center. See, R. T. Morrison and R. N. Boyd, *Organic Chemistry*, pp 138–139 (4th Ed. Allyn & Bacon, Inc., Boston) and Orchin, et al. *The Vocabulary of Organic Chemistry*, p. 126, (John Wiley and Sons, Inc.).

For example, the present invention includes, but is not limited to, compounds such as (−)-(S)-7-methyl-8-bromo-1-[(3,4-dimethoxyphenyl)methyl]-1,2,3,4-tetrahydro-9H-pyrido[3,4-b]indole; (−)-(S)-5,7-dimethyl-1,2,3,4-tetrahydro-1-[(3,4-dimethoxyphenyl)methyl]-9H-pyrido[3,4-b]indole; (−)-(S)-5-fluoro-6-methyl-1-[(2-chloro-3,4-dimethoxyphenyl)methyl]-1,2,3,4-tetrahydro-9H-pyrido[3,4-b]indole; and (−)-(S)-6-methyl-1,2,3,4-tetrahydro-1-[(3,4-dimethylphenyl)methyl]-9H-pyrido[3,4-b]indole. The invention also includes, but is not limited to, (+)-(S)-7-methyl-8-bromo-1-[(3,4-dimethoxyphenyl)methyl]-1,2,3,4-tetrahydro-9H-pyrido [3,4-b]indole; (+)-(S)-5,7-dimethyl-1,2,3,4-tetrahydro-1-[(3,4-dimethoxyphenyl)methyl]-9H-pyrido[3,4-b]indole; (+)-(S)-5-fluoro-6-methyl-1-[(2-chloro-3,4-dimethoxyphenyl)methyl]-1,2,3,4-tetrahydro-9H-pyrido[3,4-b]indole; (−)-(R)-7-methyl-8-bromo-1-[(3,4-dimethoxyphenyl)methyl]-1,2,3,4-tetrahydro-9H-pyrido[3,4-b]indole; (−)-(R)-5,7-dimethyl-1,2,3,4-tetrahydro-1-[(3,4-dimethoxyphenyl)methyl]-9H-pyrido[3,4-b]indole; (−)-(R)-5-fluoro-6-methyl-1-[(2-chloro-3,4-dimethoxyphenyl)methyl]-1,2,3,4-tetrahydro-9H-pyrido[3,4-b]indole; and (−)-(R)-6-methyl-1,2,3,4-tetrahydro-1-[(3,4-dimethylphenyl)methyl]-9H-pyrido[3,4-b]indole; (+)-(R)-7-methyl-8-bromo-1-[(3,4-dimethoxyphenyl)methyl]-1,2,3,4-tetrahydro-9H-pyrido[3,4-b]indole; (+)-(R)-5,7-dimethyl-1,2,3,4-tetrahydro-1-[(3,4-dimethoxyphenyl)methyl]-9H- pyrido[3,4-b]indole; (+)-(R)-5-fluoro-6-methyl-1-[(2-chloro-3,4-dimethoxyphenyl)methyl]-1,2,3,4-tetrahydro-9H-pyrido[3,4-b]indole; and (+)-(S)-6-methyl-1,2,3,4-tetrahydro-1-[(3,4-dimethylphenyl)methyl]-9H-pyrido[3,4-b]indole.

The compounds of the present invention are known to form hydrates and solvates with appropriate solvents. Preferred solvents for the preparation of solvate forms include water, alcohols, tetrahydrofuran, DMF, and DMSO. Preferred alcohols are methanol and ethanol. Other appropriate solvents may be selected based on the size of the solvent molecule. Small solvent molecules are preferred to facilitate the corresponding solvate formation. The solvate or hydrate is typically formed in the course of recrystallization or in the course of salt formation. One useful reference concerning solvates is Sykes, Peter, A Guidebook to Mechanism in Organic Chemistry, 6:56 (1986, John Wiley & Sons, New York). The term "solvate" as used herein includes hydrate forms such as monohydrate and dihydrates.

The compounds of the present invention can be prepared using chemical processes that are understood in the art; however, the most preferred method for preparing the formula (I) compounds of this invention utilizes the process of Scheme V. The most preferred method for preparing a compound of Formula VI or VII is illustrated in Scheme II infra. Compounds wherein $R_9$ and/or $R_{10}$ are not hydrogen can be prepared by art recognized methods including direct alkylation or reductive alkylation of the corresponding tryptamine. Compounds wherein $R_{12}$ is $C_1$-$C_3$ alkyl can be prepared using understood reductive alkylation methods.

A compound of formula I, wherein $R_2$ is hydrogen, may be prepared by contacting a lactone compound of formula (i) with an amine of formula (h) in the presence of a protic acid. This Pictet-Spengler type reaction is generally applicable, provides desirable yields, and produces stable intermediates. Further, the product of the reaction typically may be directly isolated as the desired salt.

The compounds of formula (a) which may be used as starting materials for the compounds of the instant invention can be purchased from art-recognized vendors or may be prepared using well-known chemical techniques. The compounds of formula (b) which are useful as starting materials for the compounds of this invention may be prepared as represented by Scheme I. The $R_4$ group is as defined herein above.

The process for preparing the compounds of this invention will be discussed in greater detail in the following paragraphs.

Scheme I

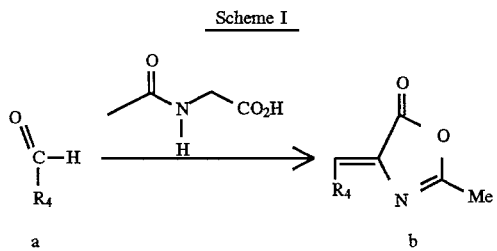

Compound (a) in Scheme I may be substituted or unsubstituted depending on the desired product. Most formula (a) compounds necessary for the preparation of the azalactone (b) starting materials are commercially available. Additional substituted formula (a) compounds may prepared using common chemical methods. Furniss, B. S. et al., Vogel's Textbook of Practical Organic Chemistry (John Wiley, New York, N.Y. 1989) see especially pp 989 through 993.

Generally, the Scheme I reaction is begun by preparing a solution of compound (a), acetylglycine and sodium acetate in acetic anhydride. The reaction is commonly heated from about 90° C. to about 110° C. for a period of about 2–15 hours. The reaction mixture is cooled to about ambient temperature and stirred for a period of about 0–10 hours under inert conditions. The reaction time will vary depending on the degree of substitution on the $R_4$ group and the completion of reaction desired.

When the reaction is complete, the mixture is poured onto ice with stirring. The azalactone (b) may be isolated by standard isolation techniques such as filtration and may be dried under reduced pressure.

Compound (d) in Scheme II is used as a starting material for compounds of formula (I). These compounds are commercially available or may be prepared using the well-known Fischer indole synthesis applied to tryptamines. The Fischer synthesis is represented by Scheme II. "A" is as hereinabove defined.

Scheme II

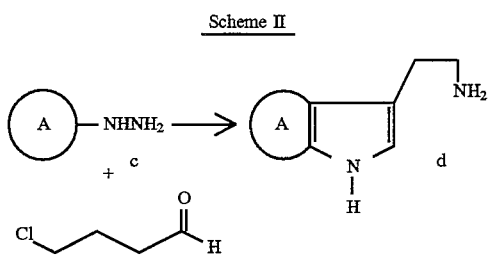

The chlorobutanal compound used in Scheme II may be prepared through the hydrogenation of chlorobutyryl chloride. Other halobutanal compounds may be suitable for the Scheme II hydrogenation. The hydrogenation may be facilitated by the use of a catalyst such as Pd/C. The starting compounds (c) in Scheme III may be purchased or prepared using known methods. March, J., Advanced Organic Chemistry Reactions, Mechanisms, and Structure, 3rd (John Wiley & Sons, New York, 1985) see especially page 1163.

The Fischer synthesis is commonly begun by adding a suitable saturated base like sodium carbonate to a stirred suspension of the hydrazine salt in an organic solvent like chloroform. The hydrazine hydrochloride salt is one especially preferred hydrazine salt. The desired hydrazine free base is extracted with the organic phase. The oil is placed in an alcohol and water solution and treated with an appropriate base like sodium acetate. The halobutanal is added and the tube purged with an inert gas like nitrogen. The resulting mixture is placed in an oil bath which has been heated to about 90° C.–110° C. The mixture should be heated for about 17 to 19 hours. The mixture is allowed to cool to ambient temperature and is concentrated under reduced pressure. The residue is partitioned between a suitable organic and basic aqueous phase, such as chloroform/methanol and aqueous sodium carbonate. The organic phase may be concentrated and the resulting compound (d) purified by standard methods such as flash chromatography. If chromatography is used, fractions containing product may be combined and concentrated. The oil is dissolved in an appropriate solvent, such as diethyl ether containing about 1% alcohol. A preferred alcohol is methanol. The mixture may be treated with dry acid gas, such as dry HCl gas to produce the corresponding acid addition salt of the desired compound (d).

One method for preparing Formula (I) compounds uses the Pictet-Spengler reaction as represented by Scheme III. The substituents are as defined hereinabove.

Scheme III

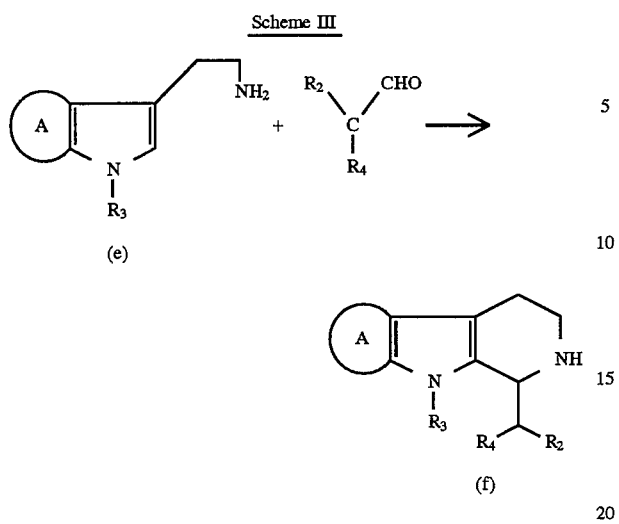

Generally, the Scheme III reaction is carried out by refluxing compound (e) with the selected aldehyde in a suitable solvent such as ethanol or methanol for a period of about 35 to 50 hours. The precipitated reaction product (f) is collected by common isolation methods, such as filtration and may be purified by recrystallization. If a compound with an $R_1$ substituent is desired, the reaction may be followed by a reductive alkylation. The reductive alkylation is represented by Scheme IV.

Scheme IV

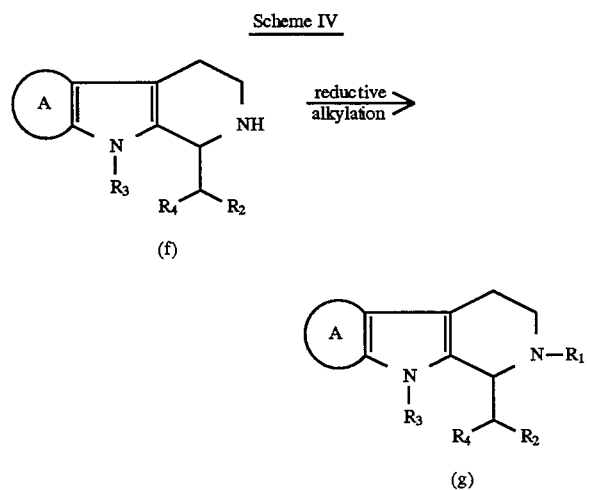

A protic acid and aldehyde solution is commonly added to an aqueous solution of compound (f). The most preferred protic acid is formic acid. The most preferred aldehyde is formaldehyde. The artisan can readily choose other appropriate reagents to facilitate the reductive alkylation. The resulting solution is refluxed for a period of about 4 to 80 hours. After reflux the solution should be made basic using an appropriate base such as potassium carbonate. The desired product can then be extracted with an appropriate organic phase, such as chloroform. The product can be dried, concentrated, and purified by known methods such as flash chromatography.

A preferred method for preparing Formula (I) compounds, wherein $R_2$ is hydrogen, utilizes the modified Pictet-Spengler reaction described supra, as represented by Scheme V. The substituents are as defined hereinabove.

Scheme V

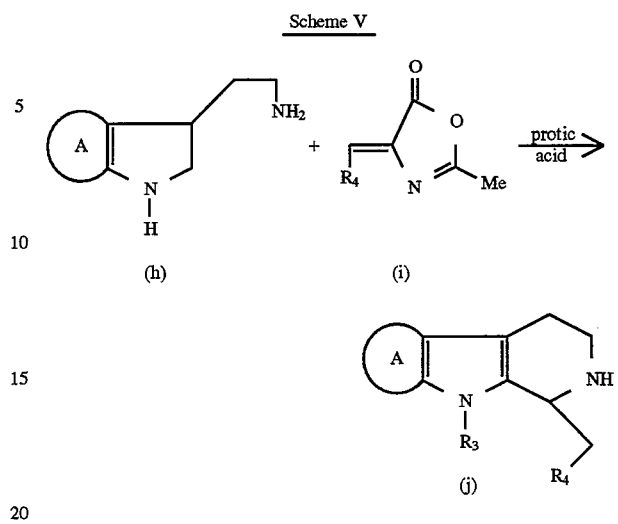

Compound (h) and compound (i) are contacted in a suitable protic aqueous acid solution. This step may be completed under inert conditions. Compound (h) and compound (i) may be refluxed under atmospheric or inert conditions for a period of about 20 to about 30 hours. Preferred protic acids include sulfuric acid and hydrochloric acid. The most preferred acid solution is 1N HCl. If direct isolation is not effective, then the reaction mixture may be neutralized with an appropriate base, such as potassium carbonate, followed by extraction with an organic phase, such as chloroform. The product can be isolated through solvent removal followed by chromatographic isolation, such as silica gel chromatography, or other common isolation techniques. Typically the product is isolated as the acid addition salt. Appropriate salt forms are discussed supra.

As noted above, the compounds of the present invention can exist as resolved enantiomers. The single (−)enantiomer may be prepared by the chemical resolution method of A. I. Meyers as represented by Scheme VI infra. The (+)enantiomer may be prepared using known resolution techniques described supra. All substituents are as defined hereinabove.

Scheme VI

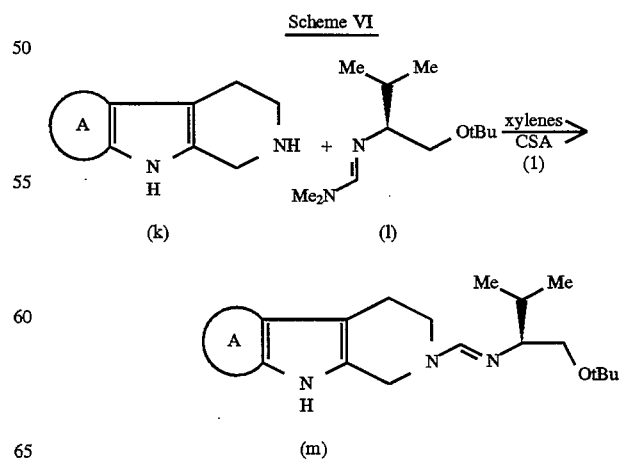

-continued
Scheme VI

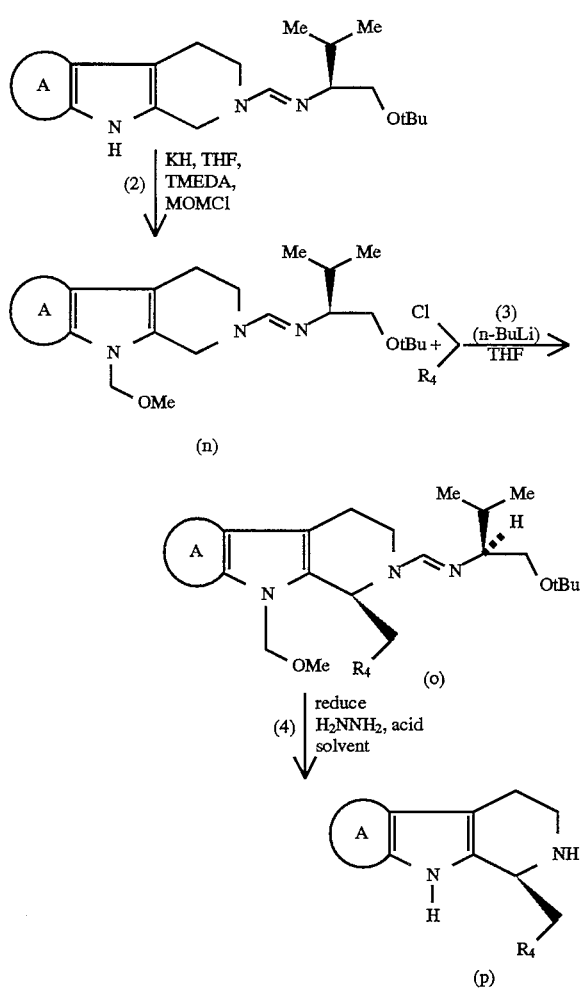

In Scheme VI, CSA represents camphorsulfonic acid. Butylformadine (1) is prepared from the amino acid valine using known methods. Other formadine compounds will also work. In step 1, the compound (k) and butylformadine (1) solution is refluxed for a period of about 70 to 80 hours.

The product of the reflux reaction can be purified by standard isolation methods, such as flash chromatography. The isolated oil can be used without further purification.

Compound (m) prepared in step 1, can be added to a suspension of potassium hydride (KH) in tetrahydrofuran (THF). Tetramethylethylenediamine (TMEDA) and then chloromethylmethyl ether (MOMCl) are added to the solution, as represented by step 2. The mixture is stirred for a period of about 1 hour. The mixture can be treated with water and partitioned between an appropriate organic, such as diethyl ether, and water. The product should be extracted with the organic phase, dried over potassium carbonate, and concentrated. The resulting oil may be used in subsequent steps without further purification.

In step 3, n-BuLi is slowly added dropwise to a stirred, cooled (about −76° C. to −80° C.) solution of the formadine in dry THF. The solution is stirred for a period of about 1 hour followed by addition of the chloro compound in dry THF. The solution is stirred for an additional period of about 4–5 hours at the reduced temperature. The mixture is allowed to cool to room temperature for a period of about 4 to 14 hours. Wet THF is added and the solution concentrated. The residue is dissolved in an appropriate organic solvent such as chloroform and washed with water. The organic phase is dried over a suitable drying agent, such as sodium carbonate, and concentrated to facilitate purification of the desired product. The product may be isolated by flash chromatography and concentrated. The resulting oil may be used in subsequent steps without further purification.

The deprotection reaction represented in step 4 is begun at reduced temperature (about 0° C.). Water, acetic acid, and hydrazine hydrate are added to compound (o). The reaction temperature is decreased to about −10° C. to −20° C. for a period of about 60–120 hours. The mixture is allowed to warm to ambient temperature and is concentrated. The product is dissolved in an appropriate organic phase, such as chloroform, and washed with water. The organic phase is dried over a suitable drying agent, such as sodium carbonate, and concentrated to a viscous oil. The oil is dissolved in an appropriate solvent, such as diethyl ether and treated with a suitable organic or inorganic acid to afford the desired acid addition salt. The salt can be isolated and purified by common chemical methods.

If the desired product has an alkyl group at the $R_3$ position, the reaction represented by Scheme VII may be employed.

Scheme VII

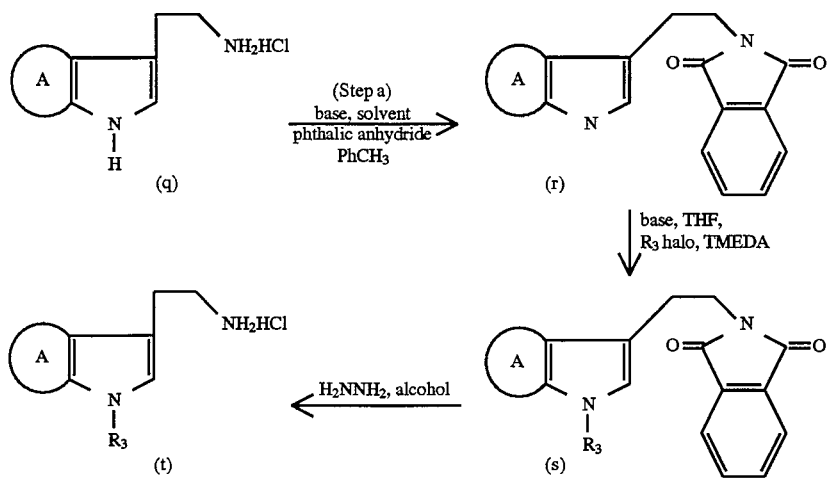

In Scheme VII, an appropriate saturated base solution, such as sodium carbonate, is added to compound (q). The desired compound (q) salt may be prepared by the method of Scheme II, above. The mixture is stirred at about ambient temperature for a period of about 1 hour. The layers are separated, and the aqueous layer is extracted with an appropriate organic solvent, such as chloroform. The organic layers are dried over an appropriate drying agent, such as sodium sulfate, and concentrated. The residue is dissolved in a suitable solvent such as toluene and treated with phthalic anhydride. The solution is refluxed for a period of about 12 to 20 hours with azeotropic drying. The solution is cooled, concentrated, and recrystallized to give compound (r).

In the next step, compound (r) is mixed in THF. A cooled (about 0° C.) suspension of an appropriate base, such as potassium hydride in dry THF, is slowly added to the compound (r) solution. After the addition of the the base, the mixture is stirred for a period of about 1 hour. Tetramethylethylenediamine (TMEDA) is added, followed by a haloalkyl such as methyl iodide (MeI). After about 1 hour, the reaction is quenched by the addition of water, followed by extraction with an appropriate organic phase, such as diethyl ether. The organic phases are dried over an appropriate drying agent, such as magnesium sulfate and concentrated.

The solution of the concentrated compound (s) can be used directly in the next step. It is contacted with an appropriate solvent, such as methanol, and treated with hydrazine. The mixture is refluxed for a period of about 2 hours. The mixture is cooled to ambient temperature and treated with concentrated acid, such as HCl. The mixture is then treated with an alcohol and refluxed for a period of about 12 to 20 hours. Preferred alcohols include methanol, ethanol, and butanol. After cooling to ambient temperature, the mixture is partitioned between a suitable organic and an aqueous phase. One suitable combination is chloroform and concentrated sodium carbonate solution. The aqueous layer may be further extracted, the organic phases combined, dried, and concentrated. The product may be purified by flash chromatography, concentrated, and converted to a desired salt. The resulting compound (t) may be used in Scheme III or Scheme V to produce the desired Formula (I) compound.

The following Examples further illustrate the preparation of certain of the Formula (I) compounds. The examples are illustrative only, and are not intended to limit the scope of the invention.

The column chromatography procedures used standard flash chromatography techniques. One well-known reference describing appropriate flash chromatography techniques is Still, W. C. Kahn, and Mitra, *J. Org. Chem.*, 43, 2932, (1978). Fractions containing product were generally evaporated under reduced vacuum to provide the product.

Optical rotations were obtained using methanol, pyridine, or other suitable solvent.

The hydrochloride salt of the particular compound was prepared by placing the free base into diethyl ether containing an alcohol such as methanol or other suitable solvent mixture. While stirring this ether solution, a solution of HCl in diethyl ether was added dropwise until the solution became acidic. Alternatively, the ether solution was treated with dry HCl gas.

The maleate salt of the particular compound was prepared by placing the free base in ethyl acetate or other suitable solvent and treating with maleic acid. The precipitate formed was filtered and dried to provide the corresponding hydrochloride or maleate salt of the free base.

PREPARATION 1

Preparation of 4-chlorobutanal

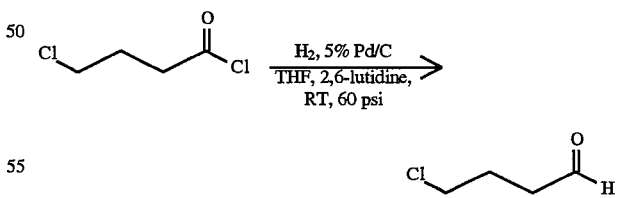

4-Chlorobutyryl chloride (300 g, 2.13 mol.) was dissolved in dry THF (3 L). To this solution was added 2,6-lutidine (252 mL) followed by 5% Pd/C (30 g). This mixture was placed in a Parr hydrogenator and shaken under 60 psi of hydrogen for 6 hours. The mixture was purged with nitrogen, filtered, washing the catalyst with THF (500 mL), and concentrated at room temperature under reduced pressure. Distillation afforded 4-chlorobutanal (148.3 g) as a colorless liquid.

EXAMPLE 1

Preparation of 8-methyl-1-[(3,4-dimethoxyphenyl)methyl]-1,2,3,4-tetrahydro-9H-pyrido[3,4-b]indole

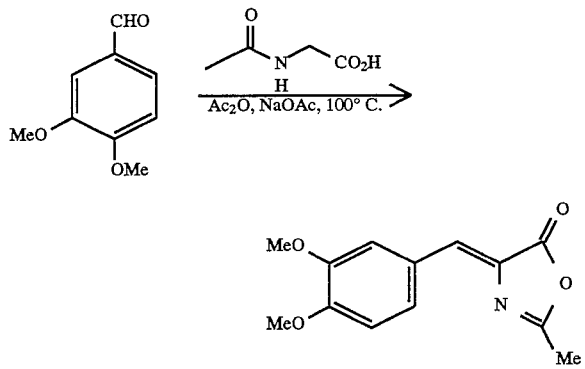

A solution of 3,4-dimethoxybenzaldehyde (24.5 g, 0.15 mol.), N-acetylglycine (17.4 g, 0.15 mol.) and sodium acetate (12.1 g, 0.15 mol) in acetic anhydride (135 mL) was heated to 100° C. for 12 hours. The reaction mixture was cooled to ambient temperature poured onto ice (300 mL) with stirring. The product was isolated by filtration, washed with water (3×50 mL) and diethyl ether (3×50 mL) and dried under reduced pressure (16.3 g).

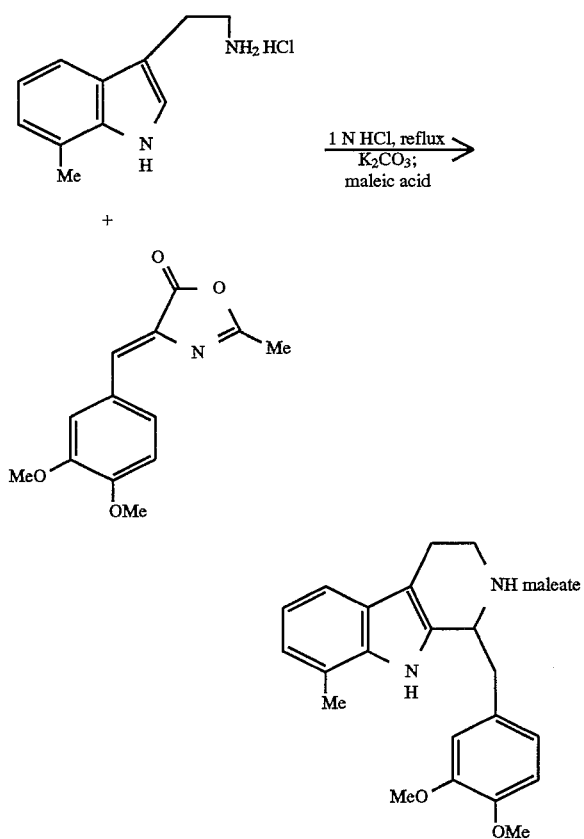

A suspension of azalactone prepared above (1.35 g, 5.46 mmol.) and 7-methyl-tryptamine hydrochloride (1.15 g, 5.46 mmol.) in 1N HCl (50 mL) was heated to reflux for 24 hours under nitrogen atmosphere. The reaction mixture was cooled to ambient temperature neutralized with saturated aqueous potassium carbonate solution and extracted with chloroform. The combined organic layers were concentrated under reduced pressure and the residue chromatographed on silica gel (ethyl acetate/0.2% NH$_4$OH as eluent). The fractions containing product were pooled and concentrated under reduced pressure. The residue was dissolved in ethyl acetate containing 1% methanol and treated with maleic acid. The product was isolated as the maleate salt (730 mg) by filtration. (mp=168° C., dec.)

| Analysis | Calculated | Found |
| --- | --- | --- |
| C | 66.36 | 66.15 |
| H | 6.24 | 6.28 |
| N | 6.19 | 5.79 |

EXAMPLE 2

Preparation of 8-bromo-1-[(3,4-dimethoxyphenyl)methyl]-1,2,3,4-tetrahydro-9H-pyrido[3,4-b]indole hydrochloride

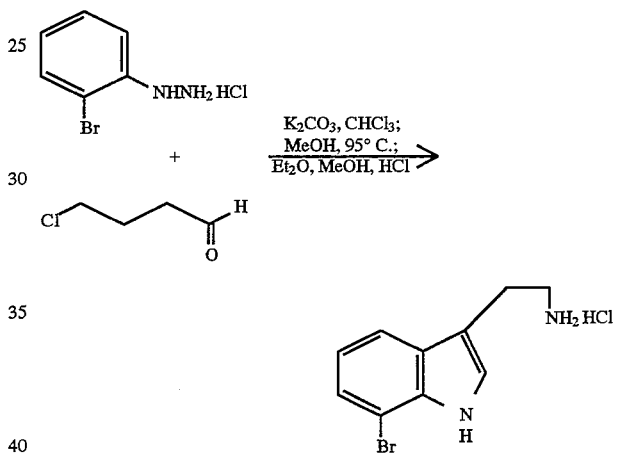

To a stirred suspension of 2-bromophenyl-hydrazine hydrochloride (25.8 g, 115 mmol.) in chloroform (500 mL) was added saturated sodium carbonate solution (500 mL). The mixture was stirred for 30 minutes and extracted with chloroform (2×200 mL). The combined organic phases were concentrated to afford the hydrazine free base as a yellow oil. This oil was dissolved in methanol (100 mL) and treated slowly with 4-chlorobutanal (12.3 g, 115 mmol). The mixture was placed in a sealable tube and purged with nitrogen for 10 minutes. The tube was sealed and placed in an oil bath preheated to 95° C. Heating was continued for 18 hours. The resulting dark solution was cooled to ambient temperature and concentrated under reduced pressure. The residue was partitioned between chloroform/methanol (75/25 by volume) and aqueous sodium carbonate solution. The organic phase was concentrated and the crude indole ethanamine was purified by flash chromatography on silica gel (0–25% methanol gradient in chloroform as eluent). Fractions containing product were combined and concentrated. The oil was dissolved in diethyl ether (300 mL) containing 1% methanol and treated with dry HCl gas. The hydrochloride salt was isolated by filtration, washed with 2-propanol (50 mL) and diethyl ether (100 mL) and dried to afford 7-bromotryptamine hydrochloride (3.6 g) as a pale solid, which was used without further purification.

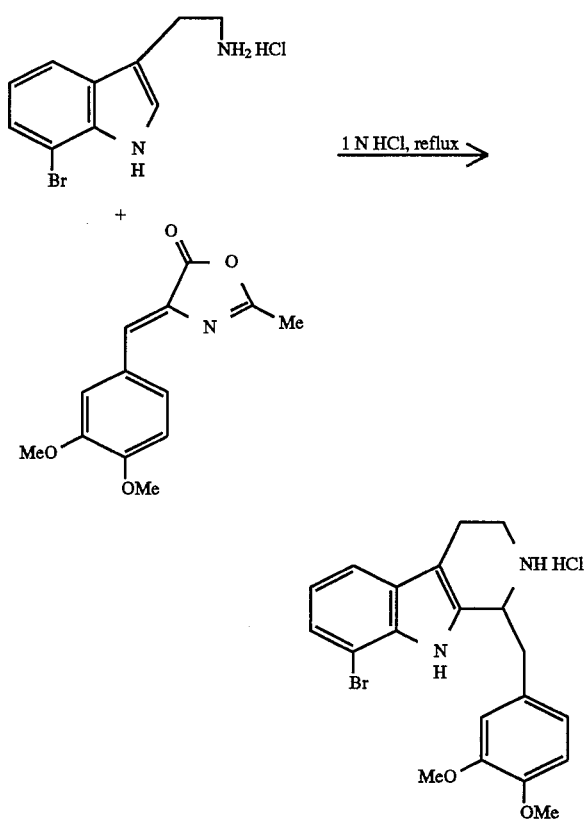

A suspension of azalactone (prepared as described in Example 1) (1.16 g, 4.7 mmol.) and 7-bromotryptamine hydrochloride (1.0 g, 3.6 mmol.) in 1N HCl (100 mL) was heated to reflux for 24 hours under nitrogen atmosphere. The reaction mixture was cooled to ambient temperature and the crude product isolated by filtration. The brown solid was triturated with isopropyl alcohol (3×50 mL) and washed with diethyl ether (3×50 mL). Recrystallization from ethanol afforded 860 mg of desired product as the hydrochloride salt. (mp=279°–281° C., dec.)

| Analysis | Calculated | Found |
| --- | --- | --- |
| C | 54.87 | 54.75 |
| H | 5.07 | 5.20 |
| N | 6.40 | 6.23 |

EXAMPLE 3

Preparation of 6,8-dibromo-1-[(3,4-dimethoxyphenyl)methyl]-1,2,3,4-tetrahydro-9H-pyrido[3,4-b]indole

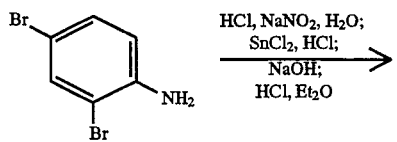

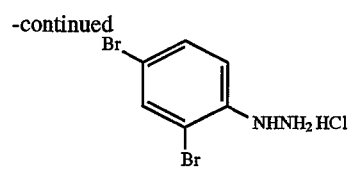

To a stirred, cooled (−5° C.) solution of 2,4-dibromoaniline (50.0 g, 0.2 mol.) in concentrated HCl solution (110 mL) was added sodium nitrite (13.8 g, 0.2 mol.) in water (110 mL) dropwise at such a rate as to maintain temperature below 5° C. After complete addition, the mixture was further stirred at 5° C. for 30 minutes. A solution of tin chloride monohydrate (135.4 g, 0.6 mol.) in concentrated HCl (total volume 170 mL) was added dropwise again maintaining temperature below 5° C. After complete addition and 30 minutes of further stirring, the mixture was placed in the freezer overnight. The light brown solid which precipitated was isolated by filtration and washed with cold brine followed by a solution of petroleum ether/diethyl ether (2/1 by volume). This solid was slowly added to an ice cooled mixture of 50% sodium hydroxide solution/ethyl acetate. The mixture was extracted with ethyl acetate and the organic phase dried over magnesium sulfate. After filtration, the solution was concentrated to 400 mL total volume, diluted with diethyl ether (1.5 L) and treated with dry HCl. The product, 2,4-dibromophenyl-hydrazine hydrochloride (45.9 g) was isolated as a white solid and used without further purification.

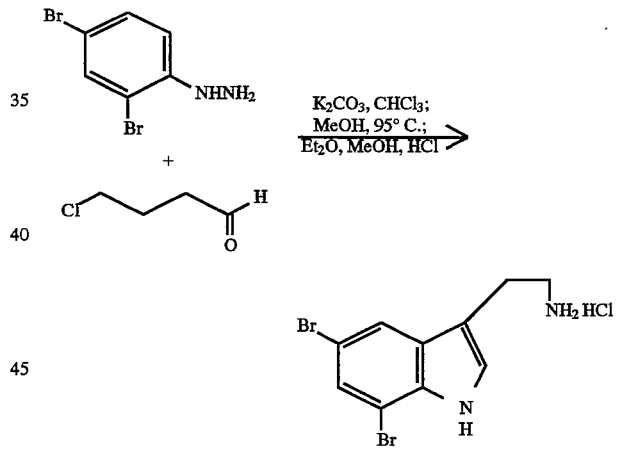

To a stirred suspension of 2,4-dibromophenyl-hydrazine hydrochloride (22.0 g, 83 mmol.) in chloroform (500 mL) was added saturated potassium carbonate solution (500 mL). The mixture was stirred for 30 minutes and extracted with chloroform (2×200 mL). The combined organic phases were concentrated to afford the hydrazine free base as a yellow oil. This oil was dissolved in methanol (163 mL) and treated slowly with 4-chlorobutanal (8.8 g, 83 mmol.). The mixture was placed in a sealable tube and purged with nitrogen for 10 minutes. The tube was sealed and placed in an oil bath preheated to 95° C. Heating was continued for 18 hours. The resulting dark solution was cooled to ambient temperature and concentrated under reduced pressure. The residue was partitioned between chloroform/methanol (75/25 by volume) and aqueous sodium carbonate solution. The organic phase was concentrated and the crude indole ethanamine was purified by flash chromatography on silica gel (0–25% methanol gradient in chloroform as eluent). Fractions containing product were combined and concentrated. The oil was dissolved in diethyl ether (300 mL) containing 1% methanol and treated with dry HCl gas. The hydrochloride salt was isolated by filtration, washed with 2-propanol (50 mL) and diethyl ether (100 mL) and dried to afford 7-bromotryptamine hydrochloride (1.5 g) as a pale solid, which was used without further purification.

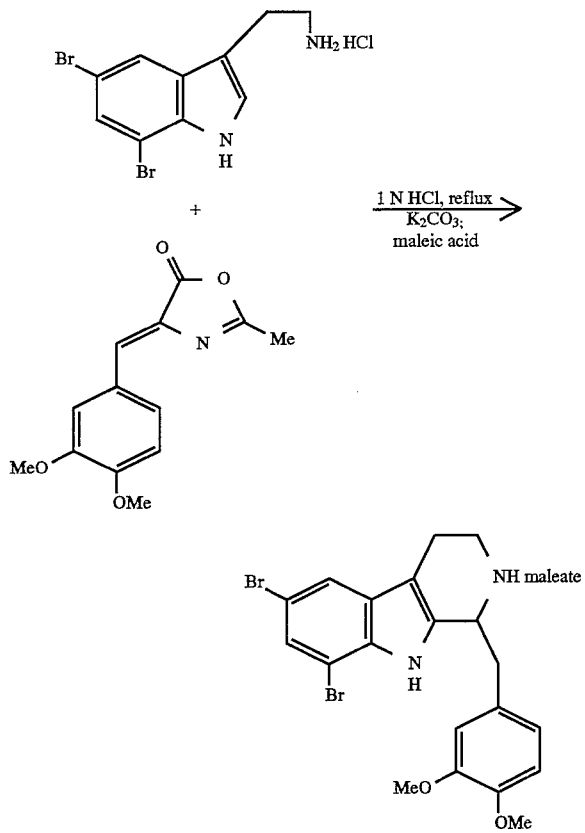

A suspension of azalactone (prepared as described in Example 1) (0.45 g, 1.82 mmol.) and 5,7-dibromotryptamine hydrochloride (0.58 g, 1.64 mmol.) in 1N HCl (65 mL) was heated to reflux for 24 hours under nitrogen atmosphere. The reaction mixture was cooled to ambient temperature, neutralized with saturated aqueous potassium carbonate solution and extracted with chloroform. The combined organic layers were concentrated under reduced pressure and the residue chromatographed on silica gel (ethyl acetate/0.2% NH$_4$OH as eluent). The fractions containing product were pooled and concentrated under reduced pressure. The residue was dissolved in ethyl acetate containing 1% methanol and treated with maleic acid. The product was isolated as the maleate salt (340 mg) by filtration. (mp=177°–179° C., dec.)

| Analysis | Calculated | Found |
|---|---|---|
| C | 48.34 | 48.61 |
| H | 4.06 | 4.17 |
| N | 4.70 | 4.69 |

EXAMPLE 4

Preparation of 6-methyl-8-bromo-1-[(3,4-dimethoxyphenyl)-methyl]-1,2,3,4-tetrahydro-9H-pyrido[3,4-b]indole hydrochloride

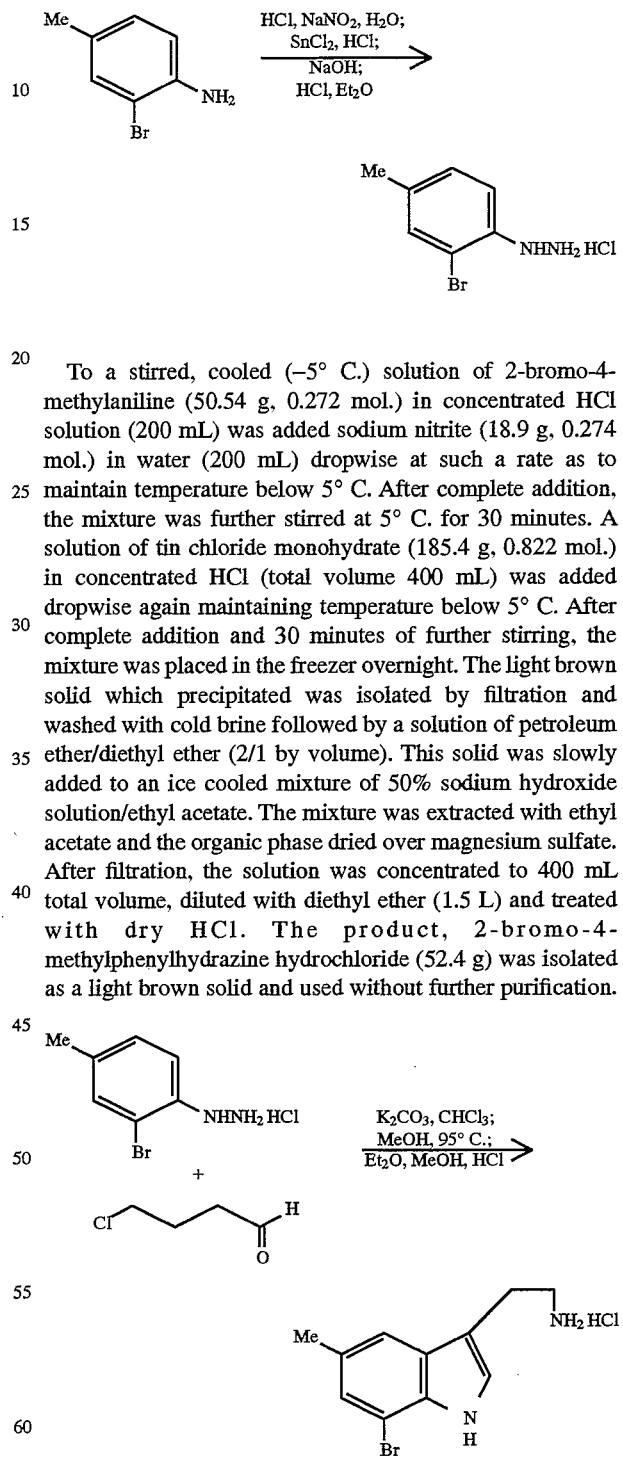

To a stirred, cooled (–5° C.) solution of 2-bromo-4-methylaniline (50.54 g, 0.272 mol.) in concentrated HCl solution (200 mL) was added sodium nitrite (18.9 g, 0.274 mol.) in water (200 mL) dropwise at such a rate as to maintain temperature below 5° C. After complete addition, the mixture was further stirred at 5° C. for 30 minutes. A solution of tin chloride monohydrate (185.4 g, 0.822 mol.) in concentrated HCl (total volume 400 mL) was added dropwise again maintaining temperature below 5° C. After complete addition and 30 minutes of further stirring, the mixture was placed in the freezer overnight. The light brown solid which precipitated was isolated by filtration and washed with cold brine followed by a solution of petroleum ether/diethyl ether (2/1 by volume). This solid was slowly added to an ice cooled mixture of 50% sodium hydroxide solution/ethyl acetate. The mixture was extracted with ethyl acetate and the organic phase dried over magnesium sulfate. After filtration, the solution was concentrated to 400 mL total volume, diluted with diethyl ether (1.5 L) and treated with dry HCl. The product, 2-bromo-4-methylphenylhydrazine hydrochloride (52.4 g) was isolated as a light brown solid and used without further purification.

5-Methyl-7-bromotryptamine hydrochloride (4.95 g) was prepared as described in Example 3, except using 2-bromo-4-methylphenyl hydrazine hydrochloride (21 g) as starting material.

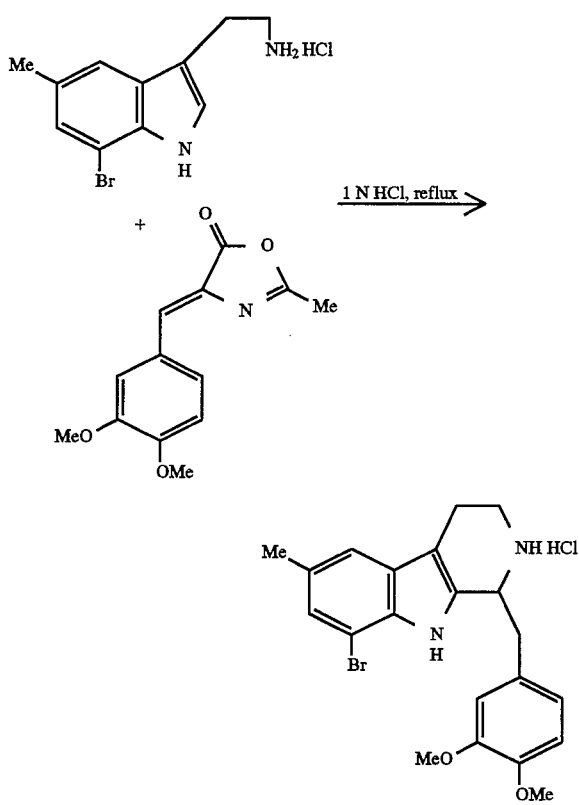

A suspension of azalactone (prepared as described in Example 5) (1.44 g, 6.07 mmol.) and 5-methyl-7-bromotryptamine hydrochloride (1.12 g, 3.87 mmol.) in 1N HCl (80 mL) was heated to reflux for 24 hours under nitrogen atmosphere. The reaction mixture was cooled to ambient temperature and the crude product isolated by filtration. The brown solid was triturated with isopropyl alcohol (3×50 mL) and washed with diethyl ether (3×50 mL). Recrystallization from ethanol afforded 1.06 g of desired product as a pale solid. (mp=251°–253° C., dec.)

| Analysis | Calculated | Found |
|---|---|---|
| C | 55.83 | 56.08 |
| H | 5.35 | 5.32 |
| N | 6.20 | 6.33 |

EXAMPLE 5

Preparation of 8-methoxy-1-[(3,4-dimethoxyphenyl)methyl]-1,2,3,4-tetrahydro-9H-pyrido[3,4-b]indole

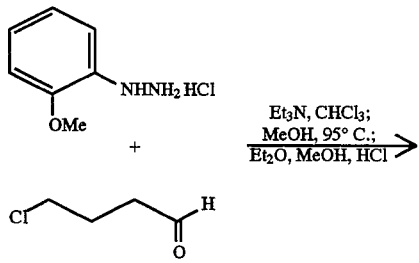

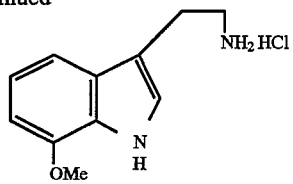

To a stirred, cooled (0° C.) suspension of 2-methoxyphenylhydrazine hydrochloride (14.44 g, 83 mmol.) in THF (600 mL) was added 4-chlorobutanal (9.0 g, 84 mmol.) followed by dropwise addition of triethylamine (8.6 g, 85 mmol.) in THF (20 mL). Upon complete addition, the cooling bath was removed and the solution stirred for 1 hour. The reaction mixture was filtered and the filter cake washed with THF (100 mL). The combined filtrates were concentrated to an orange oil, which was dissolved in methanol (150 mL) and water (5 mL). The solution was transferred to a sealable tube and purged with nitrogen for 10 minutes. The tube was sealed and placed in an oilbath preheated to 95° C. After heating for 14 hours, the reaction mixture was cooled to ambient temperature and concentrated under reduced pressure. The residue was partitioned between saturated aqueous potassium carbonate and 3:1 chloroform: 2-propanol. The organic phase was dried over sodium sulfate and concentrated. The residue was purified by flash chromatography on silica gel (15% methanol, 0.2% NH$_4$OH, in chloroform as eluent). The fractions containing product were pooled and concentrated under reduced pressure. The residue was dissolved in methanol and treated with dry HCl and concentrated to afford 7-methoxytryptamine hydrochloride (4.04 g) as a stable foam, which was used without further purification.

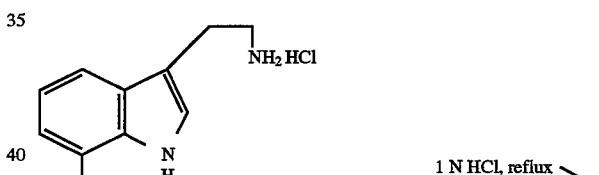

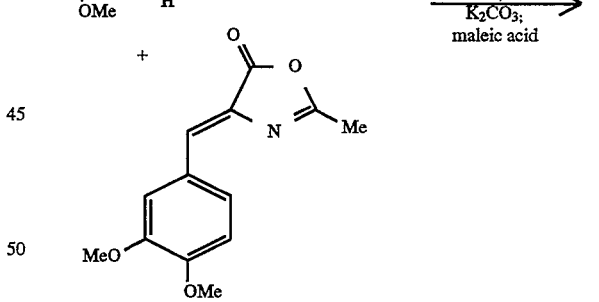

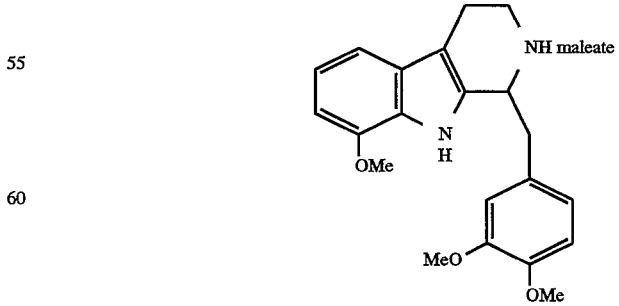

A suspension of azalactone (prepared as described in Example 1) (1.20 g, 4.85 mmol.) and 7-methoxytryptamine hydrochloride (1.0 g, 4.4 mmol.) in 1N HCl (120 mL) was heated to reflux for 24 hours under nitrogen atmosphere. The reaction mixture was cooled to ambient temperature, neutralized with saturated aqueous potassium carbonate solution and extracted with chloroform. The combined organic layers were concentrated under reduced pressure and the residue chromatographed on silica gel (ethyl acetate/0.2% NH$_4$OH as eluent). The fractions containing product were pooled and concentrated under reduced pressure. The residue was dissolved in ethyl acetate containing 1% methanol and treated with maleic acid. The product was isolated as the maleate salt (770 mg) by filtration. (mp=219°–220° C., dec.).

| Analysis | Calculated | Found |
|---|---|---|
| C | 64.09 | 64.04 |
| H | 6.02 | 6.18 |
| N | 5.98 | 5.93 |

EXAMPLE 6

Preparation of 6,8-difluoro-1-[(3,4-dimethoxyphenyl)-methyl]-1,2,3,4-tetrahydro-9H-pyrido[3,4-b]indole

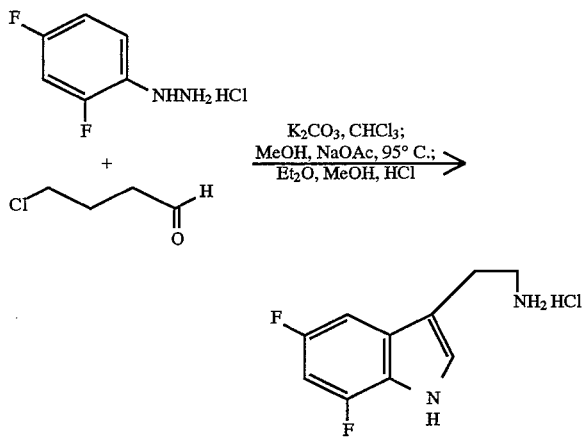

To a stirred suspension of 2,4-difluoro-phenylhydrazine hydrochloride (18.5 g, 128 mmol.) in chloroform (500 mL) was added saturated potassium carbonate solution (500 mL). The mixture was stirred for 30 minutes and extracted with chloroform (2×200 mL). The combined organic phases were concentrated to afford the hydrazine free base as a yellow oil. This oil was dissolved in a solution of methanol (163 mL), water (36 mL) and sodium acetate (10.57 g) and treated slowly with 4-chlorobutanal (13.7 g, 128 mmol.). The mixture was placed in a sealable tube and purged with nitrogen for 10 minutes. The tube was sealed and placed in an oil bath preheated to 95° C. Heating was continued for 15 hours. The resulting dark solution was cooled to ambient temperature and concentrated under reduced pressure. The residue was partitioned between chloroform/methanol (75/25 by volume) and aqueous sodium carbonate solution. The organic phase was concentrated and the crude indole ethanamine was purified by flash chromatography on silica gel (0–25% methanol gradient in chloroform as eluent). Fractions containing product were combined and concentrated. The oil was dissolved in diethyl ether (300 mL) containing 1% methanol and treated with dry HCl gas. The hydrochloride salt was isolated by filtration, washed with 2-propanol (50 mL) and diethyl ether (100 mL) and dried to afford 7-bromotryptamine hydrochloride (6.3 g) as a pale solid, which was used without further purification.

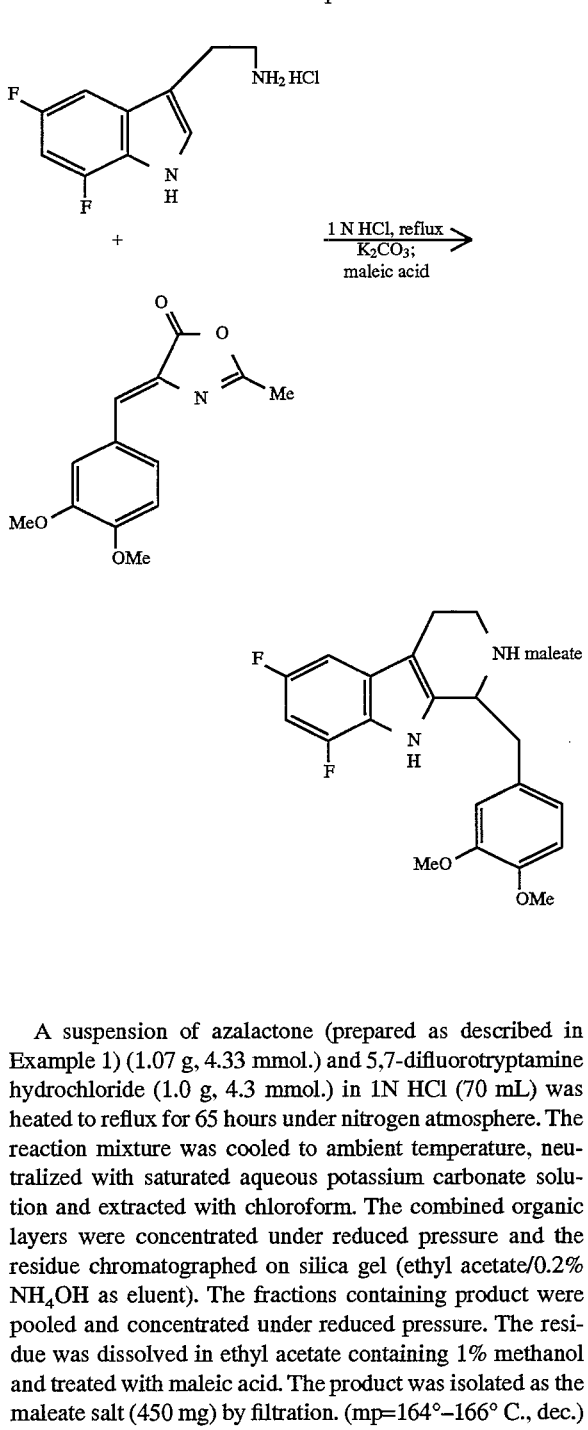

A suspension of azalactone (prepared as described in Example 1) (1.07 g, 4.33 mmol.) and 5,7-difluorotryptamine hydrochloride (1.0 g, 4.3 mmol.) in 1N HCl (70 mL) was heated to reflux for 65 hours under nitrogen atmosphere. The reaction mixture was cooled to ambient temperature, neutralized with saturated aqueous potassium carbonate solution and extracted with chloroform. The combined organic layers were concentrated under reduced pressure and the residue chromatographed on silica gel (ethyl acetate/0.2% NH$_4$OH as eluent). The fractions containing product were pooled and concentrated under reduced pressure. The residue was dissolved in ethyl acetate containing 1% methanol and treated with maleic acid. The product was isolated as the maleate salt (450 mg) by filtration. (mp=164°–166° C., dec.)

| Analysis | Calculated | Found |
|---|---|---|
| C | 60.76 | 60.63 |
| H | 5.10 | 5.14 |
| N | 5.90 | 5.82 |

EXAMPLE 7

Preparation of 7-methyl-8-bromo-1-[(3,4-dimethoxyphenyl)-methyl]-1,2,3,4-tetrahydro-9H-pyrido[3,4-b]indole hydrochloride

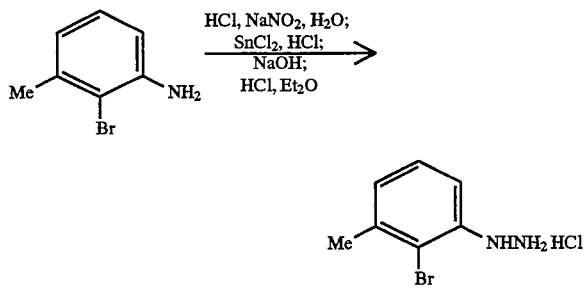

2-Bromo-3-methylphenylhydrazine hydrochloride (23 g) was prepared as described for 2-bromo-4-methylphenylhydrazine hydrochloride in Example 4, except using 2-bromo-3-methylaniline as starting material.

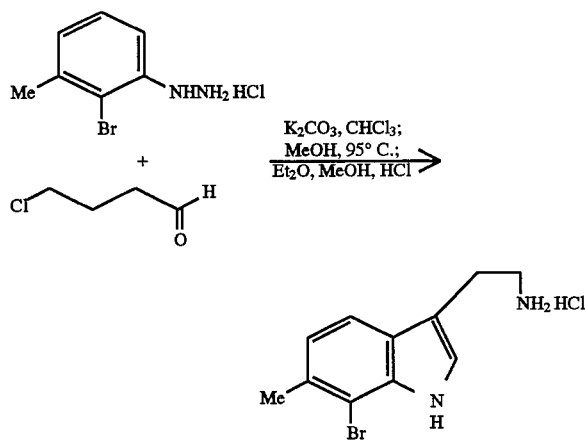

6-Methyl-7-bromotryptamine hydrochloride was prepared (2.42 g) as described for 5-methyl-7-bromotryptamine hydrochloride in Example 4, except using 2-bromo-3-methylphenylhydrazine hydrochloride as starting material.

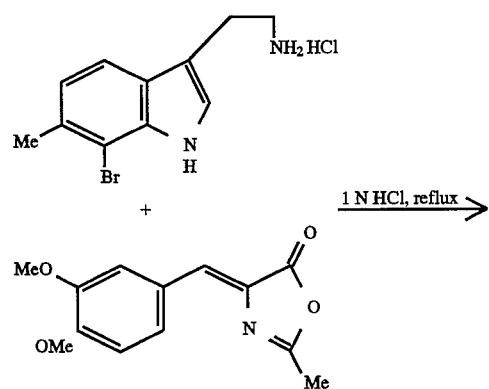

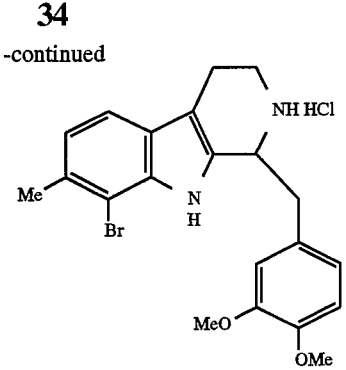

A suspension of azalactone (prepared as described in Example 1) (3.63 g, 14.7 mmol.) and 6-methyl-7-bromotryptamine hydrochloride (4.25 g, 4.21 mmol.) in 1N HCl (150 mL) was heated to reflux for 18 hours under nitrogen atmosphere. The reaction mixture was cooled to ambient temperature, neutralized with saturated aqueous potassium carbonate solution and extracted with chloroform. The combined organic layers were concentrated under reduced pressure and the residue chromatographed on silica gel (ethyl acetate/0.2% NH$_4$OH as eluent). The fractions containing product were pooled and concentrated under reduced pressure. The residue was dissolved in ethyl acetate containing 1% methanol and treated with dry HCl. The product was isolated as the hydrochloride salt (3.11 g) by filtration. m/e=414.

| Analysis | Calculated | Found |
|---|---|---|
| C | 55.83 | 56.13 |
| H | 5.18 | 5.29 |
| N | 6.20 | 6.31 |

EXAMPLE 8

Preparation of 6-(1,1-dimethylethyl)-1-[(3,4-dimethoxyphenyl)methyl]1,2,3,4-tetrahydro-1-9H-pyrido-[3,4b]indole hydrochloride

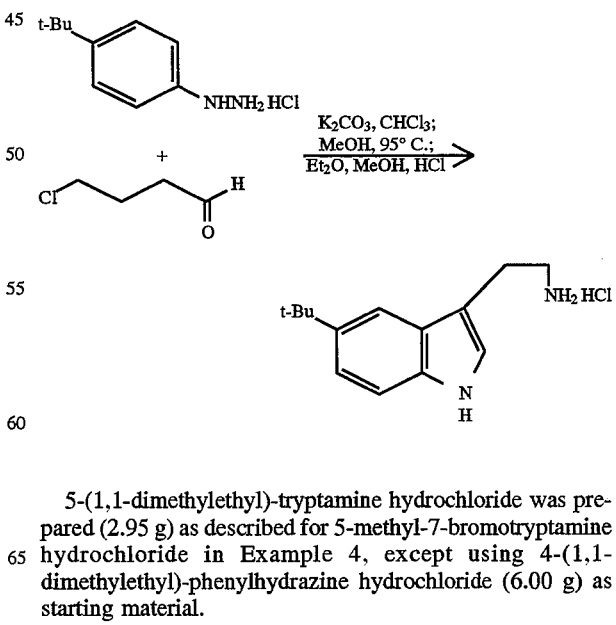

5-(1,1-dimethylethyl)-tryptamine hydrochloride was prepared (2.95 g) as described for 5-methyl-7-bromotryptamine hydrochloride in Example 4, except using 4-(1,1-dimethylethyl)-phenylhydrazine hydrochloride (6.00 g) as starting material.

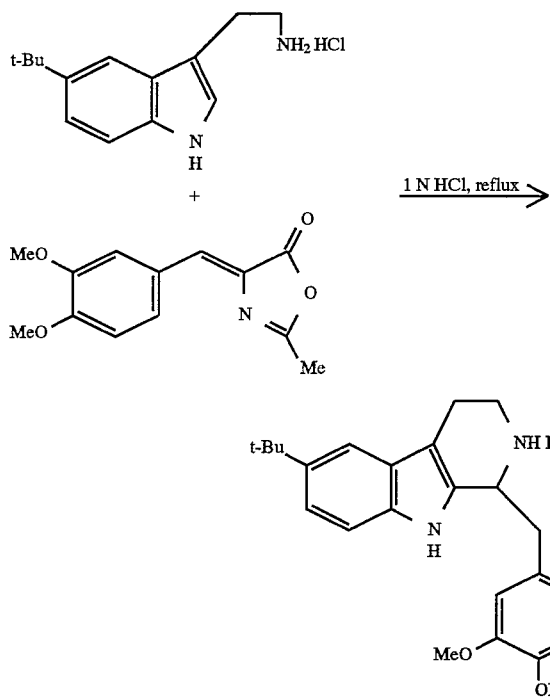

A suspension of azalactone (prepared as described in Example 1) (1.25 g, 5.26 mmol.) and 5-(1,1-dimethylethyl) tryptamine hydrochloride (1.33 g, 5.26 mmol.) in 1N HCl (50 mL) was heated to reflux for 24 hours under nitrogen atmosphere. The reaction mixture was cooled to ambient temperature, and the crude product isolated by filtration. The brown solid was triturated with isopropyl alcohol (3×50 mL) and washed with diethyl ether (3×50 mL). Recrystallization from ethanol afforded 0.74 g of desired product as a pale solid.

| Analysis | Calculated | Found |
|---|---|---|
| C | 69.47 | 69.66 |
| H | 7.53 | 7.50 |
| N | 6.75 | 6.71 |

EXAMPLE 9

Preparation of 5-fluoro-6-methyl-1-[(3,4-dimethoxyphenyl)methyl]-1,2,3,4-tetrahydro-9H-pyrido[3,4-b]indole

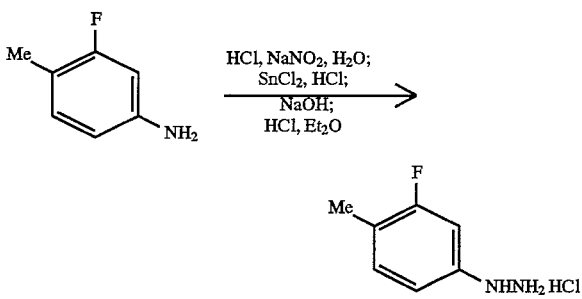

3-Fluoro-4-methylphenylhydrazine hydrochloride (21.4 g) was prepared as described for 2-bromo-4 methylphenyl- hydrazine hydrochloride in Example 4, except using 3-fluoro-4-methylaniline as starting material.

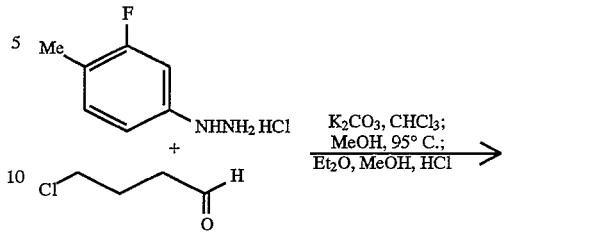

4-Fluoro-5-methyltryptamine hydrochloride was prepared (2.20 g) as described for 5-methyl-7-bromotryptamine hydrochloride in Example 4, except using 3-fluoro-4-methylphenylhydrazine hydrochloride (6.00 g) as starting material.

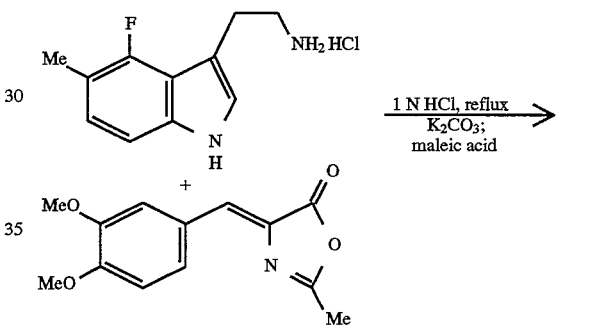

A suspension of azalactone (prepared as described in Example 1) (0.76 g, 3.06 mmol.) and 4-fluoro-5-methyltryptamine hydrochloride (0.70 g, 3.06 mmol.) in 1N HCl (40 mL) was heated to reflux for 24 hours under nitrogen atmosphere. The reaction mixture was cooled to ambient temperature, neutralized with saturated aqueous potassium carbonate solution and extracted with chloroform. The combined organic layers were concentrated under reduced pressure and the residue chromatographed on silica gel (ethyl acetate/0.2% NH$_4$OH as eluent). The fractions containing product were pooled and concentrated under reduced pressure. The residue was dissolved in ethyl acetate containing 1% methanol and treated with maleic acid. The product was isolated as the maleate salt (60 mg) by filtration. mp. 191°–194° C.

| Analysis | Calculated | Found |
|---|---|---|
| C | 63.82 | 63.60 |
| H | 5.78 | 5.65 |
| N | 5.95 | 5.92 |

EXAMPLE 10

Preparation of 7,8,9,10-tetrahydro-10-[(3,4-dimethoxyphenyl)methyl]-11H-benzo[g]pyrido[3,4-b]indole

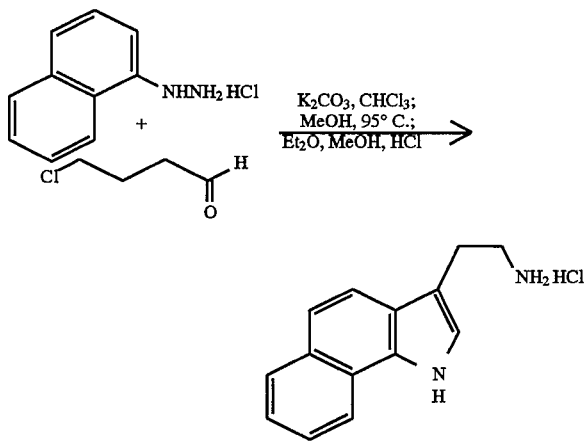

6,7-Benzotryptamine hydrochloride was prepared (2.85 g) as described for 5-methyl-7-bromotryptamine hydrochloride in Example 4, except using 1-naphthyl-hydrazine hydrochloride (6.00 g) as starting material.

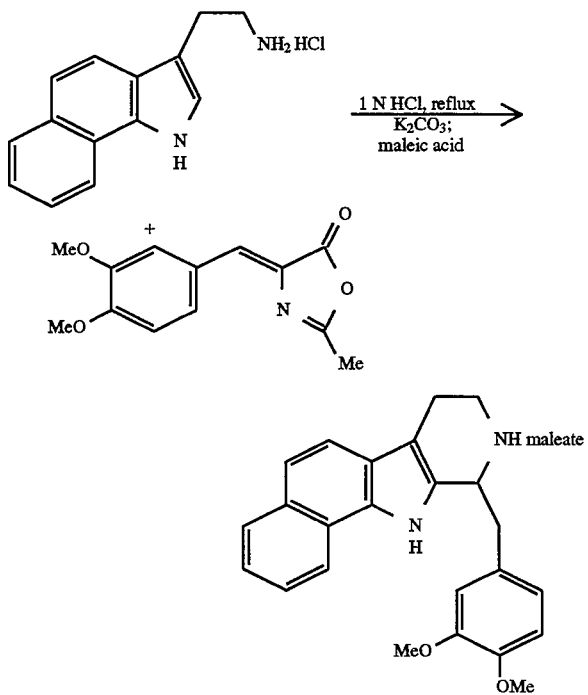

A suspension of azalactone (prepared as described in Example 1) (1.51 g, 6.11 mmol.) and 6,7-benzotryptamine hydrochloride (1.50 g, 6.11 mmol.) in 1N HCl (40 mL) was heated to reflux for 24 hours under nitrogen atmosphere. The reaction mixture was cooled to ambient temperature, neutralized with saturated aqueous potassium carbonate solution and extracted with chloroform. The combined organic layers were concentrated under reduced pressure and the residue chromatographed on silica gel (ethyl acetate/0.2% NH$_4$OH as eluent). The fractions containing product were pooled and concentrated under reduced pressure. The residue was dissolved in ethyl acetate containing 1% methanol and treated with maleic acid. The product was isolated as the maleate salt (240 mg) by filtration. m/e=373, mp. 187° C. (dec.)

| Analysis | Calculated | Found |
|---|---|---|
| C | 68.84 | 68.63 |
| H | 5.78 | 5.91 |
| N | 5.73 | 5.67 |

EXAMPLE 11

Preparation of 6-cyclohexyl-1-[(3,4-dimethoxyphenyl)-methyl]-1,2,3,4-tetrahydro-9H-pyrido[3,4-b]indole hydrochloride

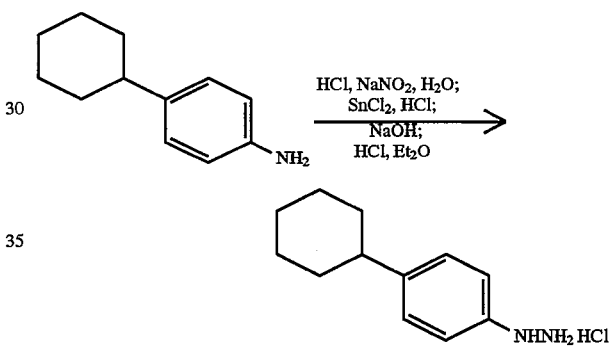

4-Cyclohexylphenylhydrazine hydrochloride 35.6 g) was prepared as described for 2-bromo-4-methylphenylhydrazine hydrochloride in Example 4, except using 4-cyclohexylaniline as starting material.

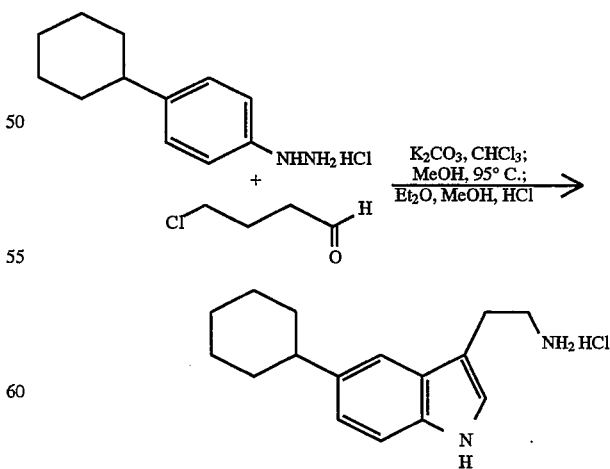

5-Cyclohexyltryptamine hydrochloride was prepared (1.29 g) as described for 5-methyl-7-bromotryptamine hydrochloride in Example 4, except using 4-cyclohexylphenylhydrazine hydrochloride as starting material.

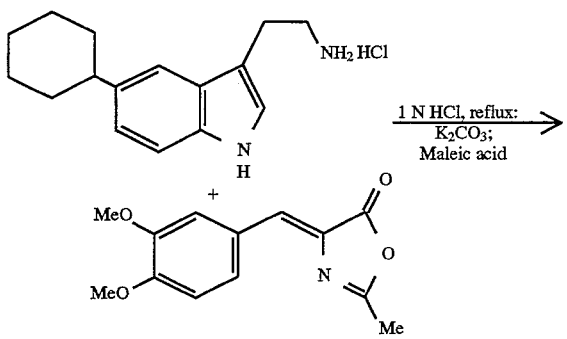

A suspension of azalactone (prepared as described in Example 1) (0.54 g, 2.18 mmol.) and 5-cyclohexyltryptamine hydrochloride (0.6 g, 2.18 mmol.) in 1N HCl (30 mL) was heated to reflux for 14 hours under nitrogen atmosphere. The reaction mixture was cooled to ambient temperature, neutralized with saturated aqueous potassium carbonate solution and extracted with chloroform. The combined organic layers were concentrated under reduced pressure and the residue chromatographed on silica gel (ethyl acetate/0.2% $NH_4OH$ as eluent). The fractions containing product were pooled and concentrated under reduced pressure. The residue was dissolved in ethyl acetate containing 1% methanol and treated with maleic acid. The product was isolated as the maleate salt (140 mg) by filtration. m/e=404.

| Analysis | Calculated | Found |
|---|---|---|
| C | 69.21 | 69.17 |
| H | 6.97 | 7.01 |
| N | 5.38 | 5.53 |

EXAMPLE 12

Preparation of 5,8-dimethyl-1,2,3,4-tetrahydro-1-[(3,4-dimethoxyphenyl)methyl]-9H-pyrido[3,4b]indole hydrochloride

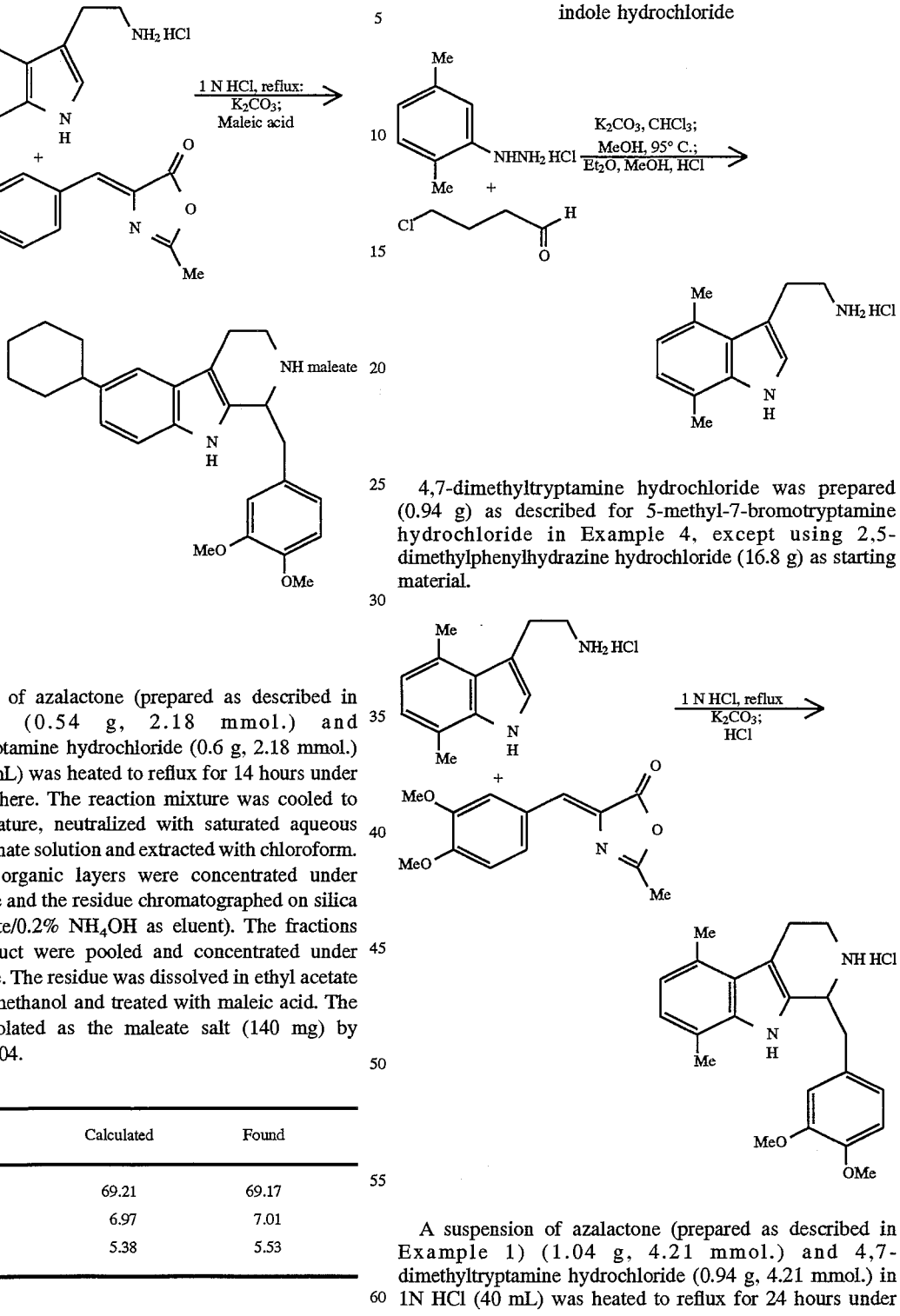

4,7-dimethyltryptamine hydrochloride was prepared (0.94 g) as described for 5-methyl-7-bromotryptamine hydrochloride in Example 4, except using 2,5-dimethylphenylhydrazine hydrochloride (16.8 g) as starting material.

A suspension of azalactone (prepared as described in Example 1) (1.04 g, 4.21 mmol.) and 4,7-dimethyltryptamine hydrochloride (0.94 g, 4.21 mmol.) in 1N HCl (40 mL) was heated to reflux for 24 hours under nitrogen atmosphere. The reaction mixture was cooled to ambient temperature, neutralized with saturated aqueous potassium carbonate solution and extracted with chloroform. The combined organic layers were concentrated under reduced pressure and the residue chromatographed on silica gel (ethyl acetate/0.2% NH₄OH as eluent). The fractions containing product were pooled and concentrated under reduced pressure. The residue was dissolved in ethyl acetate containing 1% methanol and treated with anhydrous HCl. The product was isolated as the hydrochloride salt (370 mg) by filtration. m/e=349.

| Analysis | Calculated | Found |
|---|---|---|
| C | 68.29 | 68.59 |
| H | 7.03 | 6.92 |
| N | 7.24 | 7.04 |

EXAMPLE 13

Preparation of 6-(1-methylethyl)-1,2,3,4-tetrahydro-1-[(3,4-dimethoxyphenyl)methyl]-9H-pyrido[3,4b]indole

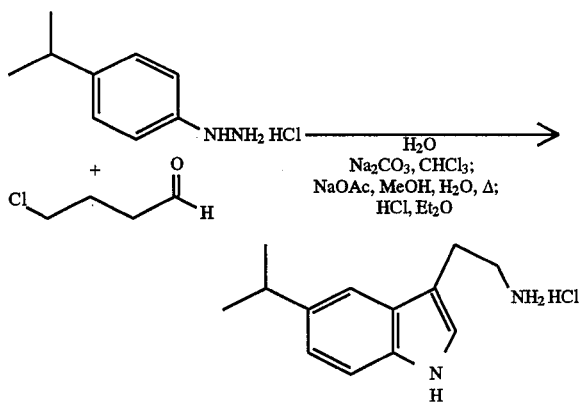

To a stirred suspension of 4-isopropylphenylhydrazine hydrochloride monohydrate (15.3 g, 91.95 mmol.) in chloroform (250 mL) was added saturated sodium carbonate solution (250 mL). The mixture was stirred for 30 minutes and extracted with chloroform (2×200 mL). The combined organic phases were concentrated to afford the hydrazine free base as a yellow oil. This oil was dissolved in methanol (200 mL) and water (5 mL) and treated with sodium acetate (6.72 g, 82 mmol.) and 4-chlorobutanal (8.7 g, 82 mmol.). The mixture was placed in a sealable tube and purged with nitrogen for 10 minutes. The tube was sealed and placed in an oil bath preheated to 100° C. Heating was continued for 18 hours. The resulting dark solution was cooled to ambient temperature and concentrated under reduced pressure. The residue was partitioned between chloroform/methanol (75/25 by volume) and aqueous sodium carbonate solution. The organic phase was concentrated and the crude indole ethanamine was purified by flash chromatography on silica gel (0–25% methanol gradient in chloroform as eluent). Fractions containing product were combined and concentrated. The oil was dissolved in diethyl ether (300 mL) containing 1% methanol and treated with dry HCl gas. The hydrochloride salt was isolated by filtration, washed with 2-propanol (50 mL) and diethyl ether (100 mL) and dried to afford 5-isopropyltryptamine hydrochloride (9.8 g) as a pale solid, which was used without further purification.

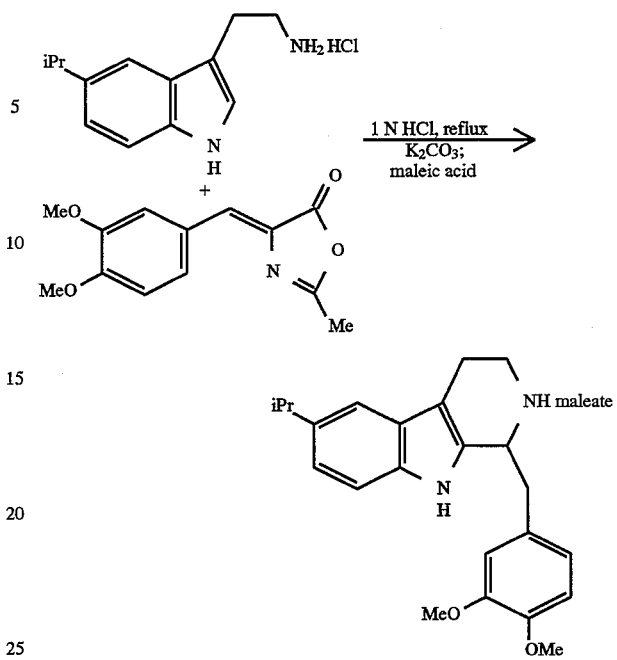

A suspension of azalactone (prepared as described in Example 1) (1.55 g, 6.31 mmol.) and 5-isopropyltryptamine hydrochloride (1.76 g, 7.37 mmol.) in 1N HCl (40 ml) was heated to reflux for 24 hours under nitrogen atmosphere. The reaction mixture was cooled to ambient temperature, neutralized with saturated aqueous potassium carbonate solution and extracted with chloroform. The combined organic layers were concentrated under reduced pressure and the residue chromatographed on silica gel (ethyl acetate/0.2% NH₄OH as eluent). The fractions containing product were pooled and concentrated under reduced pressure. The residue was dissolved in ethyl acetate containing 1% methanol and treated with maleic acid. The product was isolated as the maleate salt (310 mg) by filtration. m/e=365, mp. 196°–200° C.

| Analysis | Calculated | Found |
|---|---|---|
| C | 67.48 | 67.74 |
| H | 6.71 | 6.75 |
| N | 5.83 | 5.92 |

EXAMPLE 14

Preparation of 6,8-dimethyl-1,2,3,4-tetrahydro-1-[(3,4-dimethoxyphenyl)methyl]-9H-pyrido[3,4b]indole hydrochloride

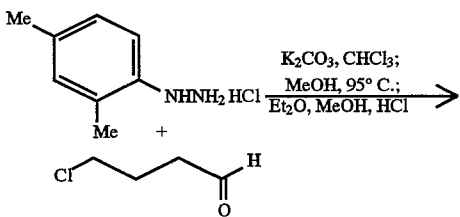

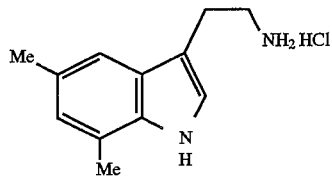

5,7-Dimethyltryptamine hydrochloride was prepared (2.86 g) as described for 5-methyl-7-bromotryptamine hydrochloride in Example 4, except using 2,4-dimethylphenylhydrazine hydrochloride (15.0 g) as starting material.

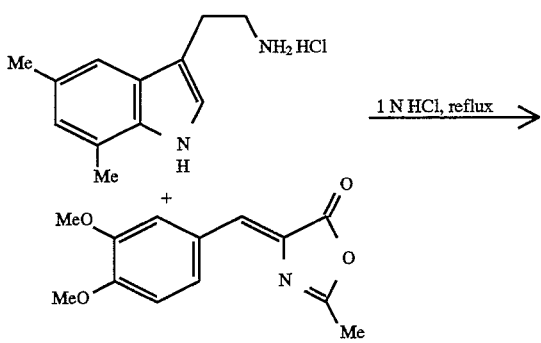

A suspension of azalactone (prepared as described in Example 1) (1.65 g, 6.67 mmol.) and 5,7-dimethyltryptamine hydrochloride (1.50 g, 6.67 mmol.) in 1N HCl (70 mL) was heated to reflux for 24 hours under nitrogen atmosphere. The reaction mixture was cooled to ambient temperature and the crude product isolated by filtration. The solid was triturated with ethanol/hexanes (3×50 mL) and washed with hexanes (3×50 mL). The product was isolated by filtration (820 mg). m/e=350.

| Analysis | Calculated | Found |
|---|---|---|
| C | 68.29 | 68.07 |
| H | 7.03 | 7.12 |
| N | 7.24 | 7.23 |

EXAMPLE 15

Preparation of 5,7-dimethyl-1,2,3,4-tetrahydro-1-[(3,4-dimethoxyphenyl)methyl]-9H-pyrido[3,4b]indole hydrochloride

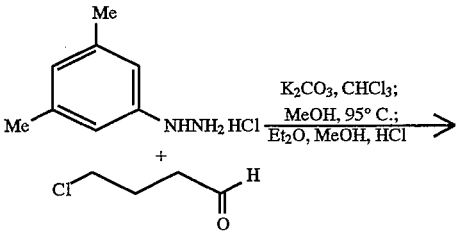

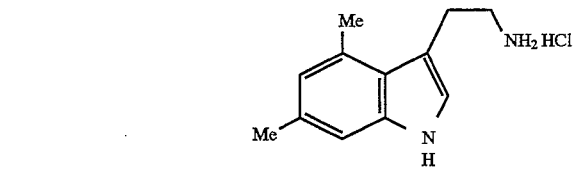

4,6-Dimethyltryptamine hydrochloride was prepared (1.06 g) as described for 5-methyl-7-bromotryptamine hydrochloride in Example 4, except using 3,5-dimethylphenylhydrazine hydrochloride (7.65 g) as starting material.

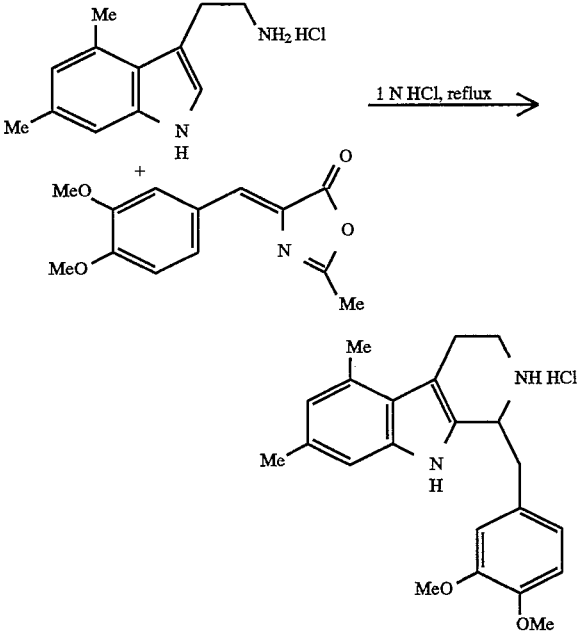

A suspension of azalactone (prepared as described in Example 1) (1.16 g, 4.69 mmol.) and 4,6-dimethyltryptamine hydrochloride (1.05 g, 4.67 mmol.) in 1N HCl (60 mL) was heated to reflux for 24 hours under nitrogen atmosphere. The reaction mixture was cooled to ambient temperature and the crude product isolated by filtration. The solid was triturated with ethanol/hexanes (3×50 mL) and washed with hexanes (3×50 mL). The product was isolated by filtration (770 mg). m/e=350.

| Analysis | Calculated | Found |
|---|---|---|
| C | 68.29 | 68.09 |
| H | 7.03 | 7.12 |
| N | 7.24 | 7.02 |

EXAMPLE 16

Preparation of 6,7-dimethyl-1,2,3,4-tetrahydro-1-[(3,4-dimethoxyphenyl)methyl]-9H-pyrido[3,4b]indole

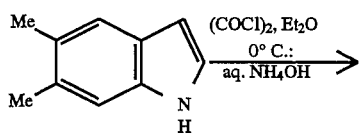

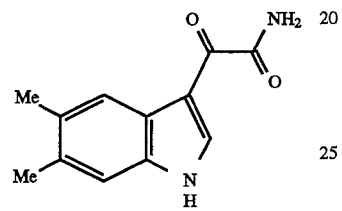

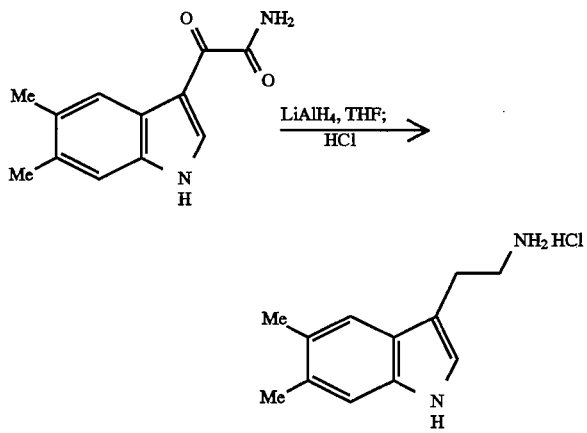

To a stirred, cooled (0° C.) solution of 5,6-dimethylindole (3.69 g, 25.4 mmol.) in dry diethyl ether (75 mL) was added dropwise oxalyl chloride (3.8 mL, 43.0 mmol.) over 2 minutes. After further stirring for 30 minutes, the bright yellow acid chloride (5.99 g) was isolated by filtration and washed with dry diethyl ether. This acid chloride was added in portions to a rapidly stirred solution of aqueous (30%) ammonium hydroxide (100 mL). After the addition was complete, the mixture was further stirred at ambient temperature for 30 minutes and the crude product isolated by filtration. Recrystallization from THF/diethyl ether afforded product (3.05 g) as a tan solid.

To a stirred, refluxing solution of amide (prepared above) (3.05 g, 14.1 mmol.) in THF was added dropwise a suspension of lithium aluminum hydride (3.07 g, 81.3 mmol.) in THF over 1 H. Upon complete addition, the mixture was further heated to reflux for 14 H. The reaction mixture was cooled to 0° C. and carefully treated with water (3.1 mL) followed by 15% sodium hydroxide solution (3.1 mL), followed by water (9.3 mL). The salts were removed by filtration and the filtrate was concentrated under reduced pressure. The residue was dissolved in diethyl ether (80 mL) with 5% ethyl acetate and treated with anhydrous HCl. The hydrochloride salt (2.65 g) was isolated by filtration and washed with dry ether.

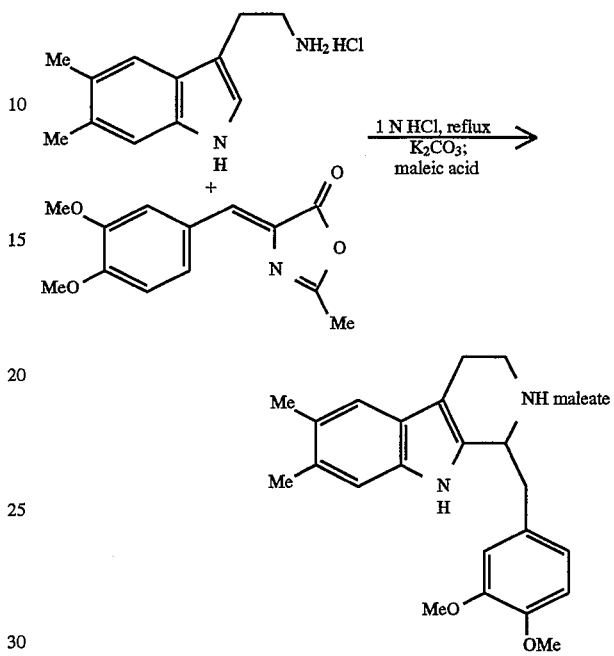

A suspension of azalactone (prepared as described in Example 1) (1.10 g, 4.45 mmol.) and 5,6-dimethyltryptamine hydrochloride (1.00 g, 4.45 mmol.) in 1N HCl (60 mL) was heated to reflux for 24 hours under nitrogen atmosphere. The reaction mixture was cooled to ambient temperature, neutralized with saturated aqueous potassium carbonate solution and extracted with chloroform. The combined organic layers were concentrated under reduced pressure and the residue chromatographed on silica gel (ethyl acetate/0.2% NH$_4$OH as eluent). The fractions containing product were pooled and concentrated under reduced pressure. The residue was dissolved in ethyl acetate containing 1% methanol and treated with maleic acid. The product was isolated as the maleate salt (450 mg) by filtration. mp. 197°–200° C.

| Analysis | Calculated | Found |
|---|---|---|
| C | 66.94 | 67.01 |
| H | 6.48 | 6.56 |
| N | 6.00 | 5.98 |

EXAMPLE 17

Preparation of 6-ethyl-1,2,3,4-tetrahydro-1-[(3,4-dimethoxyphenyl)methyl]-9H-pyrido[3,4b]indole

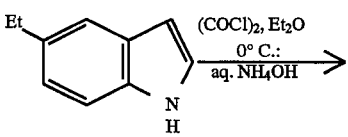

47

-continued

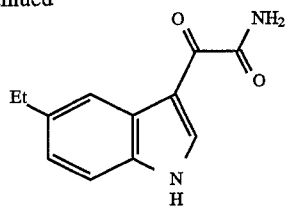

To a stirred, cooled (0° C.) solution of 5-ethylindole (4.0 g, 27.5 mmol.) in dry diethyl ether (250 mL) was added dropwise oxalyl chloride (4.8 mL, 55.1 mmol.) over 2 minutes. After further stirring for 30 minutes, the bright yellow acid chloride was isolated by filtration and washed with dry diethyl ether. This acid chloride was added in portions to a rapidly stirred solution of aqueous (30%) ammonium hydroxide (200 mL). After the addition was complete, the mixture was further stirred at ambient temperature for 30 minutes and the crude product isolated by filtration (4.7 g) as a tan solid.

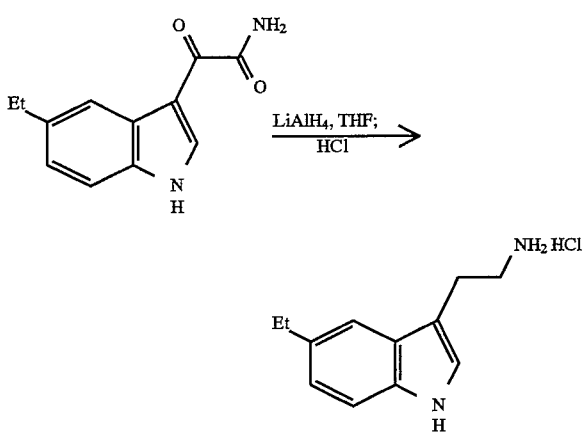

To a stirred, refluxing solution of amide (prepared above) (4.7 g, 21.7 mmol.) in THF was added dropwise a suspension of lithium aluminum hydride (4.7 g, 121 mmol.) in THF over 1 H. Upon complete addition, the mixture was further heated to reflux for 14 H. The reaction mixture was cooled to 0° C. and carefully treated with water (4.7 mL) followed by 15% sodium hydroxide solution (4.7 mL), followed by water (14.1 mL). The salts were removed by filtration and the filtrate was concentrated under reduced pressure. The residue was dissolved in diethyl ether (80 mL) with 5% ethyl acetate and treated with anhydrous HCl. The hydrochloride

48 salt (4.02 g) was isolated by filtration and washed with dry ether.

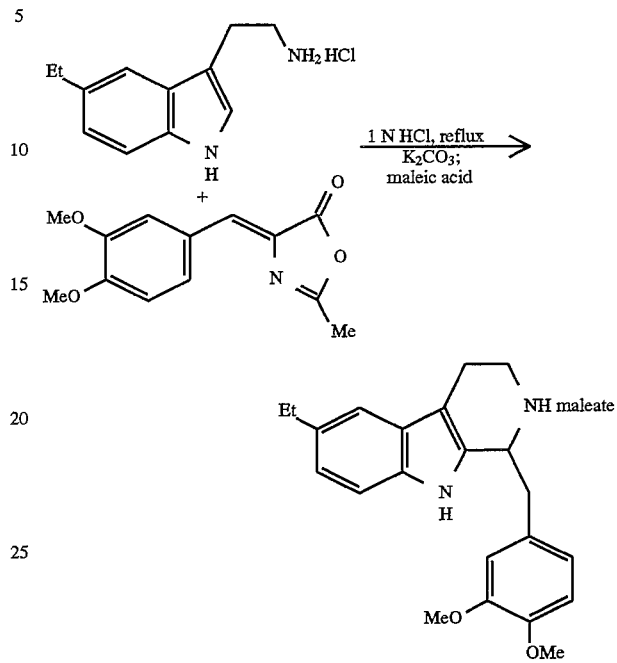

A suspension of azalactone (prepared as described in Example 1) (1.10 g, 4.45 mmol.) and 5,6-dimethyltryptamine hydrochloride (1.00 g, 4.45 mmol.) in 1N HCl (60 mL) was heated to reflux for 24 hours under nitrogen atmosphere. The reaction mixture was cooled to ambient temperature, neutralized with saturated aqueous potassium carbonate solution and extracted with chloroform. The combined organic layers were concentrated under reduced pressure and the residue chromatographed on silica gel (ethyl acetate/0.2% $NH_4OH$ as eluent). The fractions containing product were pooled and concentrated under reduced pressure. The residue was dissolved in ethyl acetate containing 1% methanol and treated with maleic acid. The product was isolated as the maleate salt (520 mg) by filtration. mp. 185° C.(dec.).

| Analysis | Calculated | Found |
|---|---|---|
| C | 66.94 | 66.95 |
| H | 6.48 | 6.55 |
| N | 6.01 | 5.99 |

EXAMPLE 18

Preparation of 6-bromo-1,2,3,4-tetrahydro-1-[(3,4-dimethoxyphenyl)methyl]-9H-pyrido[3,4b]indole

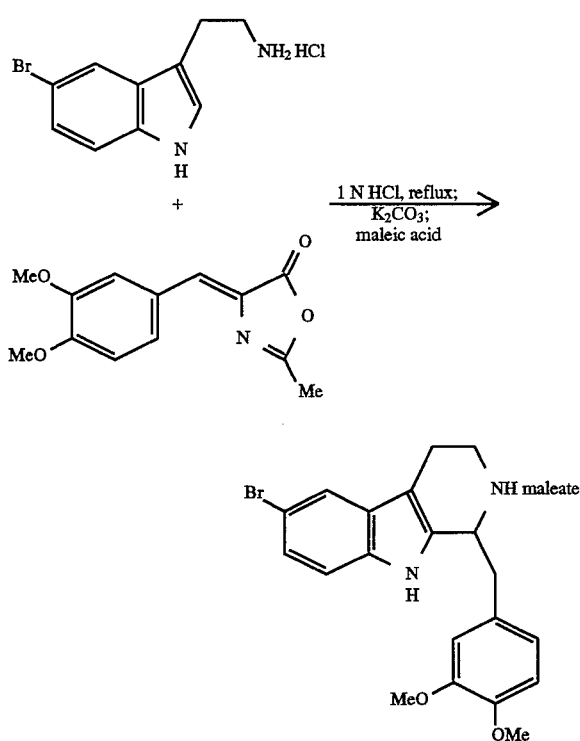

A suspension of azalactone (prepared as described in Example 1) (0.9 g, 3.7 mmol.) and 5-bromotryptamine hydrochloride (1.01 g, 3.7 mmol.) in 1N HCl (60 mL) was heated to reflux for 18 hours under nitrogen atmosphere. The reaction mixture was cooled to ambient temperature, neutralized with saturated aqueous potassium carbonate solution and extracted with chloroform. The combined organic layers were concentrated under reduced pressure and the residue chromatographed on silica gel (ethyl acetate/0.2% $NH_4OH$ as eluent). The fractions containing product were pooled and concentrated under reduced pressure. The residue was dissolved in ethyl acetate containing 1% methanol and treated with maleic acid. The product was isolated as the maleate salt (800 mg) by filtration. (mp=184°–188° C., dec.) m/e=403.

| Analysis | Calculated | Found |
|---|---|---|
| C | 55.72 | 55.51 |
| H | 4.87 | 5.09 |
| N | 5.41 | 5.36 |

EXAMPLE 19

Preparation of 7,8-dimethyl-1,2,3,4-tetrahydro-1-[(3,4-dimethoxyphenyl)methyl]-9H-pyrido[3,4b]indole hydrochloride

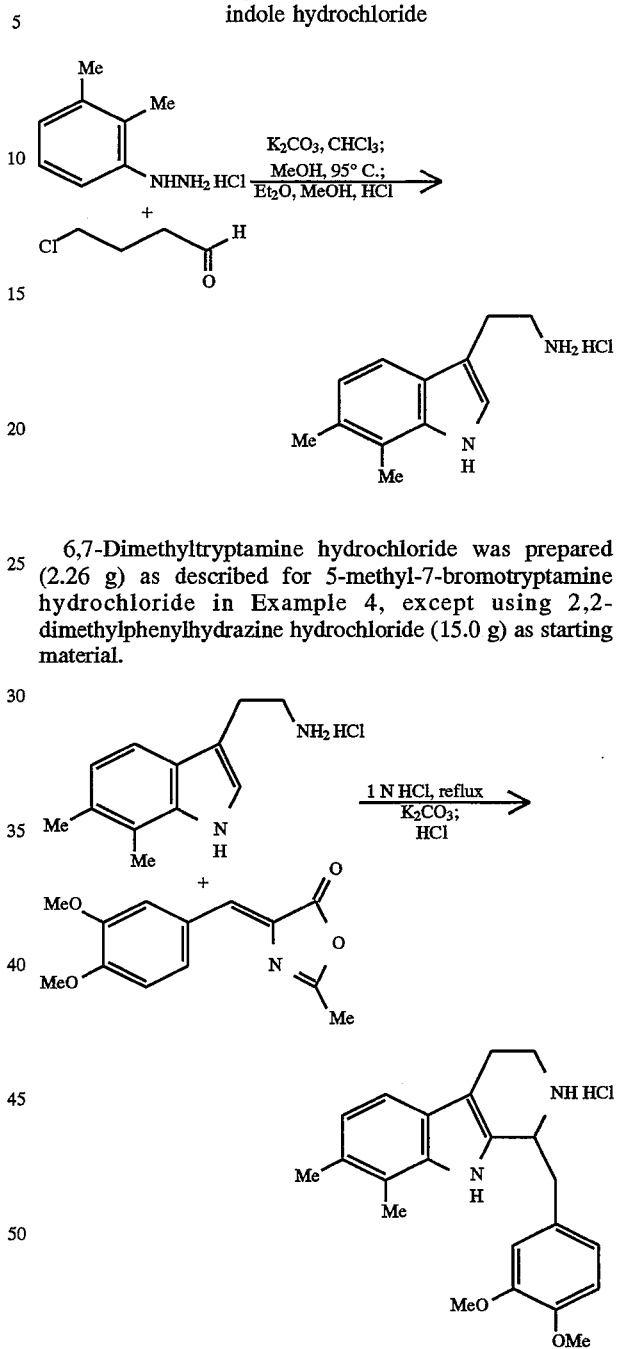

6,7-Dimethyltryptamine hydrochloride was prepared (2.26 g) as described for 5-methyl-7-bromotryptamine hydrochloride in Example 4, except using 2,2-dimethylphenylhydrazine hydrochloride (15.0 g) as starting material.

A suspension of azalactone (prepared as described in Example 1) (1.39 g, 5.62 mmol.) and 6,7-dimethyltryptamine hydrochloride (1.26 g, 5.61 mmol.) in 1N HCl (70 mL) was heated to reflux for 24 hours under nitrogen atmosphere. The reaction mixture was cooled to ambient temperature, neutralized with saturated aqueous potassium carbonate solution and extracted with chloroform. The combined organic layers were concentrated under reduced pressure and the residue chromatographed on silica gel (ethyl acetate/0.2% $NH_4OH$ as eluent). The fractions containing product were pooled and concentrated under reduced pressure. The residue was dissolved in ethyl acetate containing 1% methanol and treated with anhydrous HCl. The product was isolated as the hydrochloride salt (290 mg) by filtration. m/e=350.

| Analysis | Calculated | Found |
|----------|------------|-------|
| C | 68.29 | 68.51 |
| H | 7.03 | 6.87 |
| N | 7.24 | 7.22 |

EXAMPLE 20

Preparation of 6-methyl-1,2,3,4-tetrahydro-1-[(3,4-dimethoxyphenyl)methyl]-9H-pyrido[3,4b]indole hydrochloride

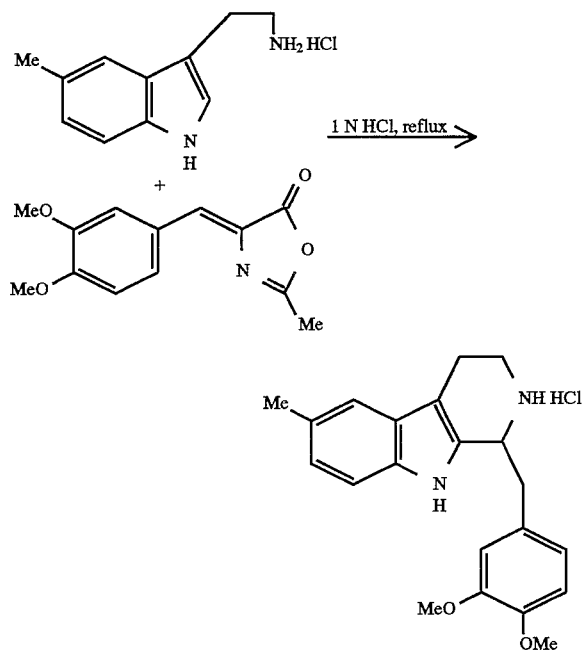

A suspension of azalactone (prepared as described in Example 1) (3.4 g, 12.4 mmol.) and 5-methyltryptamine hydrochloride (2.0 g, 9.9 mmol.) in 1N HCl (100 mL) was heated to reflux for 24 hours under nitrogen atmosphere. The reaction mixture was cooled to ambient temperature and the crude product isolated by filtration. The solid was triturated with ethanol and washed with diethyl ether. The product was isolated as the hydrochloride salt by filtration (3.2 g). mp. 245°–246° C. (dec.).

| Analysis | Calculated | Found |
|----------|------------|-------|
| C | 67.64 | 67.42 |
| H | 6.67 | 6.66 |
| N | 7.51 | 7.25 |

EXAMPLE 21

Preparation of 6-methyl-1-[(3,4,5-trimethoxyphenyl)-methyl]-1,2,3,4-tetrahydro-9H-pyrido[3,4-b]indole hydrochloride

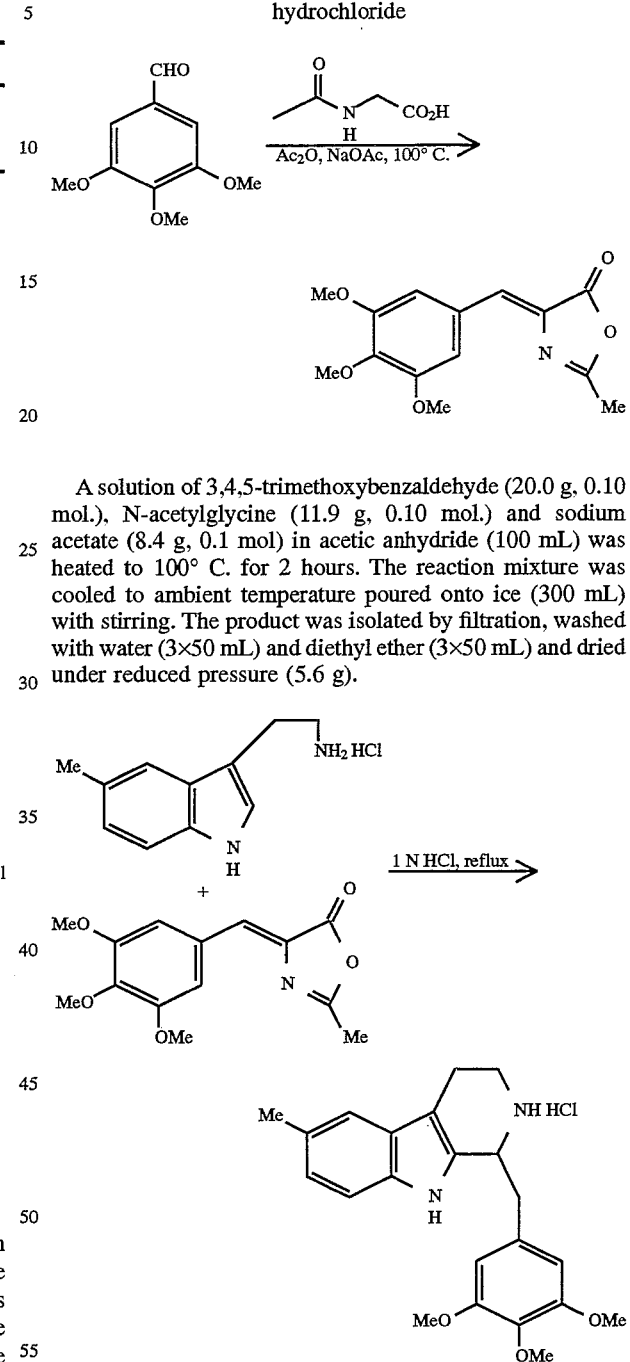

A solution of 3,4,5-trimethoxybenzaldehyde (20.0 g, 0.10 mol.), N-acetylglycine (11.9 g, 0.10 mol.) and sodium acetate (8.4 g, 0.1 mol) in acetic anhydride (100 mL) was heated to 100° C. for 2 hours. The reaction mixture was cooled to ambient temperature poured onto ice (300 mL) with stirring. The product was isolated by filtration, washed with water (3×50 mL) and diethyl ether (3×50 mL) and dried under reduced pressure (5.6 g).

A suspension of azalactone (prepared above) (2.0 g, 7.2 mmol.) and 5-methyltryptamine hydrochloride (1.1 g, 5.4 mmol.) in 1N HCl (20 mL) was heated to reflux for 48 hours under nitrogen atmosphere. The reaction mixture was cooled to ambient temperature and the crude product isolated by filtration. The solid was triturated with isopropanol and washed with diethyl ether. The product was isolated by filtration (650 mg). mp. 228°–229° C.

| Analysis | Calculated | Found |
|---|---|---|
| C | 65.58 | 65.38 |
| H | 6.75 | 6.76 |
| N | 6.95 | 6.92 |

EXAMPLE 22

Preparation of 6-methyl-1-[(2,3,4-trimethoxyphenyl)methyl]-1,2,3,4-tetrahydro-9H-pyrido[3,4-b]indole hydrochloride

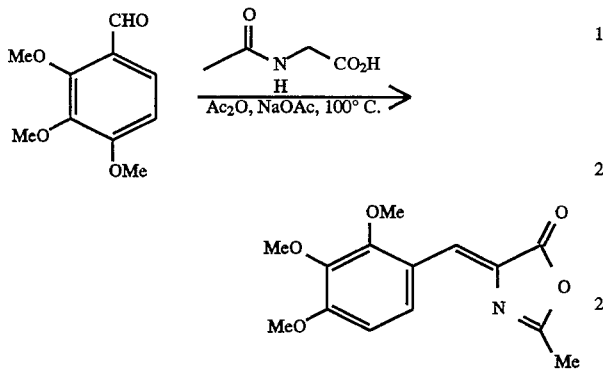

Azalactone (12.28 g) was prepared as in Example 21 except using 2,3,4-trimethoxybenzaldehyde (20.0 g).

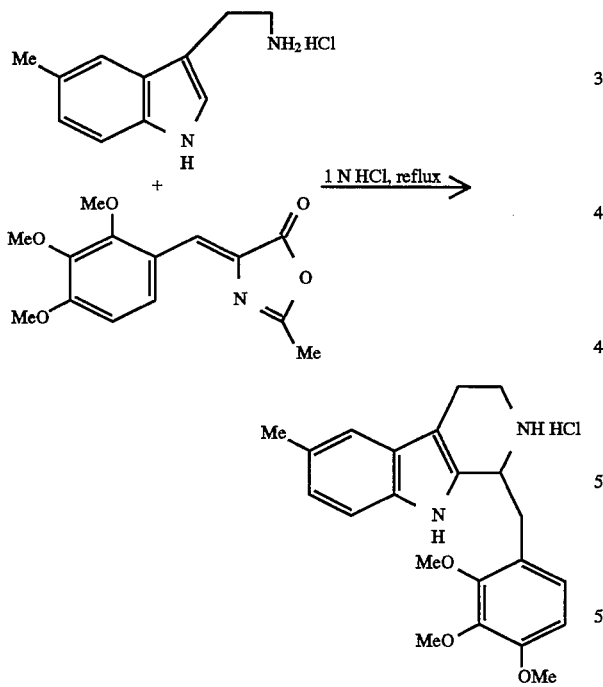

A suspension of azalactone (prepared above) (2.0 g, 7.2 mmol.) and 5-methyltryptamine hydrochloride (1.1 g, 5.4 mmol.) in 1N HCl (20 mL) was heated to reflux for 48 hours under nitrogen atmosphere. The reaction mixture was cooled to ambient temperature and the crude product isolated by filtration. The solid was triturated with isopropanol and washed with diethyl ether The product was isolated by filtration (1.36 g). mp. 214.5° C.

| Analysis | Calculated | Found |
|---|---|---|
| C | 65.58 | 65.41 |
| H | 6.75 | 6.70 |
| N | 6.95 | 6.89 |

EXAMPLE 23

Preparation of 6-methyl-1-[(2-methoxyphenyl)methyl]-1,2,3,4-tetrahydro-9H-pyrido[3,4-b]indole hydrochloride

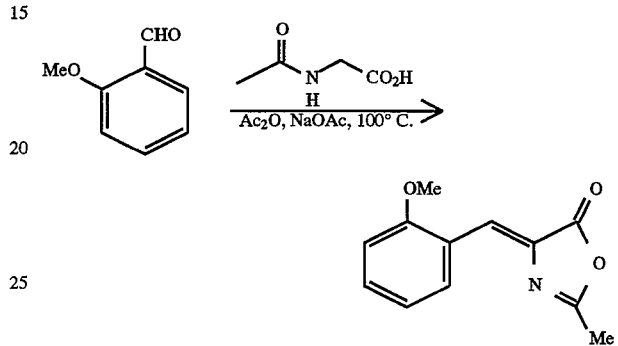

Azalactone (16.42 g) was prepared as in Example 21 except using 2-methoxybenzaldehyde (20.0 g).

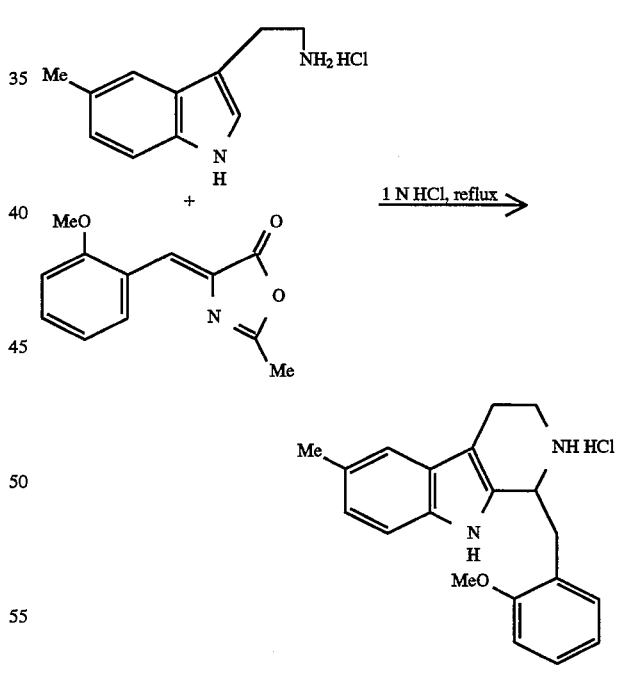

A suspension of azalactone (prepared above) (2.0 g, 9.2 mmol.) and 5-methyltryptamine hydrochloride (1.5 g, 6.9 mmol.) in 1N HCl (20 mL) was heated to reflux for 48 hours under nitrogen atmosphere. The reaction mixture was cooled to ambient temperature and the crude product isolated by filtration. The solid was triturated with isopropanol and washed with diethyl ether The product was isolated by filtration (880 mg). mp. 252.8° C.

| Analysis | Calculated | Found |
|---|---|---|
| C | 70.06 | 70.15 |
| H | 6.76 | 6.83 |
| N | 8.17 | 8.16 |

EXAMPLE 24

Preparation of 6-methyl-1-[(2,4-dimethoxyphenyl)methyl]-1,2,3,4-tetrahydro-9H-pyrido[3,4-b]indole hydrochloride

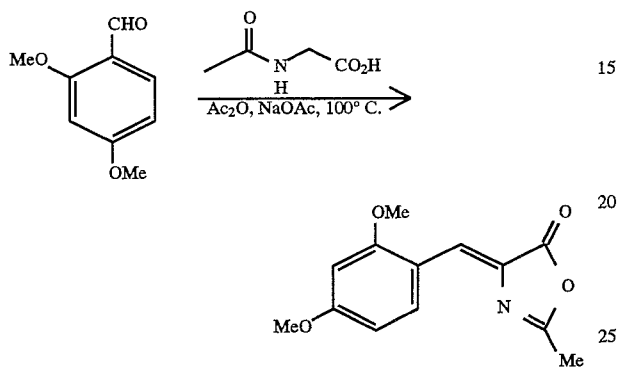

Azalactone (7.55 g) was prepared as in Example 21 except using 2,4-dimethoxybenzaldehyde (20.0 g).

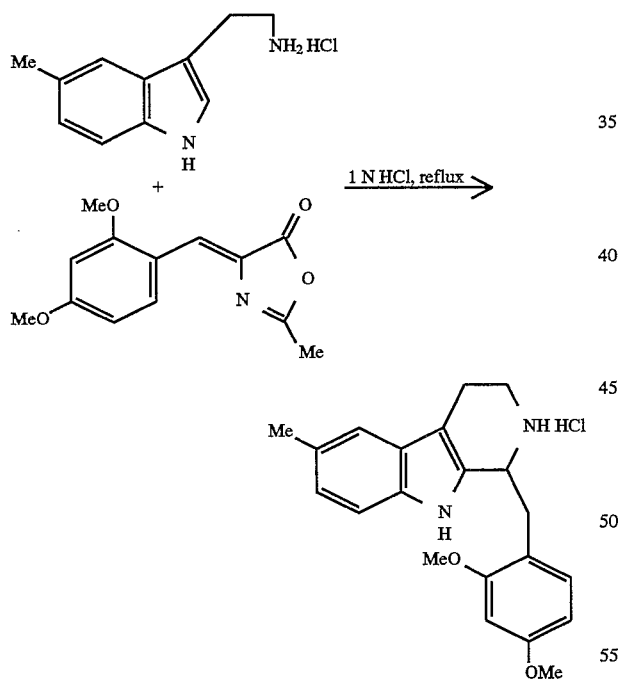

A suspension of azalactone (prepared above) (2.0 g, 8.1 mmol.) and 5-methyltryptamine hydrochloride (1.3 g, 6.1 mmol.) in 1N HCl (20 mL) was heated to reflux for 48 hours under nitrogen atmosphere. The reaction mixture was cooled to ambient temperature, neutralized with saturated aqueous potassium carbonate solution and extracted with chloroform. The combined organic layers were concentrated under reduced pressure and the residue chromatographed on silica gel (ethyl acetate/0.2% NH₄OH as eluent). The fractions containing product were pooled and concentrated under reduced pressure. The residue was dissolved in ethyl acetate containing 1% methanol and treated with anhydrous HCl. The product was isolated as the hydrochloride salt (361 mg) by filtration. mp. 262.6° C.

| Analysis | Calculated | Found |
|---|---|---|
| C | 67.64 | 67.73 |
| H | 6.76 | 6.85 |
| N | 7.51 | 7.50 |

EXAMPLE 25

Preparation of 6-methyl-1-[(2,5-dimethoxyphenyl)methyl]-1,2,3,4-tetrahydro-9H-pyrido[3,4-b]indole hydrochloride

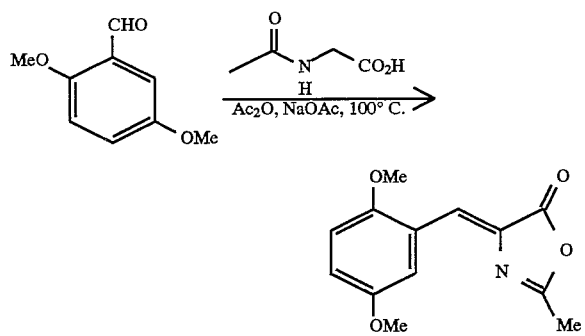

Azalactone (13.21 g) was prepared as in Example 21 except using 2,5-dimethoxybenzaldehyde (20.0 g).

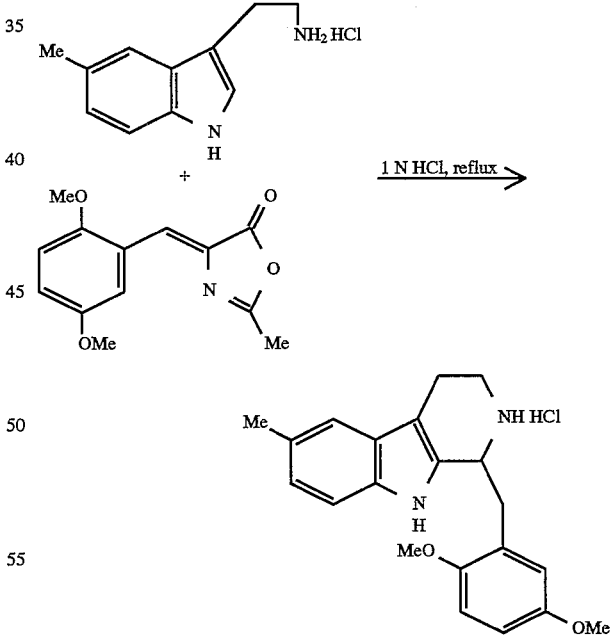

A suspension of azalactone (prepared above) (2.0 g, 8.1 mmol.) and 5-methyltryptamine hydrochloride (1.3 g, 6.1 mmol.) in 1N HCl (20 mL) was heated to reflux for 48 hours under nitrogen atmosphere. The reaction mixture was cooled to ambient temperature, neutralized with saturated aqueous potassium carbonate solution and extracted with chloroform. The combined organic layers were concentrated under reduced pressure and the residue chromatographed on silica gel (ethyl acetate/0.2% NH₄OH as eluent). The fractions containing product were pooled and concentrated under reduced pressure. The residue was dissolved in ethyl acetate containing 1% methanol and treated with anhydrous HCl. The product was isolated as the hydrochloride salt (1.14 g) by filtration. mp. 262 ° C.

| Analysis | Calculated | Found |
|---|---|---|
| C | 67.64 | 67.36 |
| H | 6.76 | 6.71 |
| N | 7.51 | 7.25 |

EXAMPLE 26

Preparation of 6-methyl-1-[(2,4,5-trimethoxyphenyl)-methyl]-1,2,3,4-tetrahydro-9H-pyrido[3,4-b]indole hydrochloride

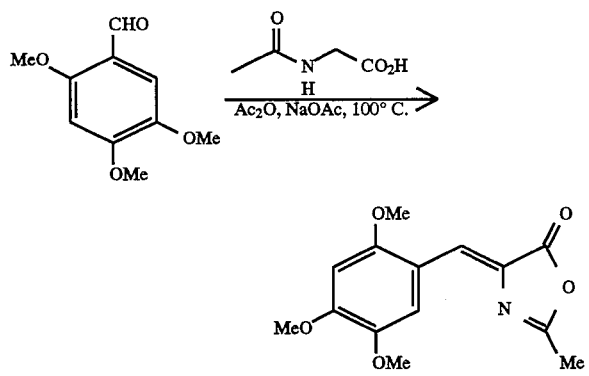

Azalactone (8.36 g) was prepared as in Example 21 except using 2,4,5-trimethoxybenzaldehyde (20.0 g).

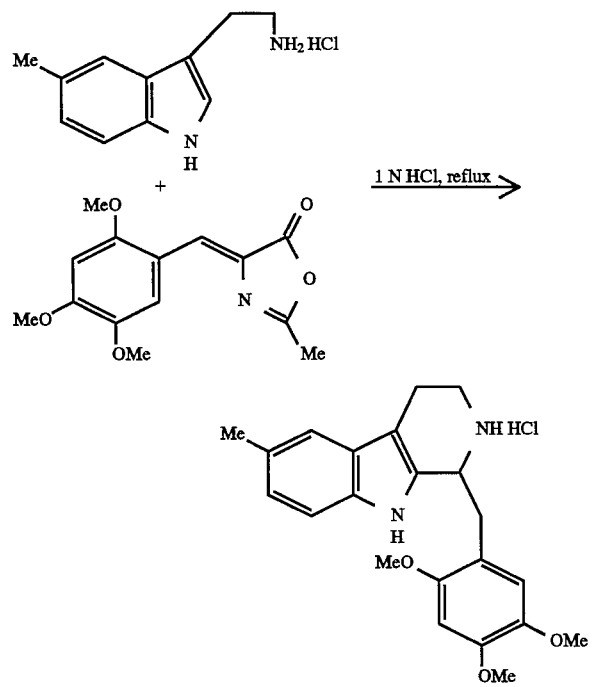

A suspension of azalactone (prepared above) (2.0 g, 7.2 mmol.) and 5-methyltryptamine hydrochloride (1.1 g, 5.4 mmol.) in 1N HCl (20 mL) was heated to reflux for 48 hours under nitrogen atmosphere. The reaction mixture was cooled to ambient temperature and the crude product isolated by filtration. The solid was triturated with isopropanol and washed with diethyl ether. The product was isolated by filtration. Recrystatlization from ethanol/cyclohexane afforded product (299 mg). mp. 176.3° C.

| Analysis | Calculated | Found |
|---|---|---|
| C | 65.58 | 65.51 |
| H | 6.75 | 6.73 |
| N | 6.95 | 6.87 |

EXAMPLE 27

Preparation of 6-(1-methylethyl)-1-[(2,3,4-trimethoxyphenyl)methyl]-1,2,3,4-tetrahydro-9H-pyrido[3,4-b]indole hydrochloride

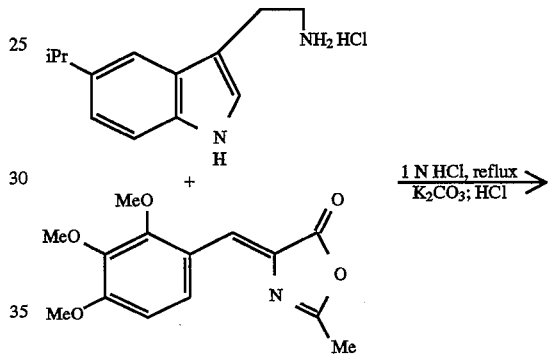

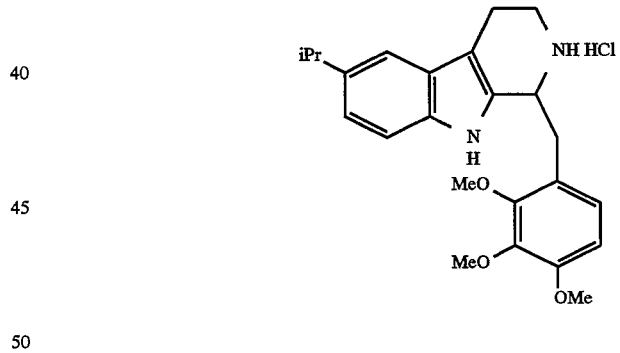

A suspension of azalactone (prepared as in Example 22) (1.0 g, 3.61 mmol.) and 5-isopropyltryptamine hydrochloride (prepared as in Example 13) (646 mg, 2.7 mmol.) in 1N HCl (20 mL) was heated to reflux for 48 hours under nitrogen atmosphere. The reaction mixture was cooled to ambient temperature, neutralized with saturated aqueous potassium carbonate solution and extracted with chloroform. The combined organic layers were concentrated under reduced pressure and the residue chromatographed on silica gel (ethyl acetate/0.2% NH₄OH as eluent). The fractions containing product were pooled and concentrated under reduced pressure. The residue was dissolved in ethyl acetate containing 1% methanol and treated with anhydrous HCl. The product was isolated as the hydrochloride salt (315 mg) by filtration. mp. 147.3° C.

| Analysis | Calculated | Found |
|---|---|---|
| C | 66.89 | 66.80 |
| H | 7.25 | 7.01 |
| N | 6.50 | 6.39 |

EXAMPLE 28

Preparation of 6-methyl-1-[(3,4-dimethoxy-5-nitrophenyl)-methyl]-1,2,3,4-tetrahydro-9H-pyrido[3,4-b]indole hydrochloride

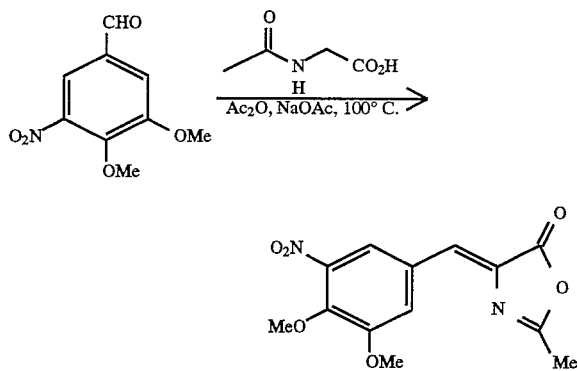

Azalactone (16.9 g) was prepared as in Example 21 except using 3,4-dimethoxy-5-nitrobenzaldehyde (23.5 g).

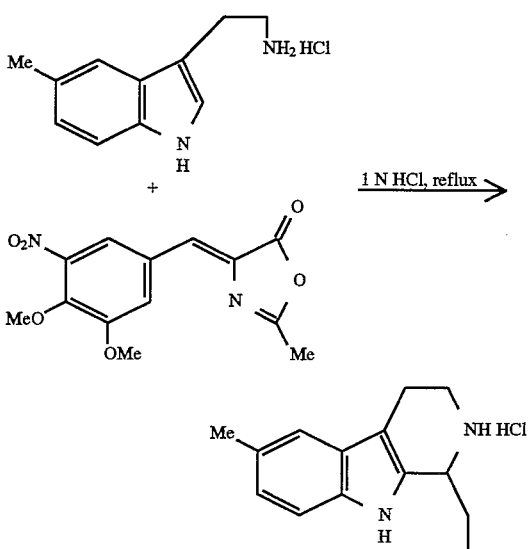

A suspension of azalactone (prepared above) (2.8 g, 9.6 mmol.) and 5-methyltryptamine hydrochloride (2.0 g, 9.5 mmol.) in 1N HCl (50 mL) was heated to reflux for 72 hours under nitrogen atmosphere. The reaction mixture was cooled to ambient temperature and the crude product isolated by filtration. The solid was triturated with isopropanol and washed with diethyl ether. The product was isolated as the hydrochloride salt by filtration (3.44) mp. 239°–243° C., m/e=381.

| Analysis | Calculated | Found |
|---|---|---|
| C | 60.36 | 60.54 |
| H | 5.79 | 5.66 |
| N | 10.06 | 10.12 |

EXAMPLE 29

Preparation of 6-methyl-1-[(3-iodo-4,5-dimethoxy-phenyl)-methyl]-1,2,3,4-tetrahydro-9H-pyrido[3,4-b]indole

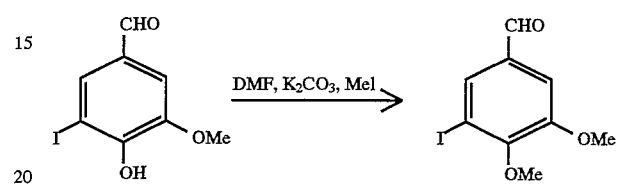

To a stirred, cooled (0° C.) solution of iodovanillin (10.0 g, 35.96 mmol.) in dimethylformamide (50 mL) was added anhydrous potassium carbonate (20.0 g, 143.86 mmol.) followed by iodomethane (3.11 mL, 50.0 mmol.). The mixture was allowed to warm to ambient temperature and stir for 14 H. The mixture was poured into diethyl ether (500 mL) and washed with water (3×150 mL). The organic phase was dried over $MgSO_4$ and concentrated under reduced pressure to afford 3-iodo-4,5-dimethoxybenzaldehyde (9.5 g) as a yellow oil which solidified upon standing and was used without further purification.

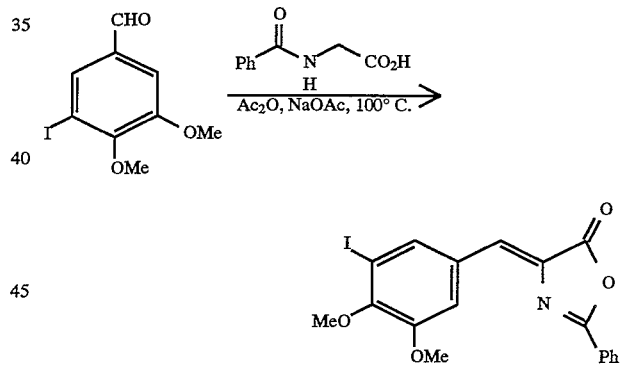

Azalactone (11.1 g) was prepared as in Example 21 except using 3-iodo-4,5-dimethoxybenzaldehyde (9.5 g), and hippuric acid (6.41 g) instead of N-acetylglycine.

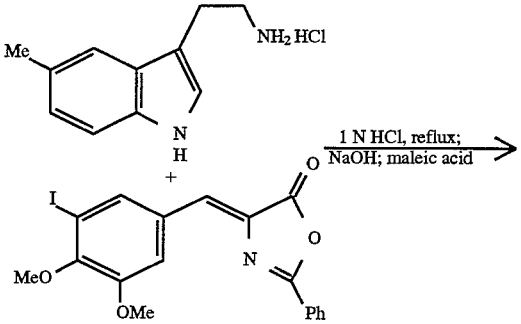

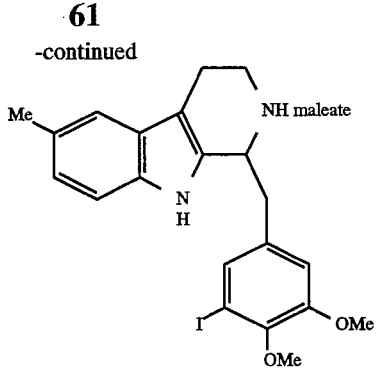

A suspension of azalactone (prepared above) (2.2 g, 5.0 mmol.) and 5-methyltryptamine hydrochloride (1.0 g, 4.3 mmol.) in 1N HCl (100 mL) was heated to reflux for 48 hours under nitrogen atmosphere. The reaction mixture was cooled to ambient temperature, neutralized with saturated aqueous sodium hydroxide solution and extracted with chloroform. The combined organic layers were concentrated under reduced pressure and the residue chromatographed on silica gel (ethyl acetate/0.2% $NH_4OH$ as eluent). The fractions containing product were pooled and concentrated under reduced pressure. The residue was dissolved in ethyl acetate containing 1% methanol and treated with maleic acid. The product was isolated as the maleate salt (134 mg) by filtration. m/e=463.

| Analysis | Calculated | Found |
|---|---|---|
| C | 51.92 | 52.15 |
| H | 4.71 | 4.72 |
| N | 4.84 | 4.70 |

EXAMPLE 30

Preparation of 6-methyl-1-[(3,4-dimethoxy-5-aminophenyl)-methyl]-1,2,3,4-tetrahydro-9H-pyrido[3,4-b]indole dihydrochloride

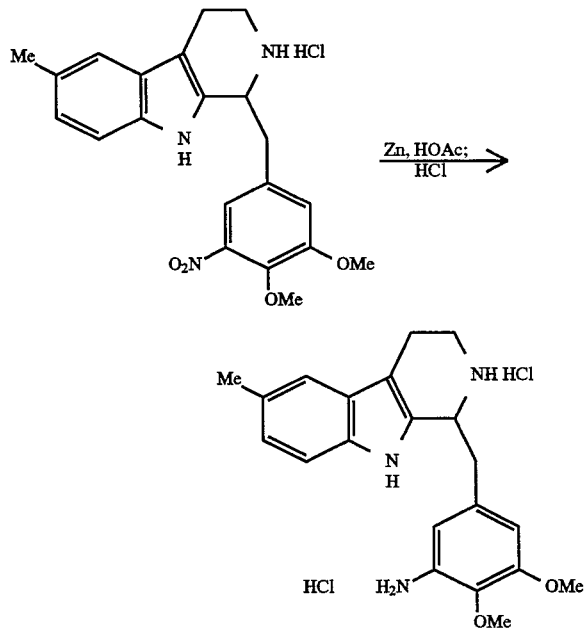

To a stirred solution of nitro compound (prepared in Example 28) (3.0 g, 7.2 mmol.) in acetic acid (40 mL) was added activated zinc dust (4.64 g). The reaction mixture was stirred at ambient temperature for 2 H, diluted with water (200 mL) and filtered through celite. The filtrate was neutralized with aqueous ammonium hydroxide solution and extracted with chloroform. The organic phase was washed with brine and dried over magnesium sulfate. The combined organic phases were concentrated under reduced pressure and the residue dissolved in ethyl acetate and treated with anhydrous HCl. The product was isolated by filtration, washing with diethyl ether and trituration with ethyl acetate to afford product as the bis-hydrochloride salt (2.41 g).mp. 230°–234° C., m/e=351.

| Analysis | Calculated | Found |
|---|---|---|
| C | 59.44 | 58.47 |
| H | 6.41 | 6.31 |
| N | 9.90 | 9.68 |

EXAMPLE 31

Preparation of 6-methyl-1-[(3-methoxy-4-propoxyphenyl)-methyl]-1,2,3,4-tetrahydro-9H-pyrido[3,4-b]indole

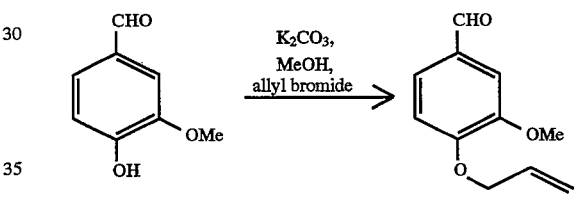

To a stirred solution of vanillin (30.0 g, 197 mmol.) in methanol (100 mL) was added anhydrous potassium carbonate (13.7 g, 99 mmol.) followed by allyl bromide (17.0 mL, 197 mmol.). The mixture was heated to reflux for 5 H. The reaction mixture was filtered and concentrated under reduced pressure to afford the intermediate product (30.4 g) as an oily solid which was used without further purification.

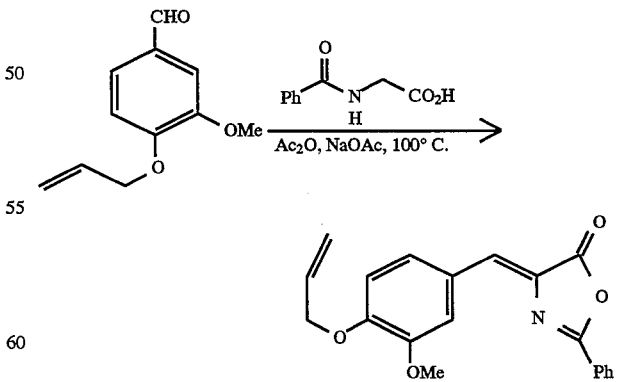

Azalactone (32.2 g) was prepared as in Example 21 except using 3-methoxy-4-allyloxybenzaldehyde (30.4 g), and hippuric acid (28.3 g) instead of N-acetyl glycine.

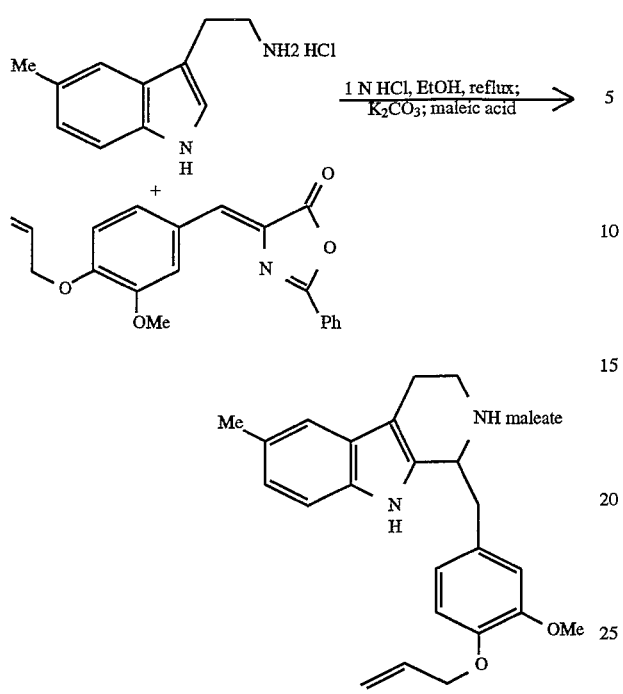

A suspension of azalactone (prepared above) (1.74 g, 5.2 mmol.) and 5-methyltryptamine hydrochloride (1.1 g, 5.2 mmol.) in 1N HCl (40 mL) and ethanol (30 mL) was heated to reflux for 18 hours under nitrogen atmosphere. The reaction mixture was cooled to ambient temperature, neutralized with saturated aqueous potassium carbonate solution and extracted with chloroform. The combined organic phases were concentrated under reduced pressure and the residue chromatographed on silica gel (ethyl acetate/0.2% NH₄OH as eluent). The fractions containing product were pooled and concentrated under reduced pressure. The residue was dissolved in ethyl acetate containing 1% methanol and treated with maleic acid. The product was isolated as the maleate salt (560 mg) by filtration. m/e=362. The product was used without further purification.

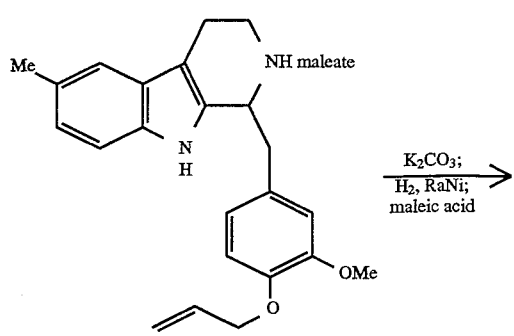

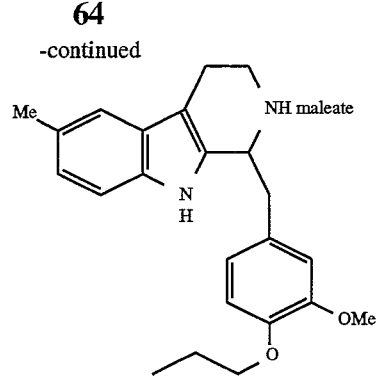

To a suspension of maleate salt (560 mg, 1.7 mmol.) in chloroform (100 mL) was added saturated potassium carbonate solution (100 mL) with vigorous stirring. The layers were separated and the aqueous phase was further extracted with chloroform (2×100 mL). The combined organic phases were dried over anhydrous sodium sulfate and concentrated under reduced pressure. The free base was dissolved in ethanol and hydrogenated (25° C., 60 PSI) in the presence of raney nickel catalyst. The catalyst was removed by filtration and the solution concentrated under reduced pressure to afford a viscous oil, which was dissolved in ethyl acetate and treated with maleic acid (140 mg). The crude product was isolated by filtration. Trituration with hot ethyl acetate and washing with diethyl ether afforded product (170 mg) as the maleate salt. mp. 188° C., m/e=365.

| Analysis | Calculated | Found |
|---|---|---|
| C | 67.48 | 67.62 |
| H | 6.71 | 6.66 |
| N | 5.83 | 5.80 |

EXAMPLE 32

Preparation of 6-methyl-1-[(4-dimethylaminophenyl)methyl]-1,2,3,4-tetrahydro-9H-pyrido[3,4-b]indole dihydrochloride

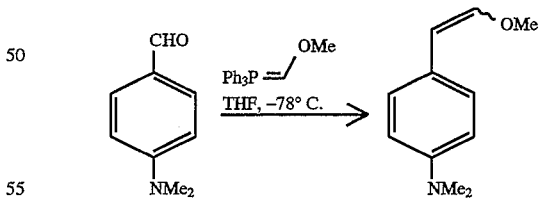

To a stirred, cooled (-78° C.) suspension of methoxymethyltriphenylphosphonium chloride (13.79 g, 40.02 mmol.) in dry THF (150 mL) was added n-BuLi solution (25.2 mL. 1.6M, 40.02 mmol.) dropwise by syringe. The orange suspension was stirred at -78° C. for 15 min. A solution of 4-dimethylaminobenzaldehyde (5.00 g, 3.35 mmol.) in THF (75 mL) was added to the ylide dropwise over 10 min. The reaction mixture was gradually warmed to ambient temperature and stirred 14 H. Saturated ammonium chloride solution (100 mL) was added and the mixture extracted with diethyl ether (3×50 mL). The combined organic phases were dried over sodium sulfate and concentrated under reduced pressure. Chromatography on silica gel, eluting with 15% ethyl acetate/hexanes afforded product (4.70 g) as a mixture of olefin isomers which was used without further purification.

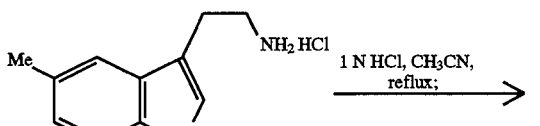

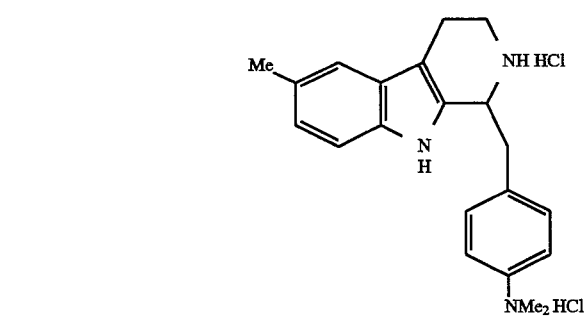

A mixture of 5-methyltryptamine hydrochloride (891 mg, 4.23 mmol.) and 1-methoxy-4'-dimethylaminostyrene (1.00 g, 5.64 mmol.) in acetonitrile (20 mL) and 1N HCl solution (150 mL) was heated to reflux for 96 H. The reaction mixture was cooled to ambient temperature, neutralized with saturated aqueous potassium carbonate solution and extracted with chloroform. The combined organic phases were concentrated under reduced pressure and the residue chromatographed on silica gel (2.5% MeOH/chloroform/ 0.2% NH₄OH as eluent). The fractions containing product were pooled and concentrated under reduced pressure. The residue was dissolved in ethyl acetate and treated with anhydrous HCl. The product was isolated as the dihydrochloride salt (354 mg) by filtration. mp. 275.4° C.

| Analysis | Calculated | Found |
|---|---|---|
| C | 64.28 | 64.21 |
| H | 6.94 | 7.01 |
| N | 10.71 | 10.74 |

EXAMPLE 33

Preparation of 6-methyl-1-[(4-dibutylaminophenyl)methyl] -1,2,3,4-tetrahydro-9H-pyrido[3,4-b]indole dihydrochloride

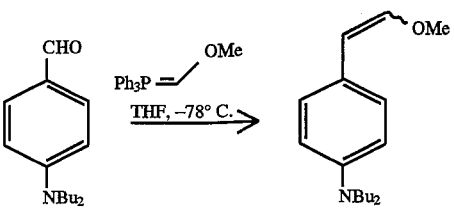

To a stirred, cooled (−78° C.) suspension of methoxymethyl-triphenylphosphonium chloride (8.81 g, 25.7 mmol.) in dry THF (150 mL) was added n-BuLi solution (16.1 mL. 1.6M, 25.7 mmol.) dropwise by syringe. The orange suspension was stirred at −78° C. for 15 min. A solution of 4-dibutylaminobenzaldehyde (5.00 g, 2.14 mmol.) in THF (75 mL) was added to the ylide dropwise over 10 min. The reaction mixture was gradually warmed to ambient temperature and stirred 14 H. Saturated ammonium chloride solution (100 mL) was added and the mixture extracted with diethyl ether (3×50 mL). The combined organic phases were dried over sodium sulfate and concentrated under reduced pressure. Chromatography on silica gel, eluting with 15% ethyl acetate/hexanes afforded product (3.47 g) as a mixture of olefin isomers which was used without further purification.

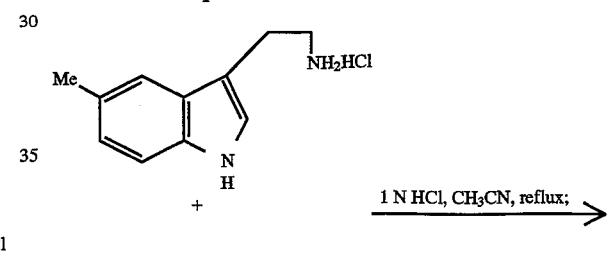

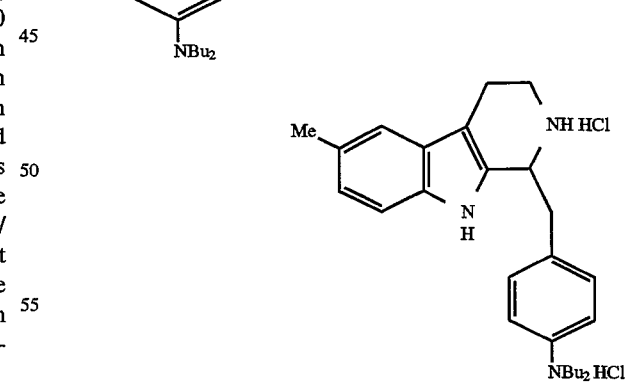

A mixture of 5-methyltryptamine hydrochloride (605 mg, 2.87 mmol.) and 1-methoxy-4'-dibutylamino-styrene (1.00 g, 3.83 mmol.) in acetonitrile (20 mL) and 1N HCl solution (150 mL) was heated to reflux for 96 H. The reaction mixture was cooled to ambient temperature, neutralized with saturated aqueous potassium carbonate solution and extracted with chloroform. The combined organic phases were concentrated under reduced pressure and the residue chromatographed on silica gel (2.5% MeOH/chloroform/ 0.2% NH₄OH as eluent). The fractions containing product were pooled and concentrated under reduced pressure. The residue was dissolved in ethyl acetate and treated with anhydrous HCl. The product was isolated as the dihydrochloride salt (476 mg) by filtration. mp. 266.6° C.

| Analysis | Calculated | Found |
|---|---|---|
| C | 68.05 | 67.92 |
| H | 8.25 | 8.22 |
| N | 8.82 | 8.74 |

EXAMPLE 34

Preparation of 6-methyl-1-[(3-fluoro-4-methoxyphenyl)-methyl]-1,2,3,4-tetrahydro-9H-pyrido[3,4-b]indole hydrochloride

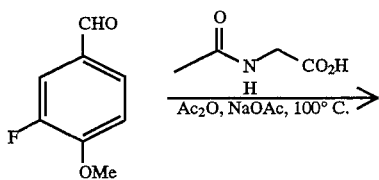

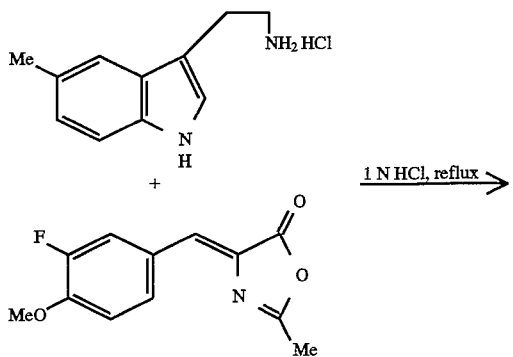

Azalactone (0.330 g) was prepared as in Example 21 except using 3-fluoro-4-methoxybenzaldehyde (5.0 g).

A suspension of azalactone prepared above (0.30 g, 1.3 mmol.) and 5-methyltryptamine hydrochloride (0.27 g, 1.3 mmol.) in 1N HCl (20 mL) was heated to reflux for 24 hours under nitrogen atmosphere. The reaction mixture was cooled to ambient temperature neutralized with saturated aqueous potassium carbonate solution and extracted with chloroform. The combined organic phases were concentrated under reduced pressure and the residue chromatographed on silica gel (ethyl acetate/0.2% NH₄OH as eluent). The fractions containing product were pooled and concentrated under reduced pressure. The residue was dissolved in ethyl acetate containing 1% methanol and treated with anhydrous HCl. The product was isolated as the hydrochloride salt (170 mg) by filtration. m/e=324.

| Analysis | Calculated | Found |
|---|---|---|
| C | 66.57 | 66.37 |
| H | 6.15 | 6.16 |
| N | 7.76 | 7.5 |

EXAMPLE 35

Preparation of 6-methyl-1-[(3,4-dimethylphenyl)methyl]-1,2,3,4-tetrahydro-9H-pyrido[3,4-b]indole hydrochloride

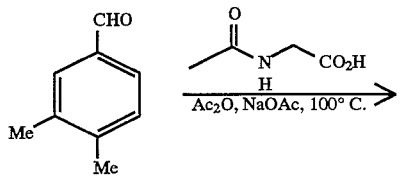

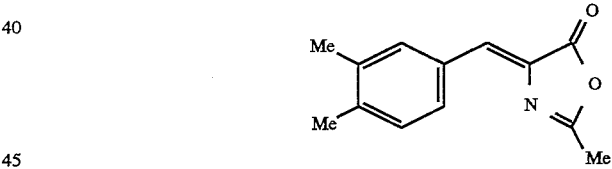

Azalactone (11.3 g) was prepared as in Example 21 except using 3,4-dimethylbenzaldehyde (25.0 g).

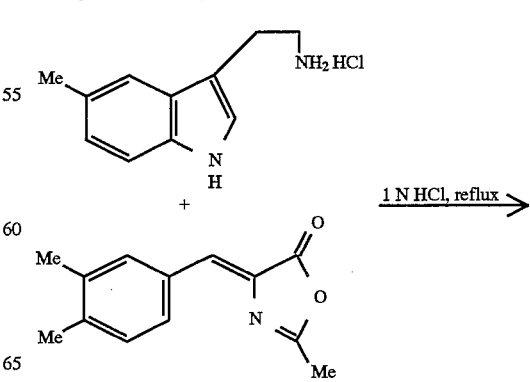

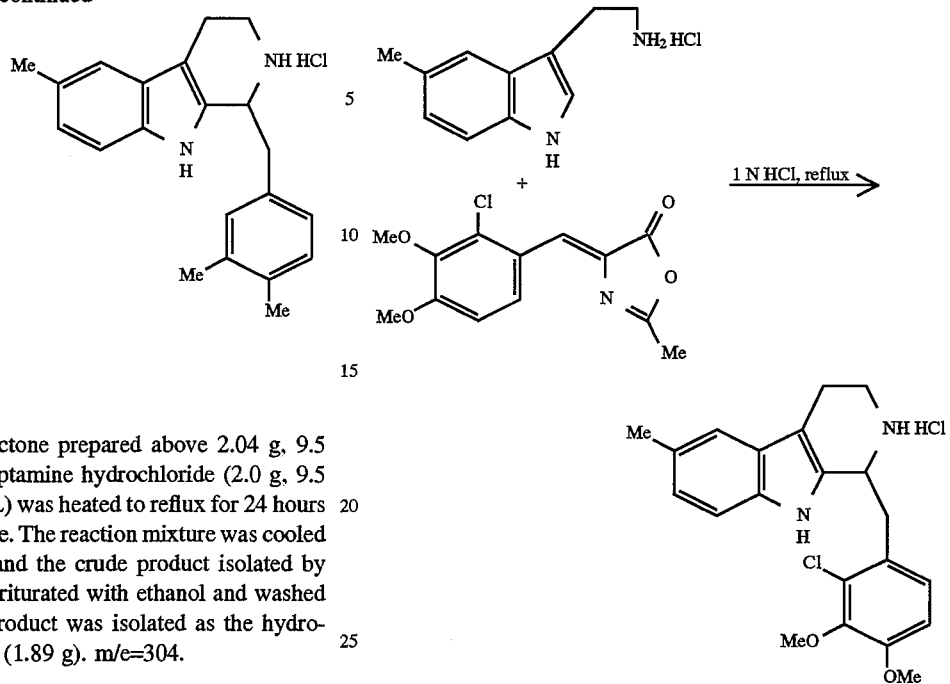

A suspension of azalactone prepared above 2.04 g, 9.5 mmol.) and 5-methyl-tryptamine hydrochloride (2.0 g, 9.5 mmol.) in 1N HCl (80 mL) was heated to reflux for 24 hours under nitrogen atmosphere. The reaction mixture was cooled to ambient temperature and the crude product isolated by filtration. The solid was triturated with ethanol and washed with diethyl ether The product was isolated as the hydrochloride salt by filtration (1.89 g). m/e=304.

| Analysis | Calculated | Found |
|---|---|---|
| C | 73.99 | 73.84 |
| H | 7.39 | 7.35 |
| N | 8.21 | 8.48 |

EXAMPLE 36

Preparation of 6-methyl-1-[(2-chloro-3,4-dimethoxyphenyl)-methyl]-1,2,3,4-tetrahydro-9H-pyrido[3,4-b]indole hydrochloride

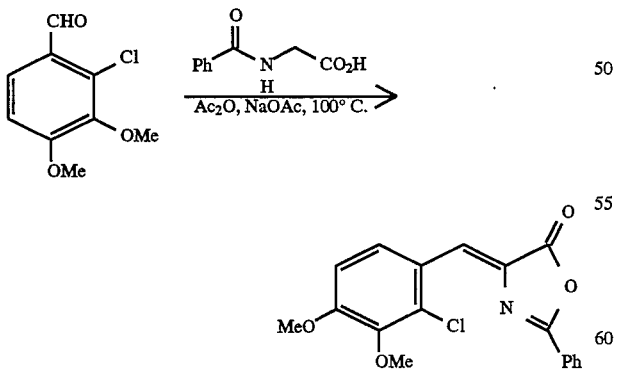

Azalactone (5.26g) was prepared as in Example 21 except using 2-chloro-3,4-dimethoxybenzaldehyde (10.45 g).

A suspension of azalactone prepared above (1.34 g, 4.76 mmol.) and 5-methyltryptamine hydrochloride (1.0 g, 4.75 mmol.) in 1N HC1 (30 mL) was heated to reflux for 24 hours under nitrogen atmosphere. The reaction mixture was cooled to ambient temperature and the crude product isolated by filtration. The solid was triturated with ethanol and washed with diethyl ether. The product was isolated by filtration (1.19 g). m/e=370, mp. 244° C. (dec.).

| Analysis | Calculated | Found |
|---|---|---|
| C | 61.92 | 61.67 |
| H | 5.94 | 5.94 |
| N | 6.88 | 6.94 |

EXAMPLE 37

Preparation of 6-methyl-1-[(2-chloro-3-methoxy-4-hydroxyphenyl)methyl]-1,2,3,4-tetrahydro-9H-pyrido[3,4-b]-indole hydrochloride

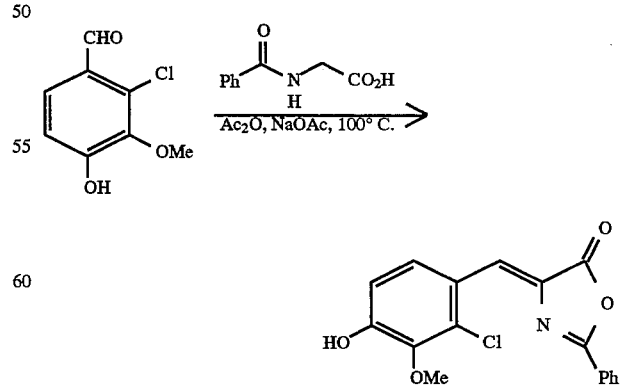

Azalactone (12.4 g) was prepared as in Example 21 except using 2-chloro-3-methoxy-4-hydroxybenzaldehyde (12.0 g).

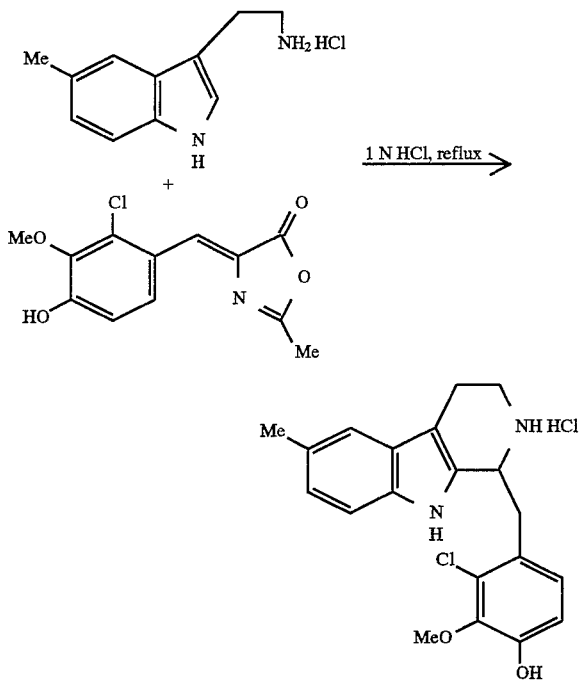

A suspension of azalactone prepared above (1.29 g, 4.82 mmol.) and 5-methyl-tryptamine hydrochloride (1.0 g, 4.75 mmol.) in 1N HCl (30 mL) was heated to reflux for 24 hours under nitrogen atmosphere. The reaction mixture was cooled to ambient temperature and the crude product isolated by filtration. The solid was triturated with ethanol and washed with diethyl ether. The product was isolated by filtration (1.07 g). mp. 240° C. (dec.).

| Analysis | Calculated | Found |
| --- | --- | --- |
| C | 61.07 | 60.83 |
| H | 5.64 | 5.71 |
| N | 7.12 | 7.03 |

EXAMPLE 38

Preparation of 5-fluoro-6-methyl-1-[(2-chloro-3,4-dimethoxyphenyl)methyl]-1,2,3,4-tetrahydro-9H-pyrido[3,4-b]indole hydrochloride

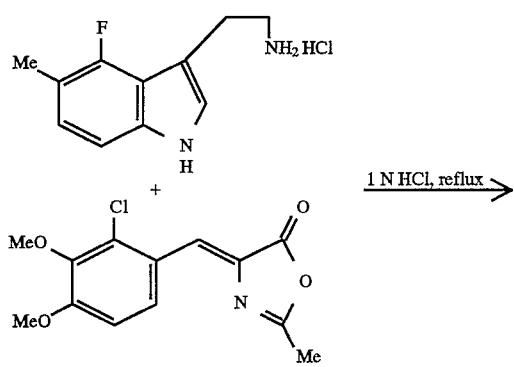

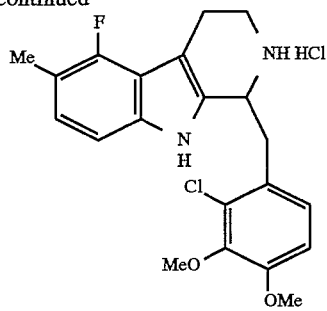

A suspension of azalactone (prepared in Example 36) (2.15 g, 7.63 mmol.) and 4-fluoro-5-methyl-tryptamine hydrochloride (prepared in Example 9 (1.0 g, 4.75 mmol.) in 1N HCl (80 mL) was heated to reflux for 24 hours under nitrogen atmosphere. The reaction mixture was cooled to ambient temperature and the crude product isolated by filtration. The solid was triturated with ethanol and washed with diethyl ether. The product was isolated as the hydrochloride salt by filtration (1.39 g). m/e=388.

| Analysis | Calculated | Found |
| --- | --- | --- |
| C | 59.30 | 59.58 |
| H | 5.45 | 5.47 |
| N | 6.59 | 6.71 |

EXAMPLE 39

Preparation of 6-methyl-1-(cyclohexylmethyl)-1,2,3,4-tetrahydro-9H-pyrido[3,4-b]indole hydrochloride

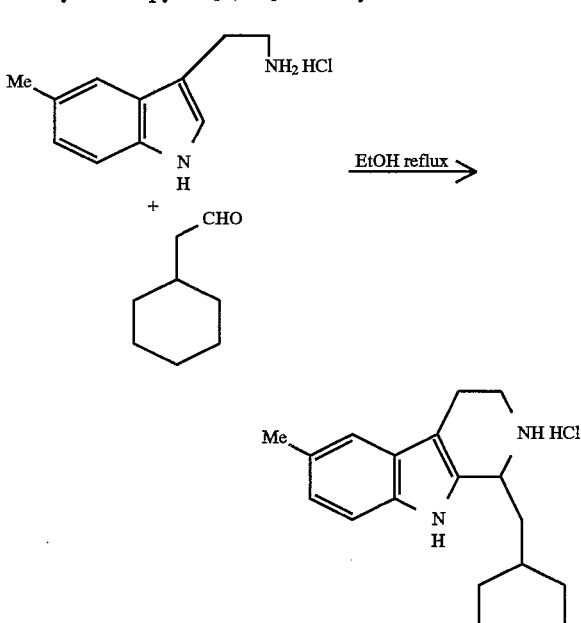

A suspension of cyclohexylacetaldehyde (631 mg, 5.0 mmol.) and 5-methyltryptamine hydrochloride (1.0 g, 4.3 mmol.) in ethanol (20 mL) was heated to reflux for 36 hours under nitrogen atmosphere. The reaction mixture was cooled to ambient temperature and the crude product isolated by filtration. The solid was triturated with ethanol and washed with diethyl ether. The product was isolated by filtration (731 mg). m/e=282, mp 230° C.

| Analysis | Calculated | Found |
|----------|-----------|-------|
| C | 71.56 | 71.27 |
| H | 8.53 | 8.56 |
| N | 8.78 | 8.64 |

EXAMPLE 40

Preparation of (±) 6-methyl-1-[(3,4-dimethoxyphenyl)-1-ethyl]-1,2,3,4-tetrahydro-9H-pyrido[3,4-b]indole (Z)-2-butenedioate

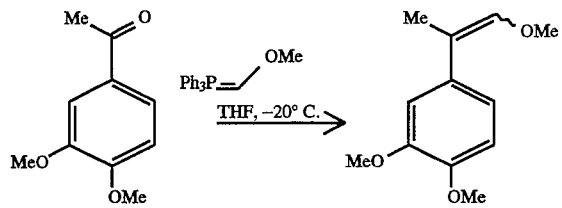

To a stirred, cooled (−20° C.) suspension of methoxymethyltriphenylphosphonium chloride (118.9 g, 347 mmol.) in dry THF (2000 mL) was added potassium t-butoxide (39.3 g, 350 mmol.) in portions. The orange suspension was stirred at −20° C. for 30 min. A solution of 3,4-dimethoxyacetophenone (50.0 g, 275 mmol.) in THF (500 mL) was added to the ylide dropwise over 30 min. The reaction mixture was gradually warmed to ambient temperature and stirred 2 H. Saturated ammonium chloride solution (500 mL) was added and the mixture extracted with diethyl ether (3×50 mL). The combined organic phases were dried over sodium sulfate and concentrated under reduced pressure. Chromatography on silica gel, eluting with 15% ethyl acetate/hexanes afforded product (48.4 g) as a mixture of olefin isomers which was used without further purification.

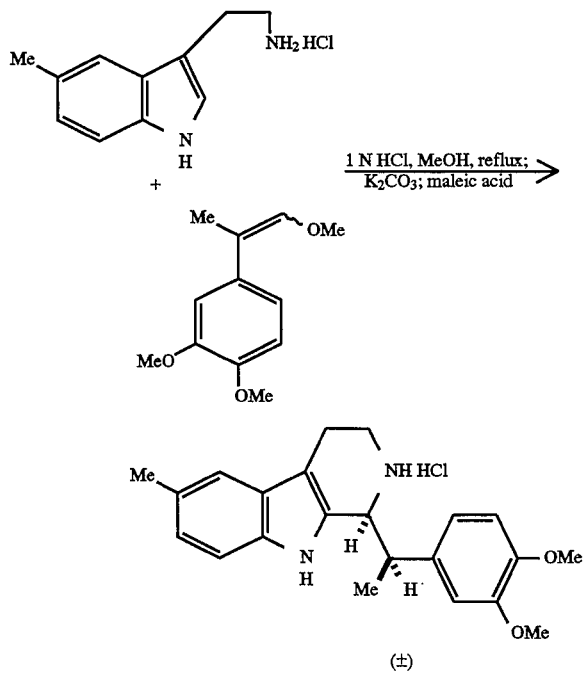

A mixture of 5-methyltryptamine hydrochloride (2.16 g, 10.3 mmol.) and 1-methoxy-2-methyl-3',4'-dimethoxystyrene (prepared above) (2.13 g, 10.3 mmol.) in methanol (12 mL) and 1N HCl solution (108 mL) was heated to reflux for 96 H. The reaction mixture was cooled to ambient temperature, neutralized with saturated aqueous potassium carbonate solution and extracted with chloroform. The combined organic phases were concentrated under reduced pressure and the residue chromatographed on silica gel (2.5% MeOH/chloroform/0.2% NH₄OH as eluent). The fractions containing product (upper diastereomer) were pooled and concentrated under reduced pressure. The residue was dissolved in ethyl acetate and treated with maleic acid. The product was isolated as the maleate salt (260 mg) by filtration. mp. 187°1∝190° C.

| Analysis | Calculated | Found |
|----------|-----------|-------|
| C | 66.94 | 66.95 |
| H | 6.48 | 6.35 |
| N | 6.00 | 5.81 |

EXAMPLE 41

Preparation of (±) 6,7-dimethyl-1-[(3,4-dimethoxyphenyl)-1-ethyl]-1,2,3,4-tetrahydro-9H-pyrido[3,4-b]indole (Z)-2-butenedioate

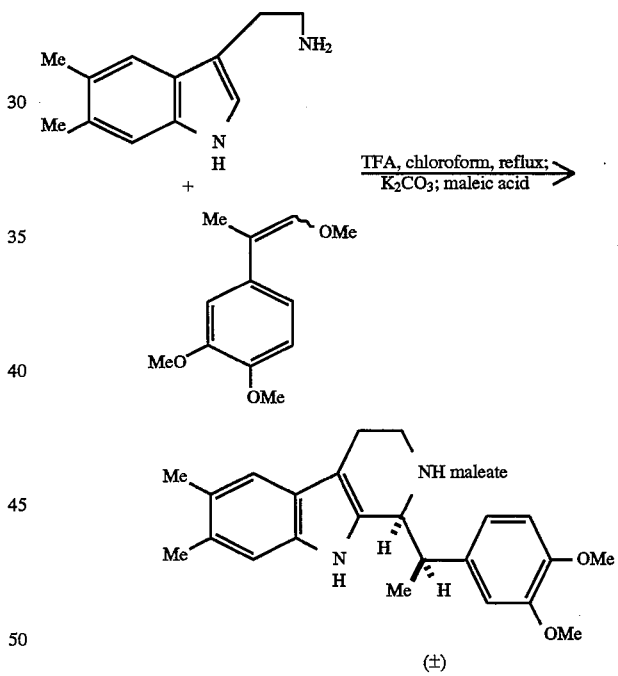

5,6-dimethyltryptamine hydrochloride (prepared in Example 16) (1.60 g, 7.12 mmol.) was converted to its free base with aqueous potassium carbonate in chloroform. This solution was dried and treated with 1-methoxy-2-methyl-3', 4'-dimethoxystyrene (prepared above in Example 40) (1.49 g, 7.14 mmol.) and trifluororacetic acid (1.62 g, 14.2 mmol) and was heated to reflux for 96 H. The reaction mixture was cooled to ambient temperature, neutralized with saturated aqueous potassium carbonate solution and extracted with chloroform. The combined organic phases were concentrated under reduced pressure and the residue chromatographed on silica gel (2.5% MeOH/chloroform/0.2% NH₄OH as eluent). The fractions containing product (upper diastereomer) were pooled and concentrated under reduced pressure. The residue was dissolved in ethyl acetate and treated with maleic acid. The product was isolated as the maleate salt (560 mg) by filtration. m/e=364. mp. 177° C. (dec.).

| Analysis | Calculated | Found |
|---|---|---|
| C | 67.48 | 67.34 |
| H | 6.71 | 6.68 |
| N | 5.83 | 5.74 |

EXAMPLE 42

Preparation of (±) 6-ethyl-1-[(3,4-dimethoxyphenyl)-1-ethyl]-1,2,3,4-tetrahydro-9H-pyrido[3,4-b]indole (Z)-2-butenedioate

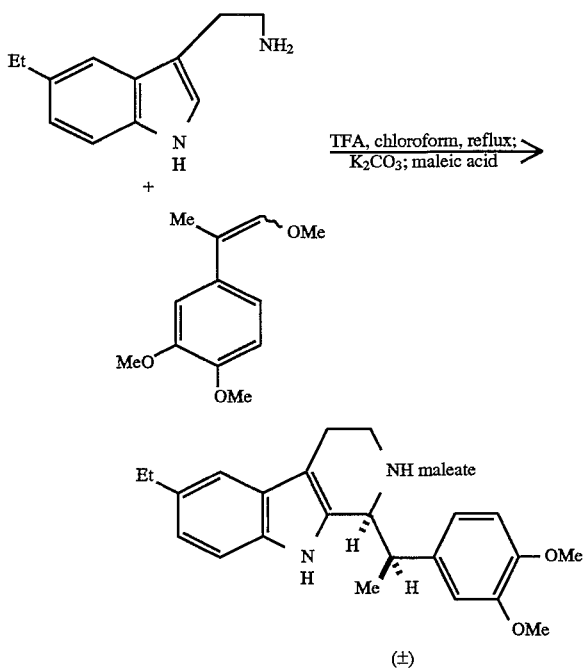

5-ethyltryptamine hydrochloride (prepared in Example 17) (2.0 g, 8.9 mmol.) was converted to its free base with aqueous potassium carbonate in chloroform. This solution was dried and treated with 1-methoxy-2-methyl-3',4'-dimethoxystyrene (prepared above in Example 40) (1.86 g, 8.9 mmol.) and trifluroracetic acid (2.03 g, 17.8 mmol) and was heated to reflux for 96 H. The reaction mixture was cooled to ambient temperature, neutralized with saturated aqueous potassium carbonate solution and extracted with chloroform. The combined organic phases were concentrated under reduced pressure and the residue chromatographed on silica gel (2.5% MeOH/chloroform/0.2% NH$_4$OH as eluent). The fractions containing product (upper diastereomer) were pooled and concentrated under reduced pressure. The residue was dissolved in ethyl acetate and treated with maleic acid. The product was isolated as the maleate salt (430 mg) by filtration. m/e=364. mp. 192°–194° C. (dec.).

| Analysis | Calculated | Found |
|---|---|---|
| C | 67.48 | 67.32 |
| H | 6.71 | 6.72 |
| N | 5.83 | 5.76 |

EXAMPLE 43

Preparation of (±) 6-methyl-1-[(3,4-dimethoxyphenyl)-1-propyl]-1,2,3,4-tetrahydro-9H-pyrido[3,4-b]indole (Z)-2-butenedioate

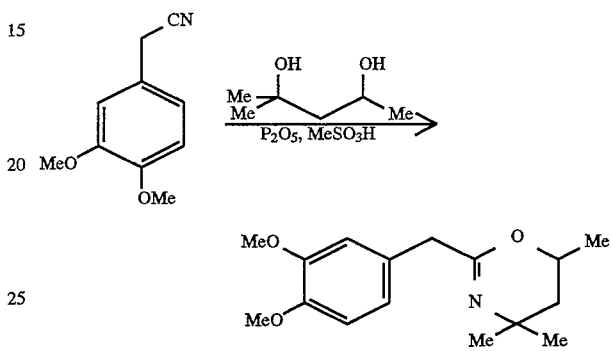

To methanesulfonic acid (203 mL) was added phosphorus pentoxide (30.0 g) slowly with stirring. After the addition was complete, the mixture was further stirred under nitrogen atmosphere for 2 hours until homogenous. To this solution was added 3,4-dimethoxyphenylacetonitrile (50 g, 0.28 mol.) in a single portion, followed by 2-methyl-2,4-pentanediol (72.1 mL, 0.56 mol.) dropwise at such a rate as to maintain a temperature between 25° and 30° C. (1 hour). After complete addition, the reaction mixture was stirred at ambient temperature for 10 hours and poured onto ice (500 g). The mixture was made basic with sodium hydroxide solution (50%), added at such a rate as to keep the temperature below 35° C. The mixture was extracted with diethyl ether (3×250 mL) and the combined organic phases were dried over magnesium sulfate and concentrated under reduced pressure to afford a green solid. Distillation (Kugelrohr) afforded intermediate product (27.7 g) which was used without further purification.

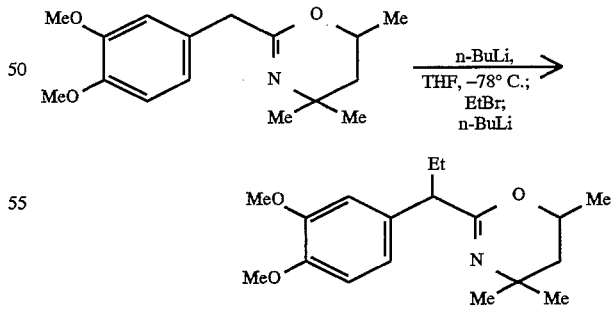

To a stirred, cool (−78° C.) solution of previously prepared intermediate product (27.2 g, 0.106 mol.) in THF (400 mL) under argon atmosphere was added n-butyllithium solution (68.7 mL, 1.6M in hexanes, 0.11 mol.) dropwise via syringe over 15 minutes. After complete addition, the orange solution was stirred at −78° C. for 30 minutes. Ethyl bromide (8.18 mL, 0.10 mol.) was added dropwise via syringe and the resulting solution further stirred at −78° C. for 45 minutes. n-Butyllithium (68.7 mL, 1.6M in hexanes, 0.11 mol.) was added dropwise over 15 minutes and the orange solution stirred for 2 hours. The mixture was poured into ice/water (500 mL) and was acidified to pH 2–3 with 5N HCl solution. The mixture was extracted with diethyl ether (2×100 mL) and these extracts were discarded. The aqueous phase was made basic with sodium hydroxide solution (50%), cooling the mixture with ice when necessary. The basic aqueous phase was extracted with diethyl ether (2×200 mL) and the combined organic extracts were dried over magnesium sulfate, filtered and concentrated to afford product as an oily solid (12.08 g), which was used without further purification.

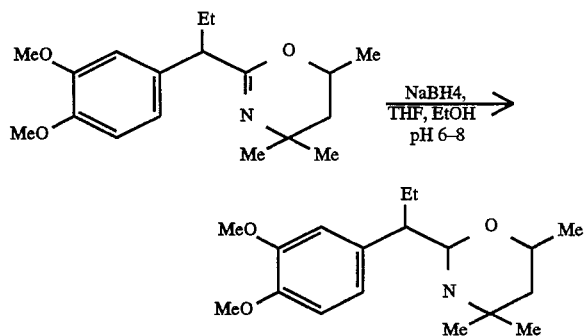

To a stirred cooled −40° C.) solution of previous product (12.0 g, 39.3 mmol.) in THF (90 mL) and ethyl alcohol (90 mL) was added 5N HCl solution until pH 7. In a separate flask, a solution of sodium borohydride (2.12 g, 55.4 mmol.) was dissolved in water (20 mL) to which 1 drop of 50% sodium hydroxide had been added. Portions of the sodium borohydride solution and 5N HCl solution were alternately added to the reaction mixture such that the pH remained 6–8, at such a rate as to maintain temperature between −35° and −45° C. After complete addition, the reaction mixture was warmed to ambient temperature over about 2 hours. The reaction mixture was made basic with sodium hydroxide solution and extracted with diethyl ether (3×100 mL). The combined organic phases were washed with brine and dried over magnesium sulfate. Filtration and removal of solvent afforded crude product (11.3 g) as a viscous oil, which was used without further purification.

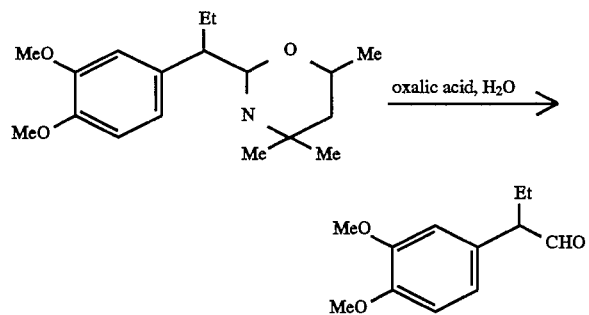

A mixture of crude product from the previous reaction (11.3 g, 36.8 mmol) and oxalic acid dihydrate (15.1 g, 120 mmol.) in water (300 mL) was heated to reflux for 12 hours. The mixture was cooled to ambient temperature and extracted with chloroform (2×100 mL). The combined organic phases were dried over magnesium sulfate, filtered and concentrated to afford aldehyde as an orange oil. Distillation (Kugelrohr) under reduced pressure afforded pure aldehyde (4.97 g) as a pale oil.

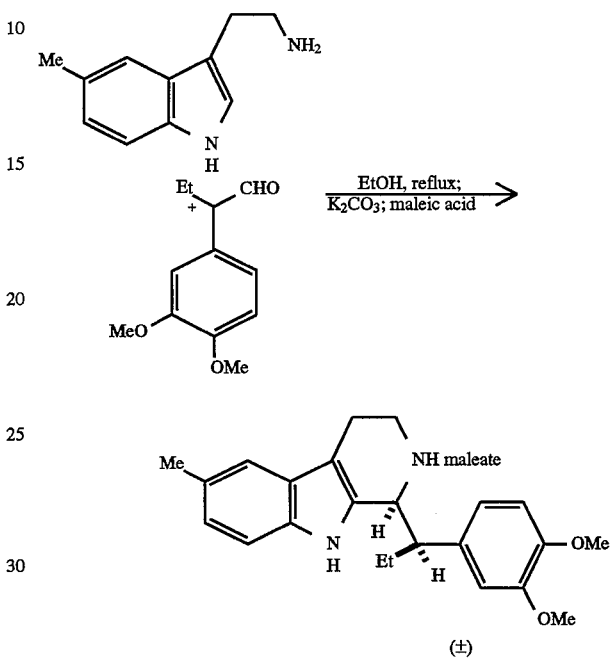

A mixture of 5-methyltryptamine hydrochloride (2.53 g, 12.0 mmol.) and 2-ethyl-3,4'-dimethoxyphenylacetaldehyde (prepared above) (2.49 g, 12.0 mmol.) in ethanol(30 mL) was heated to reflux for 48 H. The reaction mixture was cooled to ambient temperature, neutralized with saturated aqueous potassium carbonate solution and extracted with chloroform. The combined organic phases were concentrated under reduced pressure and the residue chromatographed on silica gel (2.5% MeOH/chloroform/0.2% NH$_4$OH as eluent). The fractions containing product (upper Rf diastereomer) were pooled and concentrated under reduced pressure. The residue was dissolved in ethyl acetate and treated with maleic acid. The product was isolated as the maleate salt (1.51 g) by filtration. m/e=364.

| Analysis | Calculated | Found |
|---|---|---|
| C | 67.48 | 67.35 |
| H | 6.71 | 6.96 |
| N | 5.83 | 5.77 |

EXAMPLE 44

Preparation of 2,6-dimethyl-1-[(2-chloro-3,4-dimethoxyphenyl)methyl]-1,2,3,4-tetrahydro-9H-pyrido[3,4-b]indole hydrochloride

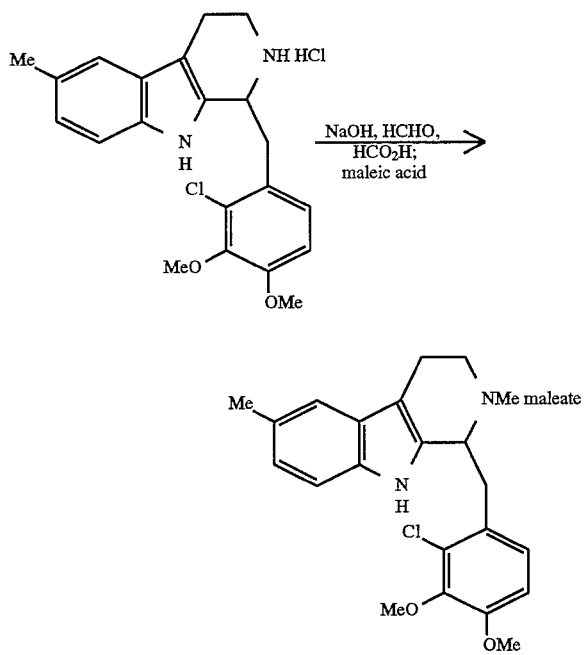

An aqueous solution of 6-methyl-1-[(2-chloro-3,4-dimethoxyphenyl)methyl]-1,2,3,4-tetrahydro-9H-pyrido[3,4-b]indole hydrochloride (Prepared in Example 36) (500 mg, 1.23 mmol.) was treated with sodium hydroxide (49 mg, 1.23 mmol.), followed by formic acid (0.91 mL) and aqueous formaldehyde solution (0.18 mL). The mixture was heated to reflux for 4 H. The reaction mixture was cooled to ambient temperature and concentrated under reduced pressure. The residue was partitioned between aqueous potassium carbonate solution and diethyl ether. The organic phase was dried over potassium carbonate and concentrated under reduced pressure. The residue was dissolved in ethyl acetate and treated with maleic acid. The maleate salt was isolated by filtration and purified by recrystallization from ethyl acetate/hexanes to afford product (240 mg). m/e=385.

| Analysis | Calculated | Found |
|---|---|---|
| C | 62.34 | 62.47 |
| H | 5.84 | 5.71 |
| N | 5.59 | 5.58 |

EXAMPLE 45

Preparation of 2-methyl-6-(1-methylethyl)-1,2,3,4-tetrahydro-1-[(3,4-dimethoxyphenyl)methyl]-9H-pyrido-[3,4b]indole maleate

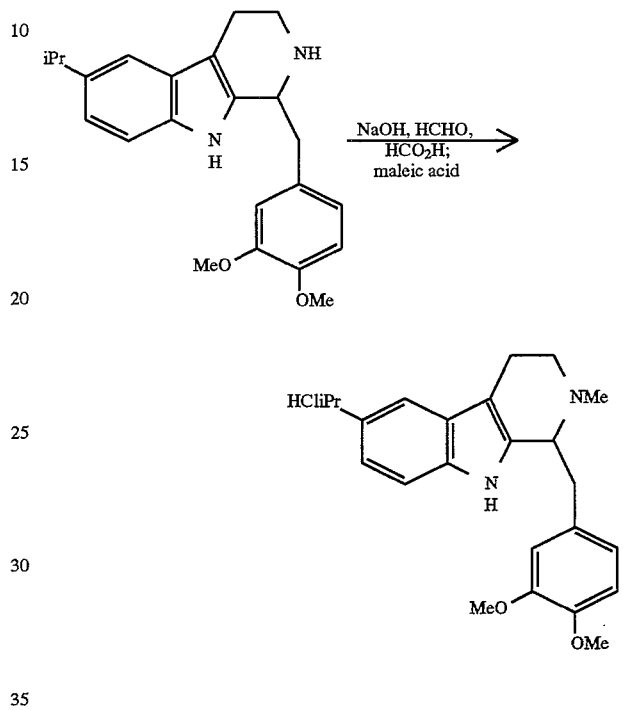

An aqueous solution of 6-(1-methylethyl)-1-[(3,4-dimethoxyphenyl)methyl]-1,2,3,4-tetrahydro-9H-pyrido[3,4-b]indole (Z)-2-butenedioate (prepared in Example 13) (500 mg, 1.04 mmol.) was treated with sodium hydroxide (83 mg, 2.08 mmol.), followed by formic acid (0.77 mL) and aqueous formaldehyde solution (0.15 mL). The mixture was heated to reflux for 4 H. The reaction mixture was cooled to ambient temperature, neutralized with saturated aqueous potassium carbonate solution and extracted with chloroform. The combined organic layers were concentrated under reduced pressure and the residue chromatographed on silica gel (ethyl acetate/0.2% NH$_4$OH as eluent). The fractions containing product were pooled and concentrated under reduced pressure. The residue was dissolved in ethyl acetate containing 1% methanol and treated with maleic acid. The product was isolated as the maleate salt (130 mg) by filtration. m/e=376.

| Analysis | Calculated | Found |
|---|---|---|
| C | 67.99 | 67.88 |
| H | 6.93 | 6.73 |
| N | 5.66 | 5.69 |

EXAMPLE 46

Preparation of (−)-(S)-6-methyl-1,2,3,4-tetrahydro-1-[(3,4-dimethylphenyl)methyl]-9H-pyrido[3,4-b]indole hydrochloride

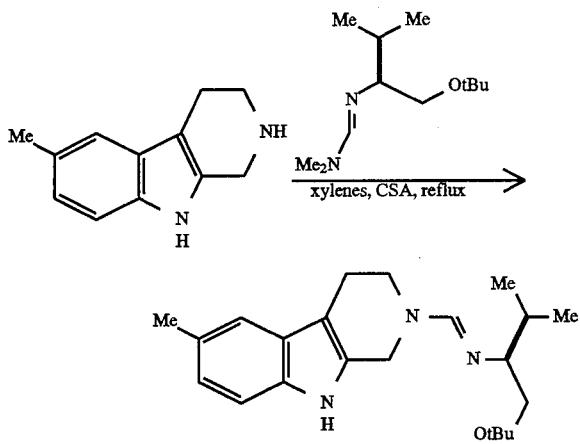

To a stirred solution of 6-methyl-1,2,3,4-tetrahydro-9H-pyrido[3,4-b]indole (3.14 g, 16.9 mmol.) in dry xylenes (65 mL) was added (S)-N,N-dimethyl-N'-(1-tert-butoxy-3-methyl)-2-butylformamidine (3.79 g , 17.7 mmol.) followed by camphorsulfonic acid (200 mg). The resulting solution was heated to reflux for 72 hours. The solution was cooled to ambient temperature and concentrated under reduced pressure. The residue was purified by flash chromatography on silica gel (1:3:6 triethylamine:ethyl acetate:hexanes as eluent). The product containing fractions were pooled and concentrated to afford the product formamidine (5.99 g) as a viscous oil which was used without further purification.

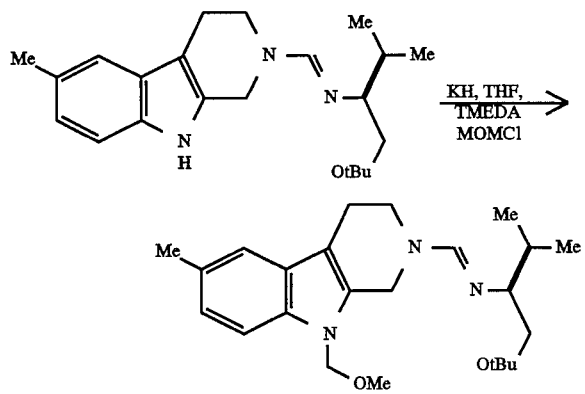

To a stirred, cooled (0° C.) suspension of potassium hydride (25% oil dispersion, 829 mg, 20.2 mmol.) in THF (10 mL) was added formamidine prepared above (5.99 g , 16.8 mmol.) in THF (45 mL). To this mixture was added tetramethylethylenediamine (3.0 mL, 20.2 mmol.) followed by chloromethylmethyl ether (1.9 mL, 25.2 mmol.). The mixture was stirred for an additional 1 hour and treated with water (50 mL). The mixture was partitioned between diethyl ether and water and the layers separated. The aqueous phase was extracted with diethyl ether (2×100 mL) and the organic phases combined, dried over potassium carbonate, and concentrated to afford product (6.73 g) as an orange oil, which was used without further purification.

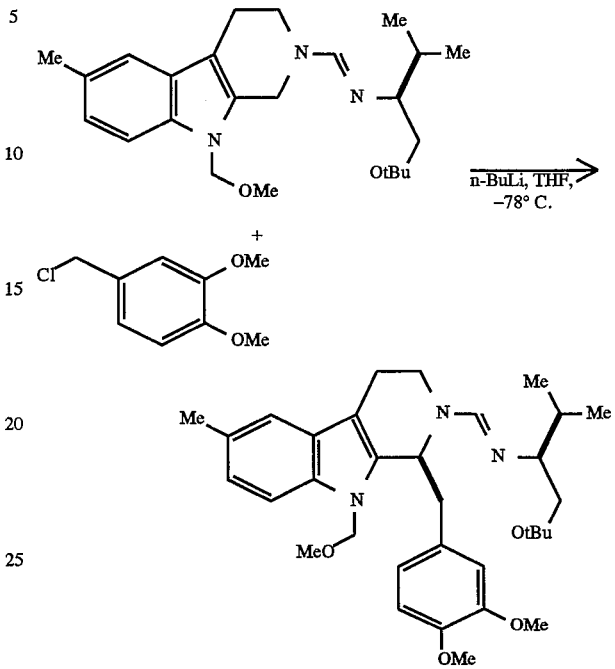

To a stirred, cooled (−78° C.) solution of previously prepared formamidine (6.29 g, 8.4 mmol.) in dry THF (100 mL) was added n-BuLi (1.7M solution in hexanes, 10.1 mL, 17.1 mmol.) dropwise over 5 minutes. The solution was further stirred at −78° C. solution for 1 hour and treated with 1-chloromethyl-3,4-dimethoxybenzene (3.35 g, 17.9 mmol.) in dry THF (15 mL). The solution was further stirred for 4 hours at −78° C. and allowed to warm to room temperature overnight. Wet THF was added (50 mL) and the solution was concentrated under reduced pressure. The residue was dissolved in chloroform and washed with water. The organic phase was dried over sodium carbonate and concentrated. The crude product was purified by flash chromatography on silica gel (1:3:6 triethylamine:ethyl acetate: hexanes as eluent). The product containing fractions (upper Rf) were pooled and concentrated to afford product (3.92 g) as a viscous oil (m/e=550) which was used without further purification.

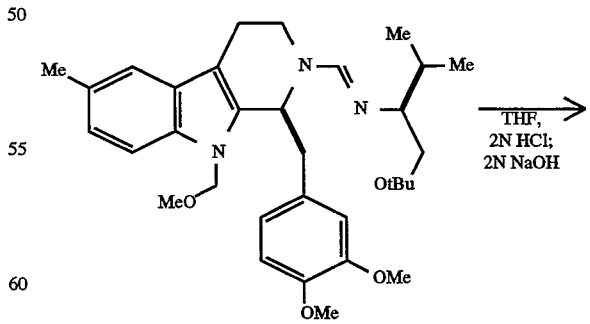

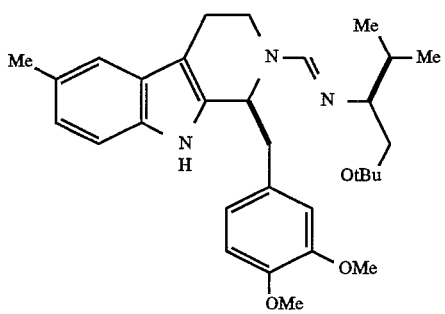

To a stirred solution of methoxymethylindole prepared above (3.92 g , 7.13 mmol.) in THF (70 mL) was added 2N HCl (20 mL). The mixture was stirred at ambient temperature for 24 hours, and partitioned between diethyl ether and water. The aqueous phase was back extracted with diethyl ether (2×50 mL) and the combined organic phases were washed with brine, dried over sodium carbonate, and concentrated under reduced pressure. The residue was dissolved in THF (20 mL) and treated with 2N sodium hydroxide solution (6 mL). After 2 hours, the reaction mixture was extracted with chloroform (2×100 mL). The organic phase was dried over sodium carbonate and concentrated. Chromatography on silica gel (1:3:6 triethylamine/ethyl acetate/hexanes as eluent) afforded product (1.85 g) as a viscous oil (m/e=505).

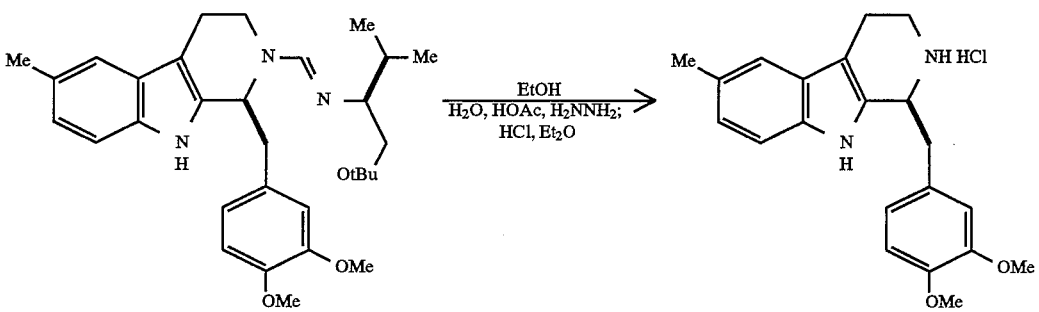

To a stirred, cooled (0° C.) solution of previously prepared formamidine (1.37 g, 5.41 mmol.) in ethanol (50 mL) was added water (6 mL) followed by acetic acid (6 mL) and hydrazine hydrate (11 mL). The reaction vessel was placed in the freezer (−10° C.) for 72 hours. The mixture was warmed to ambient temperature and concentrated under reduced pressure. The crude product was dissolved in chloroform (300 mL) and washed with water (3×50 mL). The organic phase was dried over sodium carbonate and concentrated to a viscous oil. The oil was dissolved in diethyl ether and treated with anhydrous HCl. The hydrochloride salt (560 mg) was isolated by filtration. Recrystallization from ethanol (2×) afforded material of constant rotation. Chiral HPLC confirmed enantiomeric purity as >98% ee. m/e=336) specific rotation @589 nM=−118.0 (pyridine, C=1) specific rotation @365 nM=−401.0 (pyridine, C=1)

| Analysis | Calculated | Found |
|---|---|---|
| C | 67.64 | 67.65 |
| H | 6.76 | 6.70 |
| N | 7.51 | 7.52 |

EXAMPLE 47

7-bromo-1H-indole-3-ethanamine

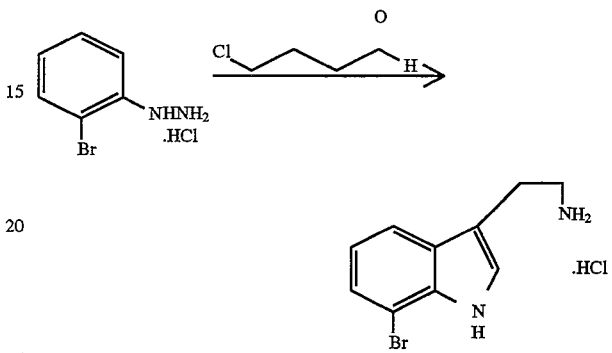

A 25.8 g sample of 2-bromophenylhydrazine hydrochloride was partitioned between 1N NaOH and chloroform. The organic layer was separated and the aqueous portion was extracted with chloroform. The combined organic extracts were dried (Na$_2$SO$_4$) and concentrated to yield the free hydrazine as an oil.

The oil was stirred in 100 mL of methanol while 4-chlorobutyraldehyde (12.3 g) was added. The resulting solution was transferred to a sealable tube and purged with nitrogen. The tube was sealed and the reaction mixture was heated in an oil bath maintained at 95° C. for 14 hours. The resulting mixture was allowed to cool and concentrated to a residue which was partitioned between iN NaOH and chloroform. The combined organic extracts were dried and concentrated to an oil. The oil was chromatographed on silica gel using a gradient of 0–10% methanol in chloroform. Fractions containing product were concentrated to an oil which was taken up in a small amount of methanol and added to ethereal HCl. A solid was collected, washed with diethyl ether and vacuum dried at 50° C.

Yield: 7.32 g %Yield: 23% M.P.: 260°–262° C. Elemental Analysis: C 43.55: H 4.41: N 10.03.

EXAMPLE 48

7-fluoro-1H-indole-3-ethanamine

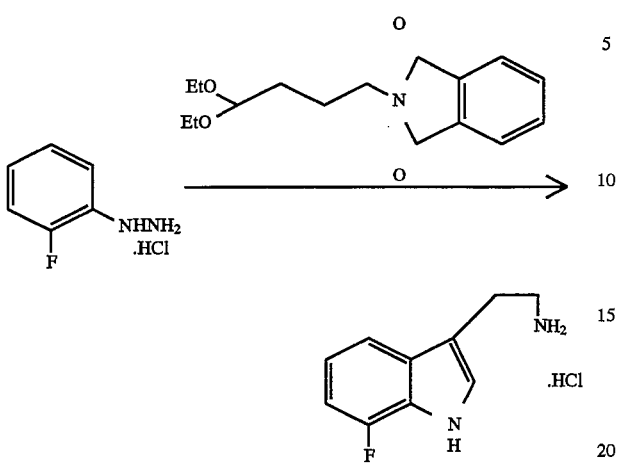

The desired 7-fluoro-1H-indole-3-ethanamine was prepared substantially as described in Example 49 infra. except that 2-fluorophenylhydrazine hydrochloride (25.5 g) was used. Additionally, reverse phase HPLC was required for final purification.

Yield: 4 g melting point: 187°–189° C. Elemental Analysis: C 55.12; H 5.48; N 12.60.

EXAMPLE 49

7-methoxy-1H-indole-3-ethanamine

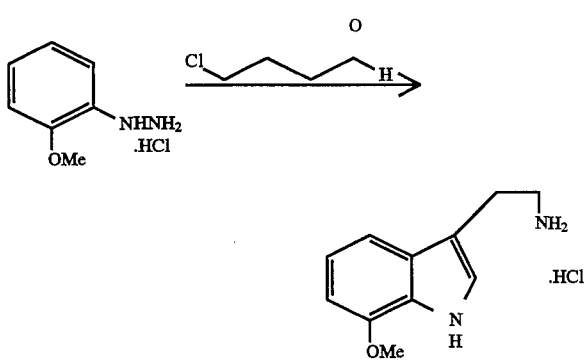

A 15.8 g sample of 2-methoxyphenylhydrazine hydrochloride and a 26.3 g sample of 4-phthalimidobutyraldehyde diethyl acetal were stirred in ethanol. The mixture was heated at reflux for 2 hours. The reaction mixture was allowed to cool and was concentrated to a residue.

The resulting residue was dissolved in 750 mL ethanol and 15.5 g hydrazine hydrate was added. The mixture was heated at reflux for 14 hours. A 70 mL sample of 5N HCl was added and the mixture was allowed to cool. The cooled mixture was concentrated to a residue. The residue was partitioned between iN NaOH and chloroform. The organic portion was separated and the aqueous portion was extracted with chloroform. The combined organic extracts were dried (Na$_2$SO$_4$) and concentrated to an oil. The oil was chromatographed on silica gel using a gradient of 0–10% methanol in chloroform. Fractions containing product were concentrated to an oil which was taken up into a small amount of methanol and added to ethereal HCl. A solid was collected, washed with diethyl ether, and vacuum dried at 50° C. to afford a white solid.

Yield: 7.5 g (37%) melting point: 198°–200° C. Elemental Analysis: C 58.46; H 6.92; N 12.22.

EXAMPLE 50

7-chloro-1H-indole-3-ethanamine

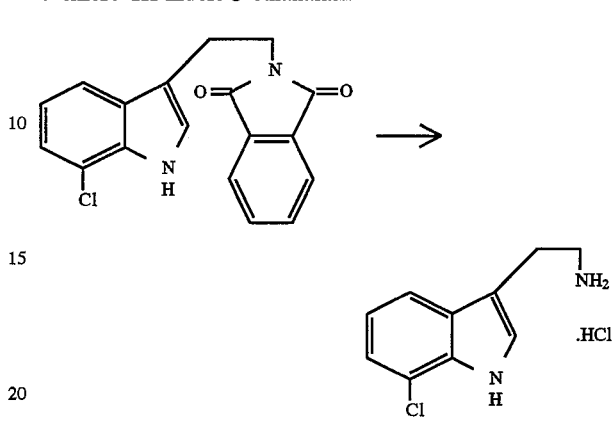

A 10.0 g sample of 2-chlorophenylhydrazine hydrochloride and 17.9 g of 4-phthalimidobutyraldehyde diethyl acetal were stirred in 200 mL ethanol with 1 mL 5 N HCl. The mixture was concentrated to a residue which was slurried in a small amount of methylene chloride. A yellow solid was collected and vacuum dried at 40° C. The solid was stirred in 500 mL ethanol. Hydrazine hydrate (14 g) was added and the mixture was heated at reflux for 14 hours. A 60 mL sample of 5N HCl was added and the mixture was heated at reflux for 1 hour. The mixture was allowed to cool and was concentrated to a residue. The residue was partitioned between 1N NaOH and chloroform. The organic layer was separated and the aqueous layer was extracted with chloroform. The combined extracts were dried (Na$_2$SO$_4$) and concentrated to an oil. The oil was chromatographed on silica gel using a gradient of 0–10% methanol in chloroform containing 0.2% ammonium hydroxide. Fractions containing product were concentrated to an oil which was taken up in a small amount of methanol and added to ethereal HCl. A solid was collected, washed with diethyl ether, and vacuum dried at 50° C.

Yield: 3.2 g (25%) Melting Point: 227°–229° C. Elemental Analysis: C 51.76; H 5.29; N 11.97.

EXAMPLE 51

5-methyl-7-chloro-1H-indole-3-ethanamine

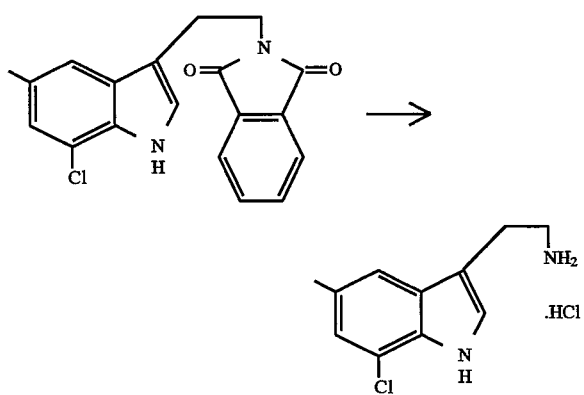

The desired product was prepared substantially as described in Example 50.

Yield: 4.3 g (34%) Melting Point: 279°–281° C. Elemental Analysis: C 54.05; H 5.85; N 11.33.

EXAMPLE 52

1-H-Benz(G)indole-3-ethanamine

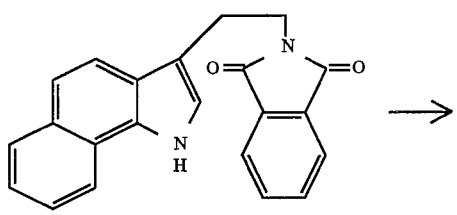

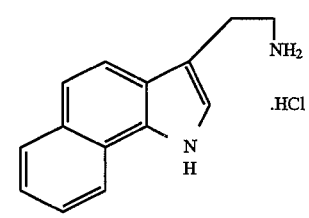

1-H-Benz(G)indole-3-ethanamine was prepared using substantially the process described in Example 50.

Yield: 3.5 g (17%) Melting Point: 305°–307° C. Elemental Analysis: C 68.43; H 6.30; N 11.08.

EXAMPLE 53

6-methyl-7-chloro-1H-indole-3-ethanamine and 6-bromo-7-methyl-1H-indole-3-ethanamine

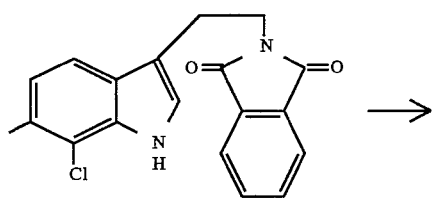

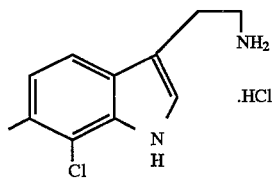

6-methyl-7-chloro-1H-indole-3-ethanamine was prepared using substantially the same process described in Example 50.

Yield: 3.0 g (24%) Melting Point: 290° C. Elemental Analysis: C 54.10; H 5.88; N 11.66.

6-bromo-7-methyl-1H-indole-3-ethanamine was prepared substantially as described in Example 50 using appropriate starting materials.

Yield: 1.6 g (56%) Melting Point: 251° C. Elemental Analysis: C 45.85; H 4.97; N 9.71.

EXAMPLE 54

6-methyl-1H-indole-3-ethanamine

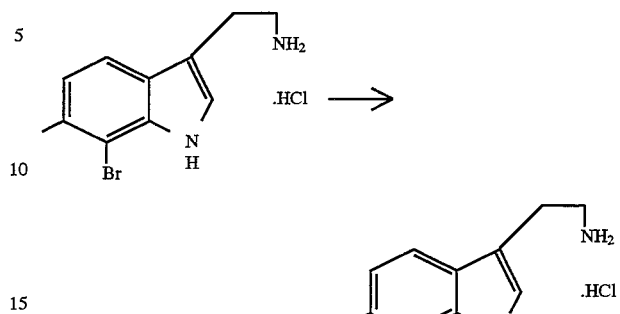

A sample of 6-methyl-7-bromo-1H-indole-3-ethanamine was contacted with Pd/C $H_2$ in the presence of ethanol and triethylamine. The resulting material was evaporated and partitioned between base/$CHCl_3$. The organic phase was dried, concentrated, and dried. The resulting material was taken up into methanol and added to ethereal HCl. The resulting material was washed and vacuum dried.

Melting Point: 232°–236° C. Elemental Analysis: C 62.84; H 7.24; N 13.20.

EXAMPLE 55

5-methyl-7-bromo-1H-indole-3-ethanamine

A sample of 5-methyl-7-bromo-1H-indole-3-ethanamine was prepared using appropriate starting materials and substantially the process described in example 47.

Yield: 16%

A 0.6 g sample of 5-methyl-7-bromo-1H-indole-3-ethanamine hydrochloride salt was converted to the free base and chromatographed on silica. The desired fractions were pooled and evaporated. The resulting material was taken up into ethyl acetate, filtered, diluted with ether, and maleic acid in methanol. The product was crystallized using ether, filtered, and dried.

Yield: 67% Melting Point: 185°–187° C. Elemental Analysis: C 49.09; H 4.85; N 7.71.

EXAMPLE 56

6,7-dimethyl-1H-indole-3-ethanamine

A sample of 6,7-dimethyl-1H-indole-3-ethanamine was prepared using appropriate starting materials and substantially the process described in Example 47. The 6,7-dimethyl-1H-indole-3-ethanamine was purified by treating with $K_2CO_3$ and extracting with 3:1 $CHCl_3$/isopropanol. The organic phase was dried, evaporated, and chromatographed. The desired fractions were pooled, evaporated, and mixed with ethyl acetate. The resulting material was diluted with ether and maleic acid in methanol. The solid was triturated in ether and dried.

Melting Point: 171°–173° C. Elemental Analysis: C 63.20; H 6.75; N 8.98.

EXAMPLE 57

6-methyl-7-bromo-1H-indole-3-ethanamine

A sample of 6-methyl-7-bromo-1H-indole-3-ethanamine was prepared using appropriate starting materials and substantially the process described in Example 47.

Yield: 8.6%

The 6-methyl-7-bromo-1H-indole-3-ethanamine was dissolved in boiling ethanol and slowly cooled to room temperature. The solvent was reduced, the resulting material was filtered, and washed with ether. The resulting material was again filtered and washed with ether to afford the desired compound.

Melting Point: 288°–290° C. Elemental Analysis: C 45.54; H 4.80; N 9.47.

As noted above, the compounds of the present invention are useful in blocking the effect of serotonin or other agonists at $5\text{-}HT_{2A}$, $5\text{-}HT_{2B}$ and/or $5\text{-}HT_{1C}$ receptors. Thus, the present invention also provides a method for blocking $5\text{-}HT_{2A}$, $5\text{-}HT_{2B}$ or $5\text{-}HT_{1C}$ receptors in mammals comprising administering to a mammal requiring blocking of a $5\text{-}HT_{2A}$, $5\text{-}HT_{2B}$, or $5\text{-}HT_{1C}$ receptor, respectively, a receptor blocking dose of a compound of the invention.

The term "receptor blocking dose", means an amount of compound necessary to block a $5\text{-}HT_{2A}$, $5\text{-}HT_{2B}$, or $5\text{-}HT_{1C}$ receptor in a mammal. The active compounds are effective over a wide dosage range. For example, dosages per day will normally fall within the range of about 0.05 to about 250 mg/kg of body weight. In the treatment of adult humans, the range of about 0.5 to 100 mg/kg, in single or divided doses, is preferred. The ranges of about 5 mg/kg to about 60 mg/kg and about 10 mg/kg to about 50 mg/kg are especially preferred. However, it will be understood that the amount of the compound actually administered will be determined by a physician in light of the relevant circumstances, including the condition to be treated, the choice of compound to be administered, the age, weight, and response of the individual patient, the severity of the patient's symptoms, and the chosen route of administration, and therefore the above dosage ranges are not intended to limit the scope of the invention in any way. The compounds may be administered by a variety of routes such as oral, transdermal, subcutaneous, intranasal, intramuscular, and intravenous routes.

A variety of physiologic functions have been shown to be subject to be influenced by $5\text{-}HT_{1C}$ receptors. Therefore, the compounds of the present invention can be used to treat a variety of disorders in mammals associated with these receptors. Such disorders include sleeping disorders, eating disorders, including bulimia and obesity, thermoregulation, sexual disorders, hyperactivity, excessive aggression, alcoholism, anxiety, obsessive-compulsive disorders, depression, schizophrenia and schizophreniform disorders, panic disorders, Gilles de la Tourette syndrome, migraine headaches, and Alzheimer's Disease. Additionally, effects of the $5\text{-}HT_{1C}$ receptor indicate that the compounds of the present invention can be useful for relieving the sensation of pain. Thus, the present invention also provides methods for treating the above disorders and for relieving the sensation of pain.

Several examples of more specific disorders which may be treated using compounds of this invention include, but are not limited to: (numerals in parenthesis refer to the DSM-III-R Classification Codes) Attention-deficit hyperactivity disorder (314.01), conduct disorders (312.20, 312.00, 312.90), primary degenerative dementia of the Alzheimer type, senile onset (290.30, 290.20, 290.21, 290.00), primary degenerative dementia of the Alzheimer type, presenile onset (290.11, 290.12, 290.13, 290.10), alcohol withdrawal delirium (291.00), alcohol hallucinosis (291.30), alcohol, dementia associated with alcoholism (291.20), cannabis, delusional disorder (292.11), cocaine, intoxication (305.60), hallucinogen, mood disorder (292.84), nicotine withdrawal (292.00), phencyclidine or similarly acting arylcyclohexylamine intoxication (305.90), other psychoactive substance intoxication (305.90), delirium (293.00), dementia (294.10), organic delusional disorder (293.81), organic hallucinosis (293.82), organic mood disorder (293.83), organic anxiety disorder (294.80), organic personality disorder (310.10), organic mental disorder (294.80), schizophrenia, catatonic (295.21, 295.22, 295.23, 295.24, 295.25, 295.20), schizophrenia, disorganized (295.11, 295.12, 295.13, 295.14, 295.15, 295.00), schizophrenia, paranoid (295.31, 295.32, 295.33, 295.34, 295.35, 295.00), schizophrenia, undifferentiated (295.91, 295.92, 295.93, 295.94, 295.95, 295.00), schizophrenia, residual (295.61, 295.62, 295.63, 295.64, 295.65, 295.60), delusional (paranoid disorder (297.10), schizophreniform disorder (295.40), schizoaffective disorder (295.70), induced psychotic disorder (297.30), bipolar disorder, mixed (296.61, 296.62, 296.63, 296.64, 296.65, 296.66, 296.60), bipolar disorder, manic (296.41, 296.42, 296.43, 296.44, 296.45, 296.46, 296.40), bipolar disorder, depressed (296.51, 296.52, 296.53, 296.54, 296.55, 296.56, 296.50), major depression, single episode (296.21, 296.22, 296.23, 296.24, 296.25, 296.26, 296.20), major depression, recurrent (296.31, 296.32, 296.33, 296.34, 296.35, 296.36, 296.30), obsessive compulsive disorder (300.30), post-traumatic stress disorder (309.89), generalized anxiety disorder (300.02), hypochondriasis (300.07), somatization disorder (300.81), male erectile disorder (302.72), intermittent explosive disorder (312.34), impulse control disorder (312.39), paranoid (301.00), schizoid (301.20), schizotypal (301.22), antisocial (301.70), and borderline (301.83). *Diagnostic and Statistical Manual of Mental Disorders*, 3rd Ed. Revised, (1980), prepared by the Task Force on Nomenclature and Statistics of the American Psychiatric Association.

One particularly useful embodiment of this invention is that it provides selective ligands for the $5\text{-}HT_{1c}$ receptor. Compounds with a high affinity for the $5\text{-}HT_{1c}$ receptor generally are cross-reactive with the $5\text{-}HT_2$ receptor as well. Now $5\text{-}HT_{1c}$ receptors can be selectively modulated using compounds of this invention at rates set forth above for blocking the effects of agonists at $5\text{-}HT_{1c}$ receptors. The selective affinity may provide treatments with fewer side effects and will facilitate the development of additional therapeutic agents.

The compounds of the present invention have been found to display excellent activity in a $5\text{-}HT_{1c}$ receptor binding assay which measures the affinity of the compounds to bind to $5\text{-}HT_{1c}$ receptors. Conversely, compounds with selective $5\text{-}HT_{1c}$ activity displayed low affinity for the $5\text{-}HT_2$ receptor. Therefore, the compounds were tested for $5\text{-}HT_2$ affinity to determine the selective $5\text{-}HT_{1c}$ effect. The assays were conducted by the following procedures.

I. Assay for $5\text{-}HT_{1c}$ Affinity:

$5\text{-}HT_{1c}$ selective compounds can be identified using the following biological assay procedures. Compounds having a selective affinity for the $5\text{-}HT_{1c}$ receptor have a low $IC_{50}$ in the $5\text{-}HT_{1c}$ receptor assay and a higher $IC_{50}$ in the $5\text{-}HT_2$ receptor assay. As shown by Table II (below) the compounds prepared in Examples 3, 4, 6, 7, 10, 13, 15, and 16 are particularly $5\text{-}HT_{1c}$ selective.

IA. Biological Reagent Preparation.

Beef brain was removed immediately after slaughter, and choroid plexus were dissected over ice. Male Sprague-Dawley rats weighing 125–150 g (Harlan Industries, Cumberland, Ind.) were killed by decapitation. The brain of each was immediately removed and the cerebral cortex was dissected over ice. Tissues were homogenized in 9 volumes of 0.32 mol/L sucrose and centrifuged at 1,000×g for 10 minutes. The supernatant was centrifuged at 17,000×g for 20 minutes. The pellet was suspended in 100 volumes of 50 mM Tris-HCl (pH 7.4), incubated at 37° C. for 10 minutes and centrifuged at 50,000×g for 10 minutes, and the process was repeated three times. The final pellets were frozen at −70° C. and used within 2 weeks. Pellets were rehydrated with physiological buffer prior to use.

II. Assay Procedure.

Radioligand binding assays for 5-$HT_{1C}$ and 5-$HT_2$ receptors were conducted according to described methods. The assays can be conducted as described by Hoyer D, Functional correlates of serotonin 5-$HT_1$ recognition sites, *J. Receptor Res* 8, 59–81 (1988) and Hoyer D, Engel G, Kalkman HO Molecular pharmacology of 5-$HT_1$ and 5-$HT_2$ recognition sites in rat and pig brain membranes: Radioligand binding studies with [$^3$H]5-HT, [$^3$H]8 -OH-DPAT, (−)[$^{125}$I]iodocyanopindolol, [$^3$H]mesulergine and [$^3$H]ketanserin, *Eur. J. Pharmacol.* 118, 13–23 (1985).

For 5-$HT_{1C}$ receptor assays increasing concentrations of experimental compound, 50 mM Tris HCl buffer pH 7.4, and tritiated mesulergine (2.0 nM) ($^3$H ligand) were combined in polystyrene tubes at room temperature. The reaction was initiated by the addition of the resuspended choroid plexus tissue which had been preincubated at 37° C. for 20 minutes. The reaction mixture was incubated in a 37° C. water bath for 15 minutes.

For 5-$HT_2$ receptor assays increasing concentrations of experimental compound, 50 mM Tris HC1 buffer pH 7.4, and tritiated ketanserin (1 nM) ($^3$H ligand) were combined in polystyrene tubes at room temperature. The reaction was initiated by the addition of the resuspended rat cerebral cortex tissue which had been preincubated at 37° C. for 20 minutes. The reaction mixture was incubated in a 37° C. water bath for 30 minutes.

The above assays were modified after a number of compounds had been screened to accommodate the unexpectedly high potency of the compounds of this invention in the 5-$HT_{1C}$ assay. The concentration range of the experimental compound in the assays was changed from [0.1 to 1000 (nM)] to [0.1 to 100 (nM)] to optimize the use of reagents and analysis time. The $IC_{50}$ values in Table II which are over 100 nM were accumulated before the modification of the concentration range of the experimental compound in the assay.

The reactions were terminated by rapid filtration, (Brandel Cell Harvestor), through Whatman GF/B glass filters that had been presoaked in Tris buffer pH 7.4. The filters were then washed 2 times with 5 ml of ice cold Tris buffer pH 7.4. Washed filters were placed in scintillation vials and 10 ml RedySolv, (Brandel), was added and samples were counted in a Searle D-300 beta counter. Means and standard error statistics were calculated for triplicate experimental determinations in certain cases. Mean values were obtained from three or more separate determinations. The incubation time for the reaction mixture was 15 minutes at 37° C.

Concentrations that caused a 50% inhibition of radioligand binding (IC50) and Hill coefficient were obtained by computer-assisted regression analysis.

The results of the evaluation of certain compounds of the present invention in the 5-$HT_{1C}$ and 5-$HT_2$ binding assays are set forth below in Table II. In the Table, column 1 sets forth the Example Number of the compound evaluated, columns 2 and 3 are the IC50 (nM) values for the 5-$HT_{1C}$ and B-$HT_2$ receptors respectively.

TABLE II

| 5-HT Receptor Binding Displacement Assay | | |
|---|---|---|
| Example | 5HT1C | 5HT2 |
| 1 | 213 | 310 |
| 2 | 34 | 67 |
| 3 | 29 | 900 |
| 4 | 20 | 132 |
| 5 | 237 | 255 |
| 6 | 43 | 168 |
| 7 | 5.1 | >100 |
| 8 | 22 | >100 |
| 9 | 18 | 141 |
| 10 | 43 | 219 |
| 11 | 365 | >1000 |
| 12 | 15 | >100 |
| 13 | 48 | 433 |
| 14 | 34 | >100 |
| 15 | 14 | >100 |
| 16 | 63 | 2112 |
| 17 | 73 | 286 |
| 18 | 119 | 287 |
| 19 | 21 | >100 |
| 20 | 100 | 129 |
| 21 | 83 | 1077 |
| 22 | 30 | 1417 |
| 23 | 57 | *** |
| 24 | 17 | 74 |
| 25 | 79 | *** |
| 26 | 53 | *** |
| 27 | ** | ** |
| 28 | 404 | 1000 |
| 29 | 257 | 1010 |
| 30 | 224 | 792 |
| 31 | 107 | 385 |
| 32 | ** | ** |
| 33 | ** | ** |
| 34 | 95 | 250 |
| 35 | 61 | >100 |
| 36 | 57 | 100 |
| 37 | 29 | 100 |
| 38 | 11 | >100 |
| 39 | 498 | 620 |
| 40 | 171 | 293 |
| 41 | 127 | 173 |
| 42 | 86 | 211 |
| 43 | 139 | 178 |
| 44 | 386 | *** |
| 45 | 452 | *** |
| 46 | 31 | 100 | and *refer to compounds not tested.

Certain compounds and tryptamine-like intermediates of the present invention are useful for modulating 5-$HT_{2B}$ receptors. The compounds which are most useful for binding a 5$HT_{2B}$ receptor can be identified using the following procedures. Further, a useful in vivo model for demonstrating 5-$HT_{2B}$ activity is provided infra.

II. Radioligand Binding Studies for 5-HT2B:

Membrane preparation from transformed cells. Suspension cells expressing the cloned rat 5-$HT_{2B}$ receptor were harvested by centrifugation at 2,200×g for 15 min at 4° C. Kursar, J. D., D. L. Nelson, D. B. Wainscott, M. L. Cohen, and M. Baez, Mol. Pharmacol., 42:549–557 (1992). Membranes for the binding assays were prepared by vortexing the pellet in 50 mM Tris-HCl, pH 7.4 (0.5×10$^9$ cells/30 ml). The tissue suspension was then centrifuged at 39,800×g for 10 min at 4° C. This procedure was repeated for a total of three washes, with a 10 minute incubation at 37° C. between the first and second wash. The final pellet was homogenized in 67 mM Tris-HCl, pH 7.4 (at 20–40 and 12.5 million cells/ml, original cell number, for cells expressing low and relatively high levels of the 5-HT2B receptor, respectively) using a Tissumizer (Tekmar, Cincinnati, Ohio), setting 65 for 15 seconds.

[³H]5-HT binding studies. Binding assays were automated using a Biomek 1000 (Beckman Instruments, Fullerton, Calif.) and were performed in triplicate in 0.8 ml total volume. Membrane suspension, 200 μl, (0.04–0.27 mg protein) and 200 μl of drug dilution in water were added to 400 μl of 67 mM Tris-HCl, pH 7.4, containing [3H]5-HT, pargyline, CaCl$_2$, and L-ascorbic acid. Final concentrations of pargyline, CaCl$_2$ and L-ascorbic acid were 10 μM, 3 mM and 0.1%, respectively. Tubes were incubated at 37° C. for 15 min or at 0° C. for 2 hours (binding equilibria were verified for both of these conditions), then rapidly filtered using a Brandel cell harvester (Model MB-48R; Brandel, Gaithersburg, Md.) through Whatman GF/B filters which had been presoaked in 0.5% polyethylenimine and pre-cooled with ice-cold 50 mM Tris-HCl, pH 7.4. The filters were then washed rapidly four times with one ml ice-cold 50 mM Tris-HCl, pH 7.4. The amount of [³H]5-HT trapped on the filters was determined by liquid scintillation spectrometry (Ready Protein and Beckman LS 6000IC, Beckman Instruments, Fullerton, Calif.). For the saturation experiments, actual free radioligand concentrations were determined by sampling the supernatant of parallel saturation experiments in which bound radioactivity had been separated by centrifugation. The concentration of [³H]5-HT ranged from 0.02 to 5 nM and 0.6 to 63 nM for saturation experiments incubated at 0° C. and 37° C., respectively. 5-HT, 10 μM, or 1-naphthylpiperazine (1-NP), 10 μM, defined nonspecific binding. For competition experiments, six to twelve concentrations of displacing drugs were used, spanning six log units, and the final concentration of [³H] 5-HT was 2 nM. Protein was determined by the method of Bradford, using bovine serum albumin as the standard. Bradford, M. M., Anal. Biochem. 72:248–254 (1976).

Statistical Analysis:

The K$_d$ and B$_{max}$ values from the saturation assays were determined for best fit to a one-site or a two-site binding model using a partial F-test. De Lean, A., A. A. Hancock, and R. J. Lefkowitz, Mol. Pharmacol. 21:5–16 (1981). The following equation was used for a one-site binding model, $$Bound = \frac{B_{max} \times [L]}{K_d + [L]}$$

where Bound=amount of [³H]5-HT specifically bound, B$_{max}$,32 maximum number of binding sites, K$_d$=equilibrium dissociation constant and [L]=free concentration of [³H]5-HT, or a two-site binding model, $$Bound = \frac{B_{max1} \times [L]}{K_{d1} + [L]} + \frac{B_{max2} \times [L]}{K_{d2} + [L]}$$

where Bound=amount of [³H]5-HT specifically bound, B$_{max1}$=maximum number of high affinity binding sites, B$_{max2}$=maximum number of low affinity binding sites, K$_{d1}$=equilibrium dissociation constant for the high affinity site, K$_{d2}$=equilibrium dissociation constant for the low affinity site and [L]=free concentration of [³H]5-HT. The IC$_{50}$ values from the competition assays, the binding parameters for the IP$_3$ standard curve and the EC$_{50}$ and E$_{max}$ values from the IP$_3$ assays were determined by nonlinear regression analysis of four parameter logistic equations (Systat, Systat Inc, Evanston, Ill.). De Lean, A., A. A. Hancock, and R. J. Lefkowitz, Mol. Pharmacol., 21:5–16 (1981). The IC$_{50}$ values were converted to K$_i$ values using the Cheng-Prusoff equation. Cheng, Y., and W. H. Prusoff, Biochem. Pharmacol., 22:3099–3108 (1973).

Table III (infra.) illustrates the binding of compounds tested using the radioligand assay.

TABLE III

| Compound of Example | Rat 2B | Human 2B | Human 2A |
|---|---|---|---|
| 8 | 39.7 | — | — |
| 11 | 1463.01 | — | — |
| 17 | 8.16 | 1.50 | 23.39 |
| 20 | 3.10 | 0.79 | 28.07 |
| 22 | 5.39 | — | — |
| 40 | 5.61 | 1.40 | 44.46 |
| 41 | 6.42 | 2.01 | 23.08 |
| 43 | — | 0.87 | 17.48 |
| 46 | 2.16 | — | — |

III. Assay Methods 5-HT2B in vitro:

Male Wistar rats (150–375 g; Laboratory Supply, Indianapolis, Ind.) were sacrificed by cervical dislocation, and longitudinal section of the stomach fundus were prepared for in vitro examination. Four preparations were obtained from one rat fundus. Ring preparations of the extracted jugular vein were prepared as described by Hooker; Blood Vessels 14:1 (1977) and Cohen, M. L. J. Pharamcol. Exp. Ther. 227:327 (1983). Tissues were mounted in organ baths containing 10 mL of modified Krebs solution of the following composition (millimolar concentrations): NaCl, 118.2, KCl, 4.6; CaCl$_2$.H$_2$O, 1.6; KH$_2$PO$_4$, 1.2; MgSO$_4$, 1.2; dextrose, 10.0; and NaHCO$_3$, 24.8. Tissue bath solutions were maintained at 37° C. and equilibrated with 95% O$_2$ and 5% CO$_2$. Tissues were placed under optimum resting force (4 g) and were allowed to equilibrate for approximately 1 hour before exposure to the test compound. Isometric contractions were recorded as changes in grams of force on a Beckman Dynograph with Statham UC-3 transducers.

Determination of Apparent Antagonist Dissociation Constant:

Noncumulative contractile concentration-response curves for serotonin in the fundus and cumulative concentration response curves in the jugular vein were obtained by a stepwise increase in concentration after washing out the preceding concentrations every 15–20 minutes. Each agonist concentration remained in contact with the tissue for approximately 2 minutes and maximum response to each compound concentration was measured ED$_{50}$ values were taken as the concentration of agonist that produced half-maximal contraction. After control responses were obtained, tissues were incubated with an appropriate concentration of buffer or antagonist for 1 hour. Responses to serotonin were then repeated in the presence of an antagonist. Concentration responses utilized only one agonist and one antagonist concentration per tissue. In general, successive agonist responses in the presence of buffer treatment were unaltered (average dose ratio was 1.28+/−0.21).

Apparent antagonist dissociation constants (K$_B$) were determined for each concentration of antagonist according to the following equation:

K$_B$=[B]/(dose ratio-1)

where [B] is the concentration of the antagonist and dose ratio is the ED$_{50}$ of the agonist in the presence of the antagonist divided by the control ED$_{50}$. Generally, parallel shifts in the concentration-response curves occurred in the presence of antagonists. The results were expressed as the negative logarithm of the K$_B$ (i.e., −log KB). Calculations were completed using known methods. Zaborowsky, B. R. J. Pharmacol. Methods 4:4165 (1980).

Compounds of this invention were tested and demonstrated 5-HT$_{2B}$ receptor activity using this described in vitro method.

In vivo Studies:

Sprague-Dawley Rats (250–300 g) were fasted overnight. The rats were anesthetized with urethane (250 mg) delivered intraperitoneally. The abdominal cavity was opened and strain guage transducers were sewn on the antimesenteric border of the colon. The transducers were oriented to record circular muscle contractions. The animal body temperature was maintained by a heating pad. An intravenous catheter was inserted into the jugular vein for drug administration. The carotid blood pressure was also monitored. Output of the strain guage transducers was graphed on a Beckman Dynograph. Baseline motility was monitored for 30 minutes. At the end of the 30 minute period, a vehicle control dose was administered and motility was recorded for an additional 15 minutes. A serotonin dose response was developed. Successively higher doses of serotonin were administered at 15 minute intervals. An ED$_{50}$ dose was calculated, which was the dose producing half maximal contraction. In antagonist experiments, historical ED$_{50}$ dose was administered to validate the experimental set up. Next, a dose of antagonist was given. The motility was monitored for 15 minutes. After the 15 minute monitoring, an ED$_{50}$ dose was administered. Motility was evaluated by measuring the number of contractions and multiplying them by the amplitude of contractions over a set time period to provide a Motility Index. The percent inhibition was calculated from the vehicle (no antagonist) treated group. A minimum of three rats were used for each concentration and data from different animals was pooled to determine ED$_{50}$ values.

Compounds exhibiting activity at the 5HT$_{2B}$ receptor are useful for treating disorders related to the modulation of the 5HT$_{2B}$ receptor. For example, compounds having 5HT$_{2B}$ antagonist activity reduce the spasticity of the colon. Thus, these compounds are useful for the treatment of functional bowel disorders including irritable bowel syndrome and irritable bowel syndrome-related symptoms. The antispasmodic effect of such compounds can reduce abdominal pain associated with functional bowel disorders. Additionally, the 5HT$_{2B}$ receptor is localized in other organs such as the brain, bladder, blood vessels, stomach, and uterus, indicating that additional conditions are 5HT$_{2B}$ mediated.

Compounds demonstrating activity at the 5HT$_{2A}$ receptor can be utilized in the treatment or prevention of conditions related to modulation of the 5HT$_{2A}$ receptor. Examples of such conditions include hypertension, sleep disorders, hallucinogenic activity, psychosis, anxiety, depression, thermoregulation, feeding disorders, and hypotension. Leonard, B. E., *International Clinical Psychopharmacology*, 7, 13–21 (1992).

While it is possible to administer a compound of the invention directly without any formulation, the compounds are preferably employed in the form of a pharmaceutical formulation comprising a pharmaceutically acceptable excipient and at least one compound of the invention. Such compositions contain from about 0.1 percent by weight to about 90.0 percent by weight of a present compound. As such, the present invention also provides pharmaceutical formulations comprising a compound of the invention and a pharmaceutically acceptable excipient therefor.

In making the compositions of the present invention, the active ingredient is usually mixed with an excipient which can be a carrier, or a diluent or be diluted by a carrier, or enclosed within a carrier which can be in the form of a capsule, sachet, paper or other container. When the carrier serves as a diluent, it can be a solid, semi-solid, or liquid material which acts as a vehicle, excipient, or medium for the active ingredient. Thus, the composition can be in the form of tablets, pills, powders, lozenges, sachets, cachets, elixirs, emulsions, solutions, syrups, suspensions, aerosols (as a solid or in a liquid medium), and soft and hard gelatin capsules.

The compounds of the invention may be delivered transdermally, if desired. Transdermal permeation enhancers and delivery systems, including patches and the like, are well known to the skilled artisan.

Examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propylhydroxy- benzoates, talc, magnesium stearate, water, and mineral oil. The formulations may also include wetting agents, emulsifying and suspending agents, preserving agents, sweetening agents or flavoring agents. The formulations of the invention may be formulated so as to provide quick, sustained, or delayed release of the active ingredient after administration to the patient by employing procedures well known in the art.

The compounds of this invention may be delivered transdermally using known transdermal delivery systems and excipients. Most preferably, a compound of this invention is admixed with permeation enhancers including, but not limited to, propylene glycol, polyethylene glycol monolaurate, and azacycloalkan-2-ones, and incorporated into a patch or similar delivery system. Additional excipients including gelling agents, emulsifiers, and buffers may be added to the transdermal formulation as desired.

For oral administration, a compound of this invention ideally can be admixed with carriers and diluents and molded into tablets or enclosed in gelatin capsules.

The compositions are preferably formulated in a unit dosage form, each dosage containing from about 1 to about 500 mg, more usually about 5 to about 300 mg, of the active ingredient. The term "unit dosage form" refers to physically discrete units suitable as unitary dosages for human subjects and other mammals, each unit containing a predetermined quantity of active material calculated to produce the desired therapeutic effect in association with a suitable pharmaceutical carrier.

In order to more fully illustrate the operation of this invention, the following formulation examples are provided. The examples are illustrative only, and are not intended to limit the scope of the invention. The formulations may employ as active compounds any of the compounds of the present invention.

FORMULATION 1

Hard gelatin capsules are prepared using the following ingredients:

| | Amount Per Capsule | Concentration by Weight (percent) |
|---|---|---|
| (+/−) 6-ethyl-8-chloro-1-[(3,4-dimethoxyphenyl)methyl]-1,2,3,4-tetrahydro-9H-pyrido[3,4-b]indole hydrochloride | 250 mg | 55.0 |
| starch dried | 200 mg | 43.0 |

|   | Amount Per Capsule | Concentration by Weight (percent) |
|---|---|---|
| magnesium stearate | 10 mg | 2.0 |
|   | 460 mg | 100.0 |

The above ingredients are mixed and filled into hard gelatin capsules in 460 mg quantities.

FORMULATION 2

Capsules each containing 20 mg of medicament are made as follows:

|   | Amount Per Capsule | Concentration by Weight (percent) |
|---|---|---|
| 6-methyl-8-ethyl-1-[(3-bromo-4-chloro-phenyl)-methyl)-1,2,3,4-tetrahydro-9H-pyrido[3,4b]indole (Z)-2-butenedioate | 20 mg | 10.0 |
| starch | 89 mg | 44.5 |
| microcrystalline cellulose | 89 mg | 44.5 |
| magnesium stearate | 2 mg | 1.0 |
|   | 200 mg | 100.0 |

The active ingredient, cellulose, starch, and magnesium stearate are blended, passed through a No. 45 mesh U.S. sieve and filled into a hard gelatin capsule.

FORMULATION 3

Capsules each containing 100 mg of medicament are made as follows:

|   | Amount Per Capsule | Concentration by Weight (percent) |
|---|---|---|
| 5-fluoro-6-methyl-1-(1-(3-methylaminophenyl)-methyl)-1,2,3,4-tetrahydro-9H-pyrido-[3,4-b]indole (Z)-2-butenedioate | 100 mg | 30.00 |
| polyoxyethylene sorbitan monooleate | 50 mg | 0.02 |
| starch powder | 250 mg | 69.98 |
|   | 350 mg | 100.00 |

The above ingredients are thoroughly mixed and placed in an empty gelatin capsule.

FORMULATION 4

Tablets containing 10 mg of active ingredient are made as follows:

|   | Amount Per Tablet | Concentration by Weight (percent) |
|---|---|---|
| 6-fluoro-8-phenoxy-1-(1-(4-ethoxy-phenyl)-methyl)-1,2,3,4-tetrahydro-9H-pyrido-[3,4-b]indole (Z)-2-butenedioate | 10 mg | 10.0 |
| starch | 45 mg | 45.0 |
| microcrystalline cellulose | 35 mg | 35.0 |
| polyvinylpyrrolidone (as 10% solution in water) | 4 mg | 4.0 |
| sodium carboxymethyl starch | 4.5 mg | 4.5 |
| magnesium stearate | 0.5 mg | 0.5 |
| talc | 1 mg | 1.0 |
|   | 100 mg | 100.0 |

The active ingredient, starch and cellulose are passed through a No. 45 mesh U.S. sieve and mixed thoroughly. The solution of polyvinylpyrrolidone is mixed wiht the resultant powders which are then passed through a No. 14 mesh U.S. sieve. The granule so produced is dried at 50°–60° C. and passed through a No. 18 mesh U.S. sieve. The sodium carboxymethyl starch, magnesium stearate and talc, previously passed through a No. 60 mesh U.S. sieve, are then added to the granule which, after mixing, is compressed on a tablet machine to yield a tablet weighing 100 mg.

FORMULATION 5

A tablet formulation may be prepared using the ingredients below:

|   | Amount Per Tablet | Concentration by Weight (percent) |
|---|---|---|
| 5,6-difluoro-1-(1-(3-dimethylamino-phenyl)-methyl)-1,2,3,4-tetrahydro-9H-pyrido-[3,4-b]indole (Z)-2-butanedioate | 250 mg | 38.0 |
| microcrystalline cellulose | 400 mg | 60.0 |
| silicon dioxide fumed | 10 mg | 1.5 |
| stearic acid | 5 mg | 0.5 |
|   | 665 mg | 100.0 |

The components are blended and compressed to form tablets each weighing 665 mg.

99

FORMULATION 6

Suspensions each containing 5 mg of medicament per 5 ml dose are as follows:

| | per 5 ml of suspension |
|---|---|
| 5-chloro-6-methyl 1-(1-(3-dimethylaminophenyl)-methyl)-1,2,3,4-tetrahydro-9H-pyrido-[3,4-b]indole (Z)-2-butenedioate | 5 mg |
| sodium carboxymethyl cellulose | 50 mg |
| syrup | 1.25 ml |
| benzoic acid solution | 0.10 ml |
| flavor | q.v. |
| color | q.v. |
| water | q.s. to 5 ml |

The medicament is passed through a No. 45 mesh U.S. sieve and mixed with the sodium carboxymethylcellulose and syrup to form a smooth paste. The benzoic acid solution, flavor and color is diluted with some of the water and added to the paste with stirring. Sufficient water is then added to produce the required volume.

FORMULATION 7

An aerosol solution is prepared containing the following components:

| | Concentration by Weight (percent) |
|---|---|
| 5-propyl-6-ethyl-1-[(3,4-dimethoxy-phenyl)-methyl]-1,2,3,4-tetrahydro-9H-pyrido-[3,4-b]indole hydrochloride | 0.25 |
| ethanol | 29.75 |
| Propellant 22 | 70.00 |
| (chlorodifluoromethane) | |
| | 100.00 |

The active compound is mixed with ethanol and the mixture added to a portion of the Propellant 22, cooled to −30° C. and transferred to a filling device. The required amount is then fed to a stainless steel container and diluted further with the remaining amount of propellant. The valve units are then fitted to the container.

FORMULATION 8

A tablet formulation may be prepared using the ingredients below:

| | Amount Per Tablet | Concentration by Weight (percent) |
|---|---|---|
| 7-bromo-1H-indole-3-ethanamine | 250 mg | 38.0 |
| microcrystalline cellulose | 400 mg | 60.0 |
| silicon dioxide | 10 mg | 1.5 |

100

-continued

| | Amount Per Tablet | Concentration by Weight (percent) |
|---|---|---|
| fumed stearic acid | 5 mg | 0.5 |
| | 665 mg | 100.0 |

The components are blended and compressed to form tablets each weighing 665 mg.

We claim:

1. A compound of the Formula (VI)

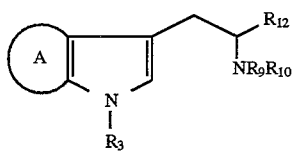

wherein:

$R_3$ is hydrogen or $C_1$–$C_3$ alkyl;

A is selected from the group consisting of

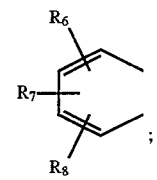

wherein $R_6$ and $R_7$ are, independently, hydrogen, $C_1$–$C_6$ alkyl, $C_2$–$C_6$ alkenyl, halo, halo($C_1$–$C_6$)alkyl, halo($C_2$–$C_6$) alkenyl, $COR_5$, $C_1$–$C_{10}$ alkanoyl, $CO_2R_5$, ($C_1$–$C_6$ alkyl)$_m$ amino, $NO_2$, —$SR_5$, or $OR_5$;

$R_5$ is hydrogen or $C_1$–$C_4$ alkyl;

$R_{5'}$ is $C_1$–$C_4$ alkyl;

$R_8$ is selected from the group consisting of an $R_6$ group, substituted $C_3$–$C_8$ cycloalkyl, $C_3$–$C_8$ cycloalkyl, $C_3$–$C_8$ cycloalkyl-($C_3$–$C_8$)alkyl, $C_5$–$C_8$ cycloalkenyl, substituted $C_5$–$C_8$ cycloalkenyl, $C_5$–$C_8$ cycloalkenyl-($C_1$–$C_3$)alkyl, and $C_7$–$C_{16}$ arylalkyl;

$R_9$ and $R_{10}$ are independently selected from the group consisting of hydrogen, $C_1$–$C_6$ alkyl, substituted $C_3$–$C_8$ cycloalkyl, $C_3$–$C_8$ cycloalkyl, $C_3$–$C_8$ cycloalkyl-($C_1$–$C_3$)alkyl, $C_5$–$C_8$ cycloalkenyl-($C_1$–$C_3$)alkyl, $C_7$–$C_{16}$ arylalkyl;

$R_{12}$ is hydrogen or $C_1$–$C_3$ alkyl;

m is 1 or 2;

provided that, a) when A is

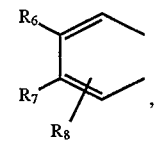

and $R_6$ and $R_7$ are hydrogen, halo or $OR_5$, then $R_8$ cannot be hydrogen;

b) when A is formula IV', $R_6$ is $OR_5$, and $R_9$, $R_{10}$ and $R_{12}$ are each hydrogen, then only one of $R_7$ and $R_8$ can be halo;

c) when $R_9$, $R_{10}$ and $R_{12}$ are each hydrogen, and
   (i) two of $R_6$, $R_7$ and $R_8$ are selected from halo, $C_1$–$C_6$ alkyl, $OR_5$, and —$SR_5$, then the third $R_6$, $R_7$ or $R_8$ substituent cannot be hydrogen; or
   (ii) one of $R_6$, $R_7$ and $R_8$ is halo, then it must be located at the 7- position of the VI compound; and
d) when $R_9$ and $R_{10}$ are each hydrogen, $R_{12}$ is hydrogen or $C_1$–$C_3$ alkyl, and two of $R_6$, $R_7$ and $R_8$ are hydrogen, then the third $R_6$, $R_7$ or $R_8$ cannot be $C_1$–$C_6$ alkyl, halo, halo($C_1$–$C_6$)alkyl, $NO_2$, —$SR_5$, or —$OR_5$;

or a pharmaceutically acceptable salt or solvate thereof.

2. A compound of claim 1 selected from the group consisting of 6,7-dimethyl-1H-indole-3-ethanamine, 5-methyl-7-bromo-1H-indole-3-ethanamine, 6-methyl-7-chloro-1H-indole-3-ethanamine, 5-methyl-7-chloro-1H-indole-3-ethanamine, and 6-methyl-7-bromo-1H-indole-3-ethanamine.

3. A compound of claim 1 wherein $R_6$ is hydrogen; $R_7$ is at the 7-position of the compound and is $C_{1-4}$ alkyl, $OR_5$ or halo; and $R_5$ is $C_{1-4}$ alkyl.

4. A compound of claim 1 wherein $R_9$, $R_{10}$, and $R_{12}$ are each hydrogen; and $R_8$ is selected from the group consisting of $C_5$–$C_6$ alkyl, halo($C_1$–$C_6$)alkyl, halo($C_2$–$C_6$)alkenyl, $C_1$–$C_{10}$ alkanoyl, $CO_2R_5$, ($C_1$–$C_6$ alkyl)m amino, substituted $C_3$–$C_8$ cycloalkyl, $C_3$–$C_8$ cycloalkyl, $C_3$–$C_8$ cycloalkyl-($C_1$–$C_3$)alkyl, $C_5$–$C_8$ cycloalkenyl, substituted $C_5$–$C_8$ cycloalkenyl, $C_5$–$C_8$ cycloalkenyl-($C_1$–$C_3$)alkyl, and $C_7$–$C_{16}$ arylalkyl.

5. A compound of claim 3 wherein $R_9$, $R_{10}$, and $R_{12}$ are each hydrogen; and $R_8$ is selected from the group consisting of $C_5$–$C_6$ alkyl, halo($C_1$–$C_6$)alkyl, halo($C_2$–$C_6$)alkenyl, $C_1$–$C_{10}$ alkanoyl, $CO_2R_5$, ($C_1$–$C_6$ alkyl)$_m$ amino, substituted $C_3$–$C_8$ cycloalkyl, $C_3$–$C_8$ cycloalkyl, $C_3$–$C_8$ cycloalkyl-($C_1$–$C_3$)alkyl, $C_5$–$C_8$ cycloalkenyl, substituted $C_5$–$C_8$ cycloalkenyl, $C_5$–$C_8$ cycloalkenyl-($C_1$–$C_3$)alkyl, and $C_7$–$C_{16}$ arylalkyl.

6. A pharmaceutical formulation comprising a compound of claim 1 and one or more pharmaceutically acceptable excipients therefor.

7. A pharmaceutical formulation comprising a compound of claim 3 and one or more pharmaceutically acceptable excipients therefor.

8. A method for treating a mammal suffering from or susceptible to a condition associated with $5HT_{1C}$ modulation, comprising administering a receptor binding dose of a $5HT_{1C}$ binding compound of claim 1.

9. A method for treating a mammal suffering from or susceptible to a condition associated with $5HT_{2A}$ modulation, comprising administering a receptor binding dose of a $5HT_{2A}$ binding compound of claim 1.

* * * * *